United States Patent
Huang et al.

(10) Patent No.: US 12,161,731 B2
(45) Date of Patent: Dec. 10, 2024

(54) RADIOACTIVE I-LABELED LAROTRECTINIB COMPOUND AND PREPARATION METHOD AND APPLICATION THEREOF

(71) Applicant: SHANGHAI UNIVERSITY OF MEDICINE&HEALTH SCIENCES, Shanghai (CN)

(72) Inventors: Gang Huang, Shanghai (CN); Bin Li, Shanghai (CN)

(73) Assignee: SHANGHAI UNIVERSITY OF MEDICINE & HEALTH SCIENCES, Shanghai (CN)

( * ) Notice: Subject to any disclaimer, the term of this patent is extended or adjusted under 35 U.S.C. 154(b) by 753 days.

(21) Appl. No.: 17/312,949

(22) PCT Filed: Sep. 19, 2019

(86) PCT No.: PCT/CN2019/106695
§ 371 (c)(1),
(2) Date: Jun. 11, 2021

(87) PCT Pub. No.: WO2020/119206
PCT Pub. Date: Jun. 18, 2020

(65) Prior Publication Data
US 2022/0072164 A1    Mar. 10, 2022

(30) Foreign Application Priority Data
Dec. 12, 2018  (CN) .......................... 201811518136.6

(51) Int. Cl.
*A61K 51/04*        (2006.01)
*C07B 59/00*        (2006.01)
*C07D 487/04*       (2006.01)

(52) U.S. Cl.
CPC ........ *A61K 51/0459* (2013.01); *C07B 59/002* (2013.01); *C07D 487/04* (2013.01); *C07B 2200/05* (2013.01)

(58) Field of Classification Search
None
See application file for complete search history.

(56) References Cited

FOREIGN PATENT DOCUMENTS

CN    102264736          11/2011
CN    107987082 A   *    5/2018   .......... C07D 487/04

OTHER PUBLICATIONS

"International Search Report (Form PCT/ISA/210) of PCT/CN2019/106695," mailed on Dec. 18, 2019, with English translation thereof, pp. 1-6.

* cited by examiner

*Primary Examiner* — Michael G. Hartley
*Assistant Examiner* — Kaila A Craig
(74) *Attorney, Agent, or Firm* — JCIP GLOBAL INC.

(57) ABSTRACT

The invention relates to a radioactive I-labeled Larotrectinib compound and a preparation method and application thereof, including a radioactive I-labeled Larotrectinib compound having the following structural formula and its analogs:

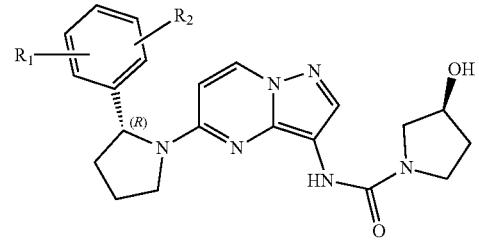

where $R_1$ and $R_2$ are respectively H, F, Cl, Br, $^{123}$I, $^{124}$I, $^{125}$I, $^{130}$I or $^{131}$I, and at least one of $R_1$ and $R_2$ is a radioactive iodine element. The invention provides a preparation method of a radioiodinated pyrazolo[1,5-*a*]pyrimidine compound base. Radioiodinated pyrazolo[1,5-*a*]pyrimidine compounds with long half-life and different ray energy can be used for PET tomography and clinical diagnostic research of SPECT. Moreover, the high-energy radioiodinated pyrazolo[1,5-*a*]pyrimidine can act as a TrK receptor ligand to inhibit the activity of TRK and kill tumor cells; and due to high-energy I-131 ray energy carried, the radioiodinated pyrazolo[1,5-*a*]pyrimidine can coordinate to shoot tumor cells and thus achieve an accurate radiotherapy effect.

16 Claims, No Drawings

RADIOACTIVE I-LABELED LAROTRECTINIB COMPOUND AND PREPARATION METHOD AND APPLICATION THEREOF

CROSS-REFERENCE TO RELATED APPLICATION

This application is a 371 of international application of PCT application serial no. PCT/CN2019/106695, filed on Sep. 19, 2019, which claims the priority benefit of China application no. 201811518136.6, filed on Dec. 12, 2018. The entirety of each of the above mentioned patent applications is hereby incorporated by reference herein and made a part of this specification.

BACKGROUND

Technical Field

The invention relates to the field of chemical drug synthesis, especially to an in vivo imaging agent for Trk receptor subtypes in refractory solid tumors, and more particularly to a preparation method of a radioactive I-labeled compound of Larotrectinib and a synthesis method of its intermediates. The invention provides a radioiodine compound based on novel TRK (tyrosine receptor kinase) inhibitor Larotrectinib and its intermediates.

Description of Related Art

Larotrectinib was developed by Loxo Oncology. As a broad-spectrum tumor drug, it is used for all tumor patients that express (TRK). This small-molecule TRK inhibitor is highly selective for TRK. By inhibiting the TRK signaling pathway, larotrectinib can inhibit tumor growth. Larotrectinib is a potent oral TRK inhibitor with consistent and long-lasting anti-tumor activity in TRK fusion tumors. It is applicable to a wide range of patient ages and tumor types and its indications are distributed in 13 different tumor types. Larotrectinib has good tolerance, is effective against a variety of solid tumors in adults and children, including salivary, infantile fibrosarcoma, lung cancer, thyroid cancer, colon cancer, melanoma (melanoma), cholangio cancer, GISTs, breast cancer, and various sarcoma cancers. The US FDA (http://www.chemdrug.com/article/11/) has granted orphan drug designation and breakthrough drug designation to larotrectinib. Larotrectinib is expected to become the first therapeutic drug to be developed and approved simultaneously for adults and children, and it is the first tumor-targeted therapeutic drug that spans all traditionally defined tumor types and molecular meanings. The structure of Larotrectinib is as follows:

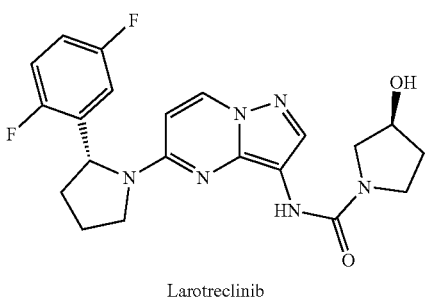 [SMILES: O=C(Nc1cnn2ccc(N3CCC[C@@H]3c3cc(F)ccc3F)nc12)N1CC[C@H](O)C1]

Larotreclinib

However, in document CN201580073515.7, for the effect of Larotrectinib compounds, based on the structural changes of autopsy or CT computed tomography CT images its function can be inferred. For the problem, how to trace the distribution of Larotrectinib online in the human body and the status of solid tumors in vivo, intuitively determine the physiological functions of Larotrectinib in tumors, and evaluate its curative effect and its prognostic effects, there is still a lack of more effective technical means.

SUMMARY

The objective of the invention is to provide a radioactive I-labeled Larotrectinib compound and a preparation method thereof in order to overcome the above-mentioned defects in the prior art. Specifically provided are a $^{123,\ 124,\ 125,\ 130,\ 131}$I-Larotrectinib radiolabeled compound labeled with I-123, I-124, I-125, I-130, and I-131 and its analogs, and further provided are a preparation method of the $^{124,\ 125,\ 127,\ 130,\ 131}$I-Larotrectinib radiolabeled compound labeled with I-124, I-125, I-127, I-130, and I-131 and a synthesis method of intermediates thereof.

The objectives of the invention can be accomplished by the following technical solution.

The compound of the invention is modified on the benzene ring structure of Larotrectinib compounds. An objective of the invention is to provide pyrazolo[1,5-a]pyrimidine compounds, namely pyrazolo[1,5-a]pyrimidine halogenated derivatives.

A radioactive I-labeled Larotrectinib compound, characterized in that, a radioactive I-labeled Larotrectinib compound having the following structural formula and its analogs:

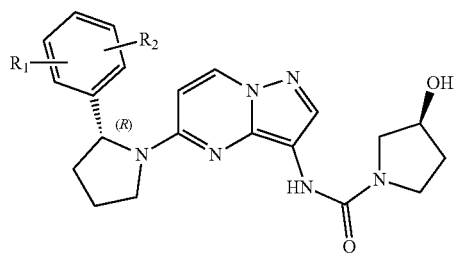

where $R_1$ and $R_2$ are respectively H, F, Cl, Br, $^{123}$I, $^{124}$I, $^{125}$I, $^{130}$I or $^{131}$I, and at least one of $R_1$ and $R_2$ is a radioactive iodine element.

The long half-life radionuclide iodine in the invention is [$^{123/124/125/130/131}$I], which refers to $^{123}$I, $^{124}$I, $^{125}$I, $^{130}$I or $^{131}$I, respectively. The half-lives of $^{123}$I, $^{124}$I, $^{125}$I, $^{130}$I and $^{131}$I are 13.0 hours, 4.2 days, 60 days, 12.3 hours, and 8.04 days, respectively.

Another objective of the invention is to provide a preparation method of the pyrazolo[1,5-a]pyrimidines; the method is implemented by the following step: a preparation method of the radioactive I-labeled Larotrectinib compound, including the following steps:

step 1: key intermediate 4 and its synthesis
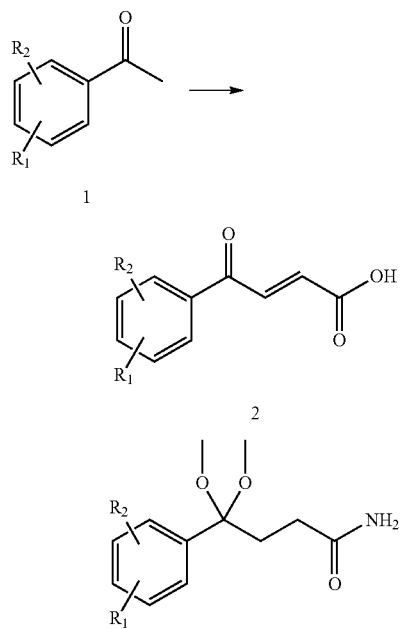
step 2: key intermediate 8 and its synthesis
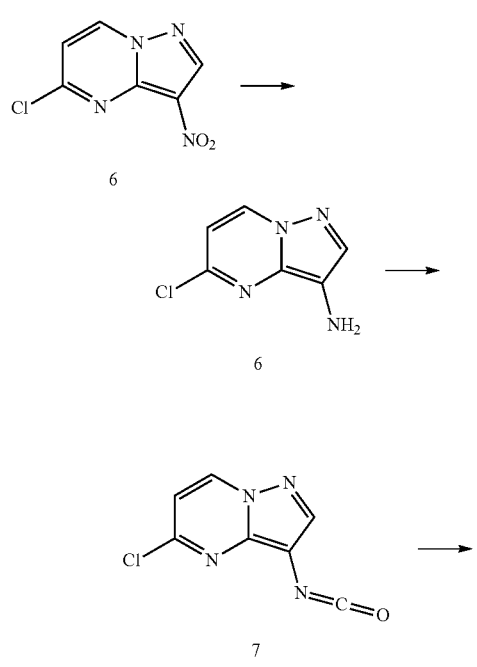
step 3: preparation of halogenated larotrectinib analog 9
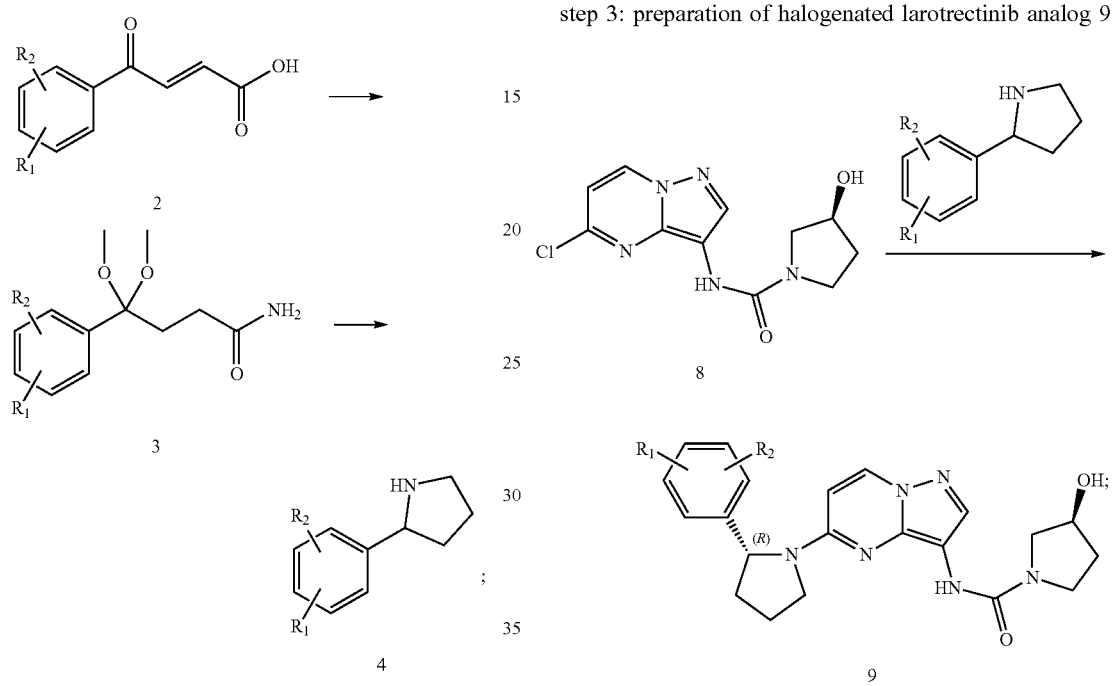
step 4: synthesis of labeled precursor 10
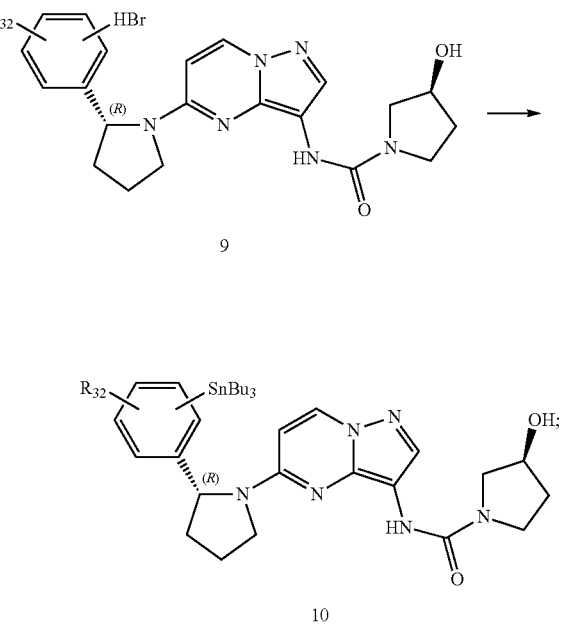

and step 5: synthesis of target product

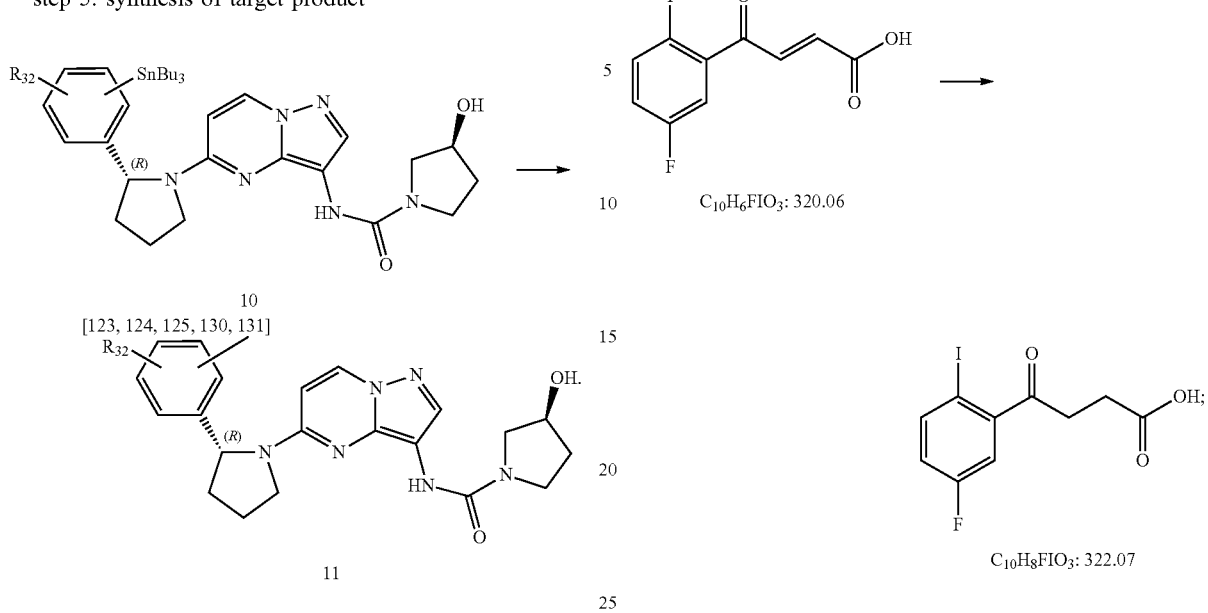

In structural formula 1 of the raw materials used in step 1, $R_1$ and $R_2$ are H, F, Cl, Br or I, respectively.

The key intermediate 4 in step 1 includes the following compounds: 2-(5-fluoro-2-iodophenyl)pyrrolidine, 2-(2-fluoro-5-iodophenyl)pyrrolidine, 2-(2,5-diiodophenyl)pyrrolidine, 2-(2,5-dibromophenyl)pyrrolidine, 2-(2-bromo-4-fluorophenyl)pyrrolidine, 2-(3-bromo-4-fluorophenyl) pyrrolidine, 2-(4-Bromo-3-fluorophenyl)pyrrolidine, and 2-(3-fluoro-5-iodophenyl)pyrrolidine.

The synthesis of 2-(5-fluoro-2-iodophenyl)pyrrolidine includes the following methods:

(11) synthesis of (E)-4-(5-fluoro-2-iodophenyl)-4-oxobut-2-enoic acid, following the reaction formula as follows:

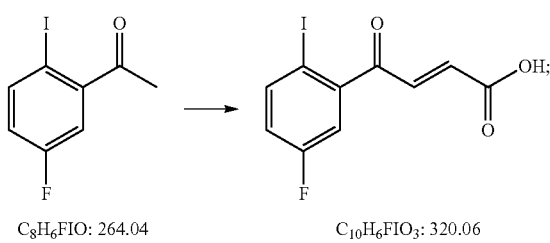

(12) synthesis of 4-(5-fluoro-2-iodophenyl)-4-oxobutanoic acid, following the reaction formula as follows:

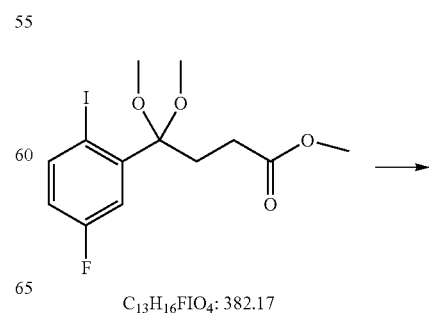

(13) synthesis of methyl 4-(5-fluoro-2-iodophenyl)-4,4-dimethoxybutanoate, following the reaction formula as follows:

(14) synthesis of 4-(5-fluoro-2-iodophenyl)-4-oxobutanamide, following the reaction formula as follows:

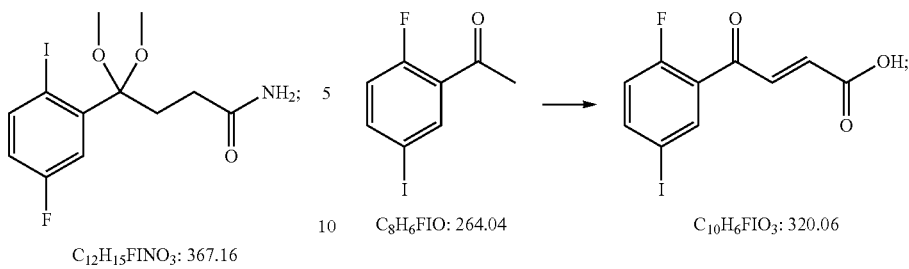

(15) synthesis of 5-(5-fluoro-2-iodophenyl)-3,4-dihydro-2H-pyrrole, following the reaction formula as follows:

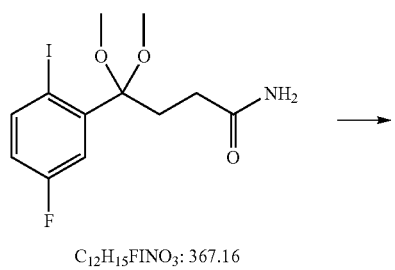

(16) synthesis of 2-(5-fluoro-2-iodophenyl)pyrrolidine, following the reaction formula as follows:

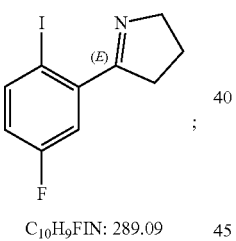

The synthesis of 2-(2-fluoro-5-iodophenyl)pyrrolidine includes the following methods:

(21) synthesis of (E)-4-(2-fluoro-5-iodophenyl)-4-oxobut-2-enoic acid, following the reaction formula as follows:

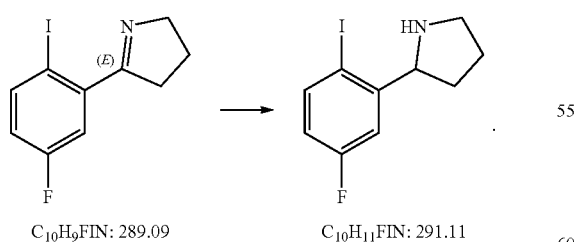

(22) synthesis of 4-(2-fluoro-5-iodophenyl)-4-oxobutanoic acid, following the reaction formula as follows:

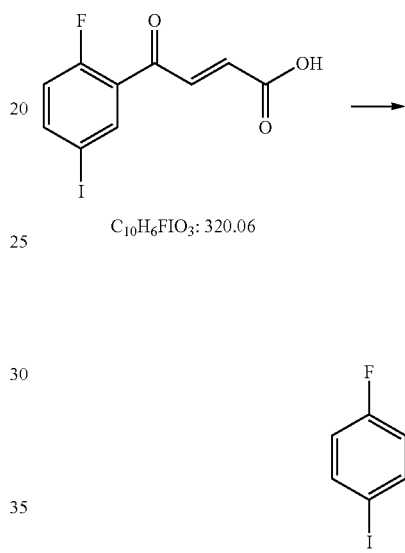

(23) synthesis of methyl 4-(2-fluoro-5-iodophenyl)-4-oxobutanoate, following the reaction formula as follows:

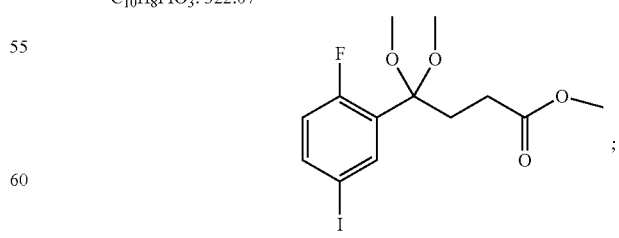

(24) synthesis of 4-(2-fluoro-5-iodophenyl)-4-oxobutanamide, following the reaction formula as follows:

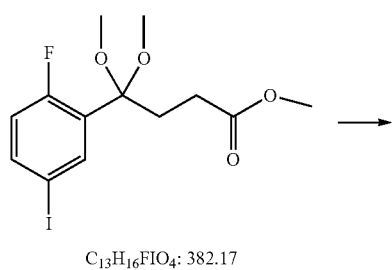

C$_{13}$H$_{16}$FIO$_4$: 382.17

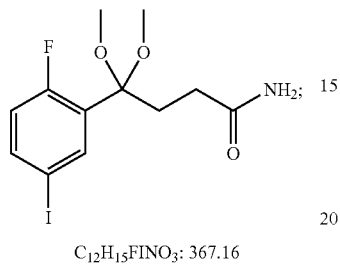

C$_{12}$H$_{15}$FINO$_3$: 367.16

(25) synthesis of 5-(2-fluoro-5-iodophenyl)-3,4-dihydro-2H-pyrrole, following the reaction formula as follows:

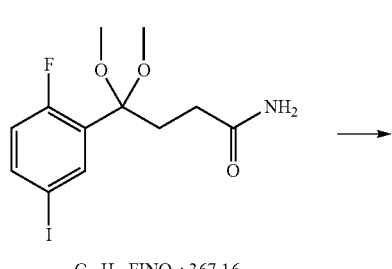

C$_{12}$H$_{15}$FINO$_3$: 367.16

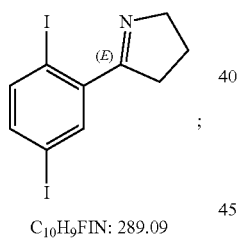

C$_{10}$H$_9$FIN: 289.09

(26) synthesis of 2-(5-fluoro-2-iodophenyl)pyrrolidine, following the reaction formula as follows:

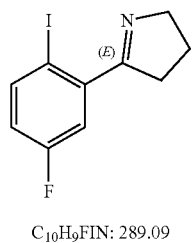

C$_{10}$H$_9$FIN: 289.09

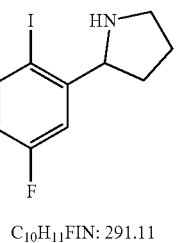

C$_{10}$H$_{11}$FIN: 291.11

The synthesis of 2-(2,5-diiodophenyl)pyrrolidine includes the following methods:

(31) synthesis of (E)-4-(2,5-diiodophenyl)-4-oxobut-2-enoic acid, following the reaction formula as follows:

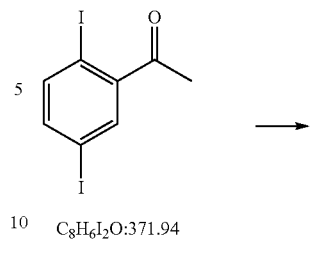

C$_8$H$_6$I$_2$O: 371.94

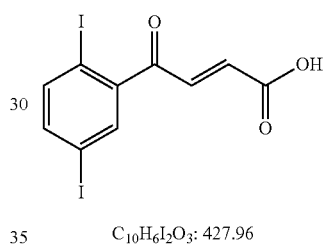

C$_{10}$H$_6$I$_2$O$_3$: 427.96

(32) synthesis of 4-(2,5-diiodophenyl)-4-oxobutanoic acid, following the reaction formula as follows:

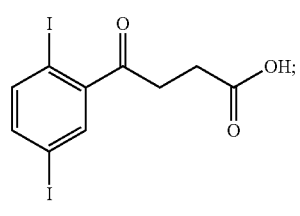

C$_{10}$H$_6$I$_2$O$_3$: 427.96

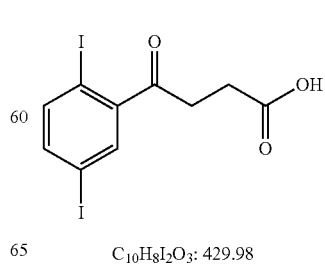

C$_{10}$H$_8$I$_2$O$_3$: 429.98

(33) synthesis of methyl 4-(2,5-diiodophenyl)-4-oxobutanoate, following the reaction formula as follows:

C$_{10}$H$_8$I$_2$O$_3$: 429.98

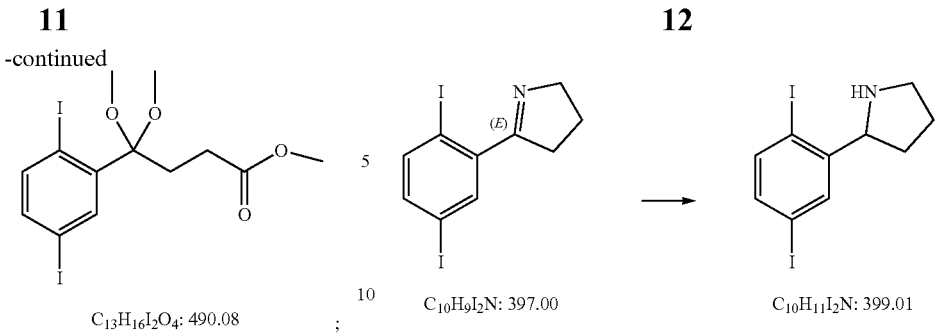

(34) synthesis of 4-(2,5-diiodophenyl)-4-oxobutanamide, following the reaction formula as follows:

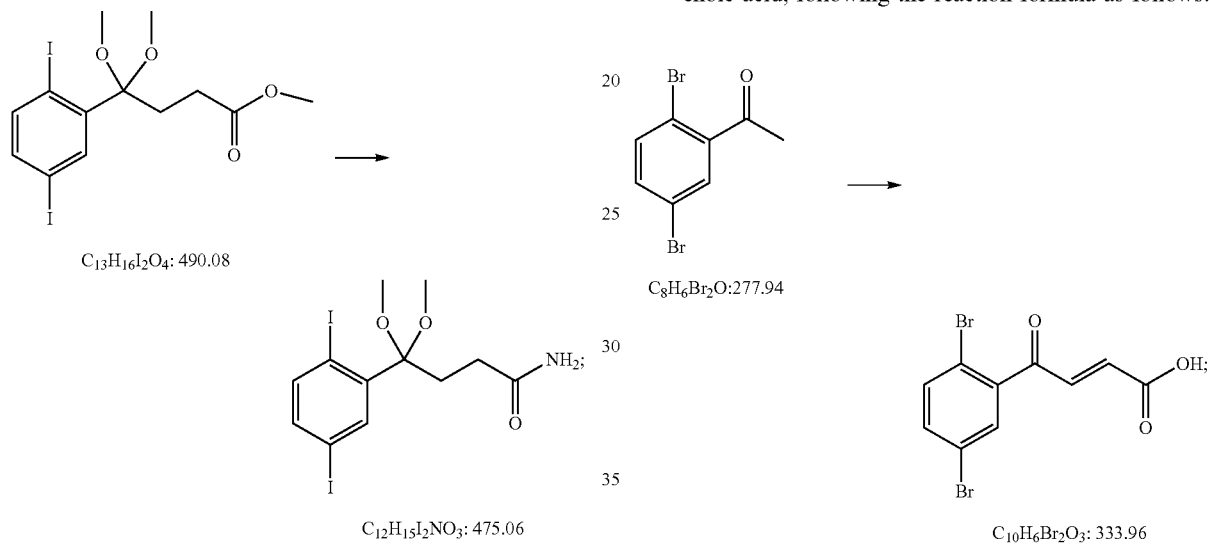

(35) synthesis of 5-(2,5-iodophenyl)-3,4-dihydro-2H-pyrrole, following the reaction formula as follows:

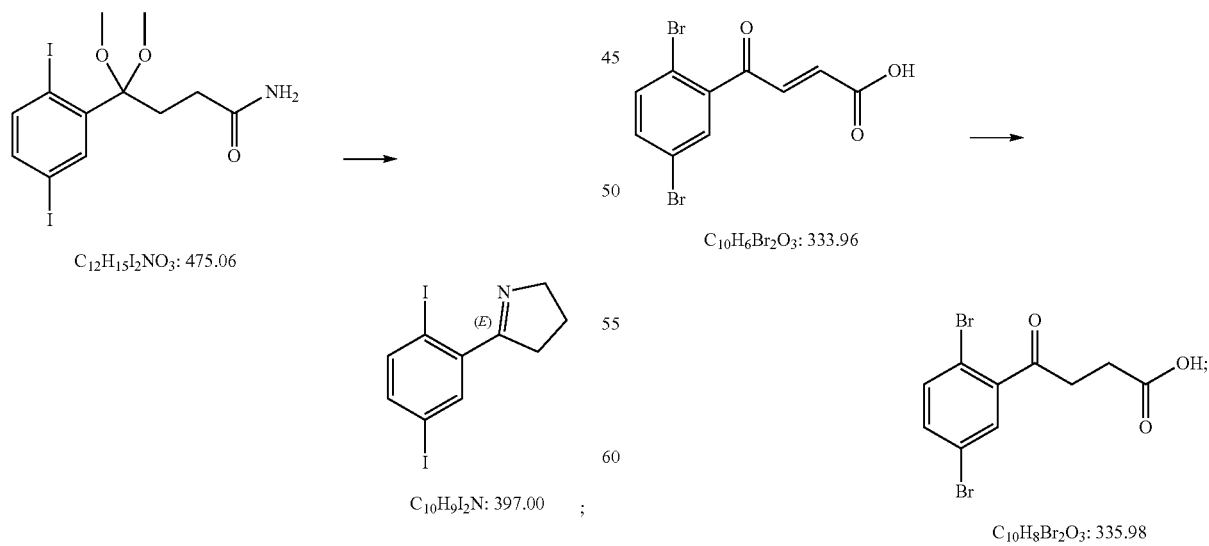

and

(36) synthesis of 2-(2,5-diiodophenyl)pyrrolidine, following the reaction formula as follows:

The synthesis of 2-(2,5-dibromophenyl)pyrrolidine includes the following methods:

(41) synthesis of (E)-4-(2,5-dibromophenyl)-4-oxobut-2-enoic acid, following the reaction formula as follows:

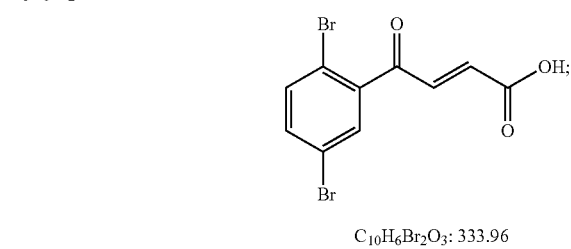

(42) synthesis of 4-(2,5-dibromophenyl)-4-oxobutanoic acid, following the reaction formula as follows:

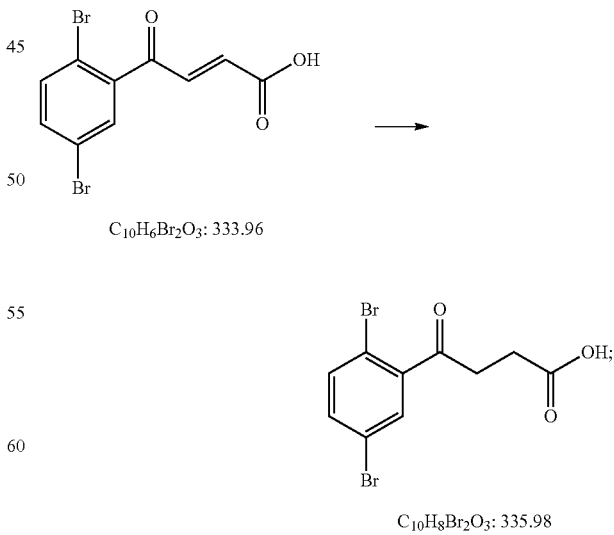

(43) synthesis of methyl 4-(2,5-dibromophenyl)-4-oxobutanoate, following the reaction formula as follows:

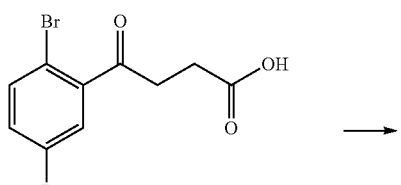

C₁₀H₈Br₂O₃: 335.98

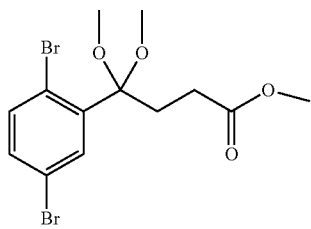

C₁₃H₁₆Br₂O₄: 396.08 ;

(44) synthesis of 4-(2,5-dibromophenyl)-4-oxobutanamide, following the reaction formula as follows:

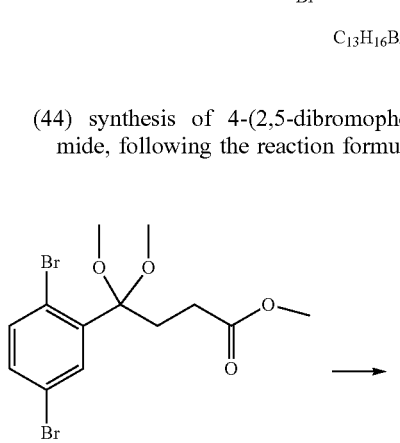

C₁₃H₁₆Br₂O₄: 396.08

C₁₂H₁₆Br₂NO₃: 381.06

(45) synthesis of 5-(2,5-bromophenyl)-3,4-dihydro-2H-pyrrole, following the reaction formula as follows:

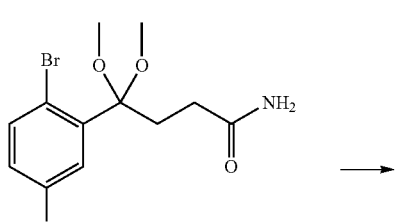

C₁₂H₁₅Br₂NO₃: 381.06

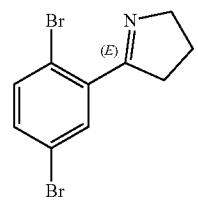

C₁₀H₉Br₂N: 303.00 ;

and

(46) synthesis of 2-(2,5-diiodophenyl)pyrrolidine, following the reaction formula as follows:

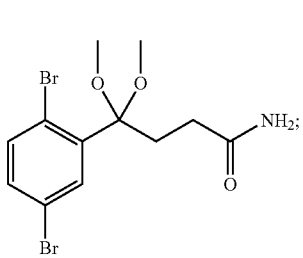

C₁₀H₉Br₂N: 303.00   C₁₀H₁₁Br₂N: 305.01 .

The synthesis of 2-(2-bromo-4-fluorophenyl)pyrrolidine includes the following methods:

(51) synthesis of (E)-4-(2-bromo-4-fluorohenyl)-4-oxobut-2-enoic acid, following the reaction formula as follows:

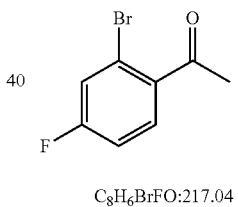

C₈H₆BrFO: 217.04

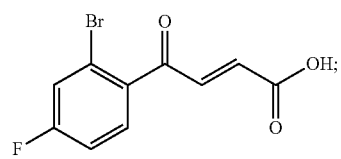

C₁₀H₆BrFO₃: 273.06

(52) synthesis of 4-(2-bromo-4-fluorophenyl)-4-oxobutanoic acid, following the reaction formula as follows:

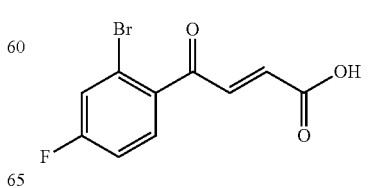

C₁₀H₆BrFO₃: 273.06

-continued

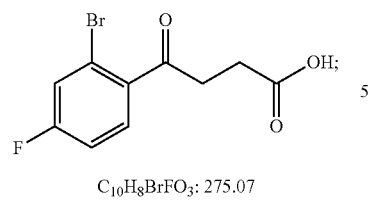

C₁₀H₈BrFO₃: 275.07

(53) synthesis of methyl 4-(2-bromo-4-fluorophenyl)-4-oxobutanoate, following the reaction formula as follows:

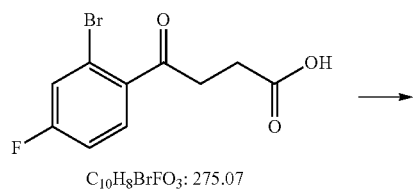

C₁₀H₈BrFO₃: 275.07

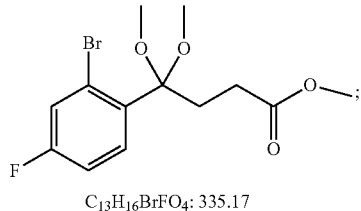

C₁₃H₁₆BrFO₄: 335.17

(54) synthesis of 4-(2-bromo-4-fluorophenyl)-4-oxobutanamide, following the reaction formula as follows:

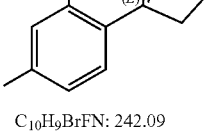

C₁₃H₁₆BrFO₄: 335.17

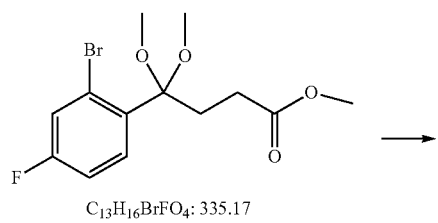

C₁₂H₁₂BrFNO₃: 320.16

(55) synthesis of 5-(2-bromo-4-fluorophenyl)-3,4-dihydro-2H-pyrrole, following the reaction formula as follows:

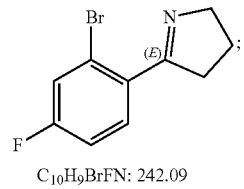

C₁₂H₁₅BrFNO₃: 320.16

[pyrrole structure]

C₁₀H₉BrFN: 242.09 and

(56) synthesis of 2-(2-bromo-4-fluorophenyl)pyrrolidine, following the reaction formula as follows:

[pyrrole structure]

C₁₀H₉BrFN: 242.09

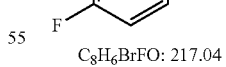

C₁₀H₁₁BrFN: 244.11

The synthesis of 2-(3-bromo-4-fluorophenyl)pyrrolidine includes the following methods:

(61) synthesis of (E)-4-(3-bromo-4-fluorohenyl)-4-oxobut-2-enoic acid, following the reaction formula as follows:

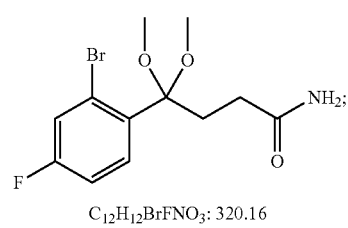

C₈H₆BrFO: 217.04

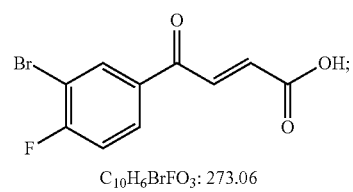

C₁₀H₆BrFO₃: 273.06

(62) synthesis of 4-(3-bromo-4-fluorophenyl)-4-oxobutanoic acid, following the reaction formula as follows:

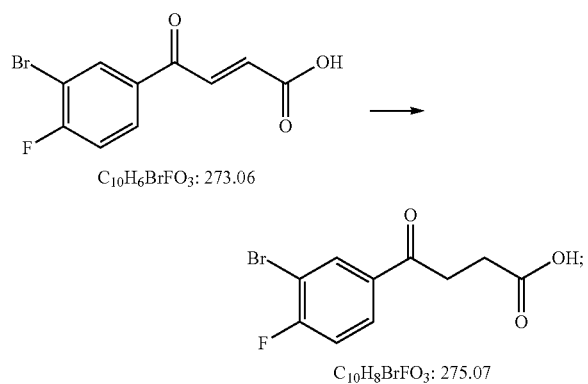

(63) synthesis of methyl 4-(3-bromo-4-fluorophenyl)-4-oxobutanoate, following the reaction formula as follows:

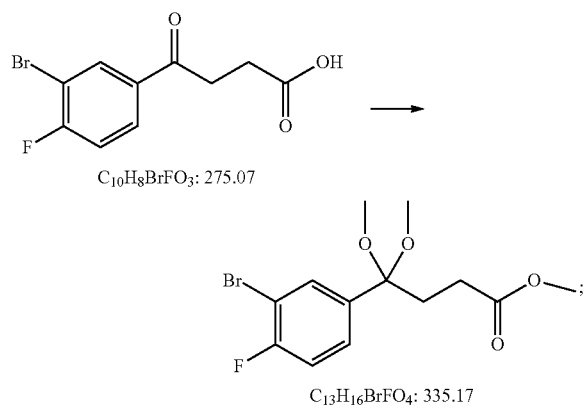

(64) synthesis of 4-(3-bromo-4-fluorophenyl)-4-oxobutanamide, following the reaction formula as follows:

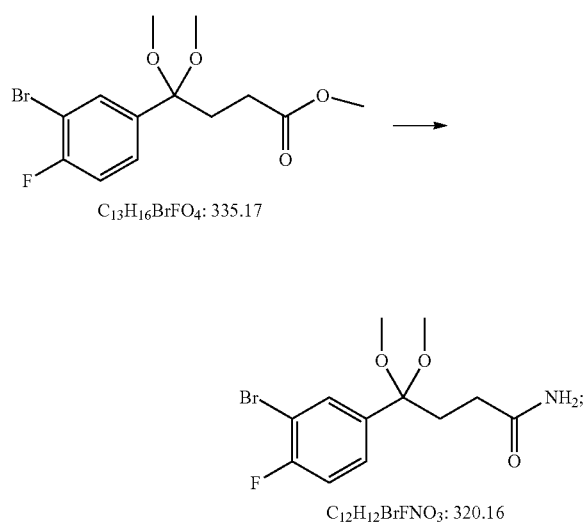 [SMILES: COC(=O)CCC(OC)(OC)c1ccc(F)c(Br)c1 ; COC(CCC(N)=O)(OC)c1ccc(F)c(Br)c1]

(65) synthesis of 5-(3-fluoro-4-iodophenyl)-3,4-dihydro-2H-pyrrole, following the reaction formula as follows:

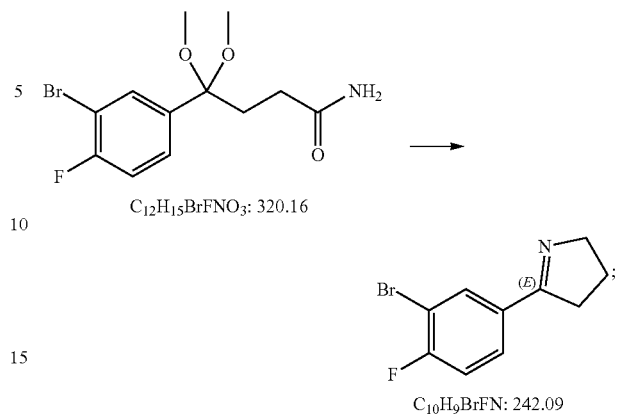

and

(66) synthesis of 2-(3-bromo-4-fluorophenyl)pyrrolidine, following the reaction formula as follows:

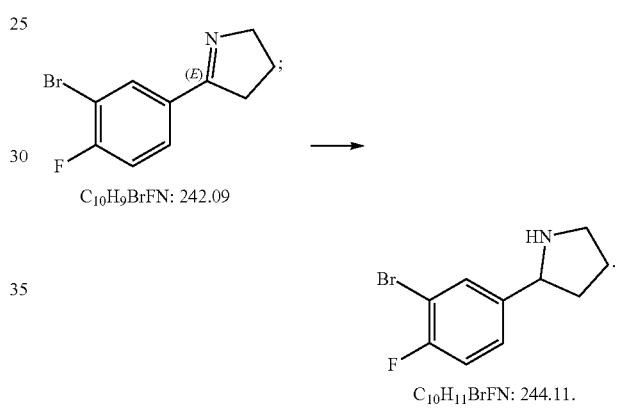

The synthesis of 2-(4-bromo-3-fluorophenyl)pyrrolidine includes the following methods:

(71) synthesis of (E)-4-(4-bromo-3-fluorohenyl)-4-oxobut-2-enoic acid, following the reaction formula as follows:

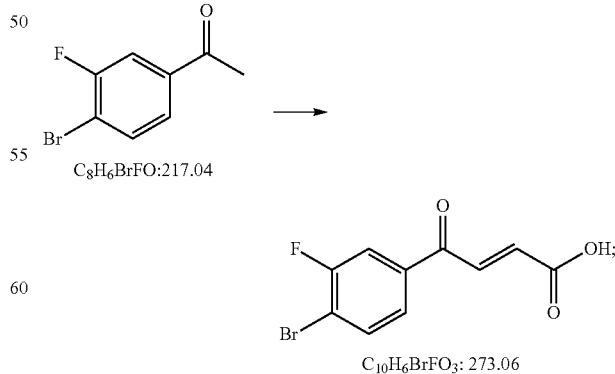

(72) synthesis of 4-(4-bromo-3-fluorophenyl)-4-oxobutanoic acid, following the reaction formula as follows:

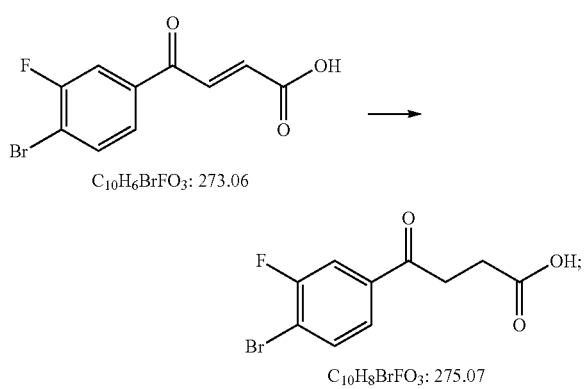

(73) synthesis of methyl 4-(4-bromo-3-fluorophenyl)-4-oxobutanoate, following the reaction formula as follows:

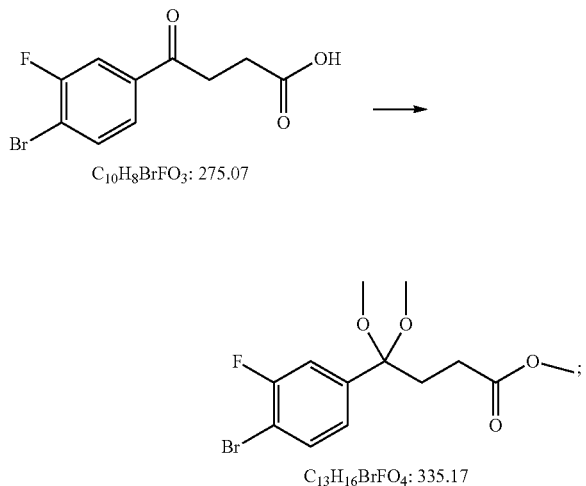 [SMILES: O=C(O)CCC(=O)c1ccc(Br)c(F)c1 ; COC(=O)CCC(OC)(OC)c1ccc(Br)c(F)c1]

(74) synthesis of 4-(4-bromo-3-fluorophenyl)-4-oxobutanamide, following the reaction formula as follows:

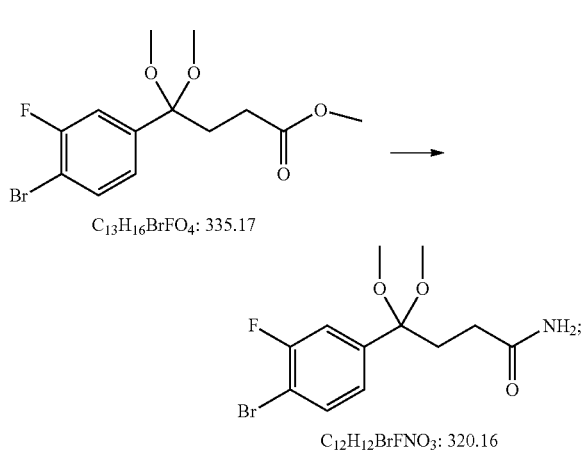

(75) synthesis of 5-(4-fluoro-3-iodophenyl)-3,4-dihydro-2H-pyrrole, following the reaction formula as follows:

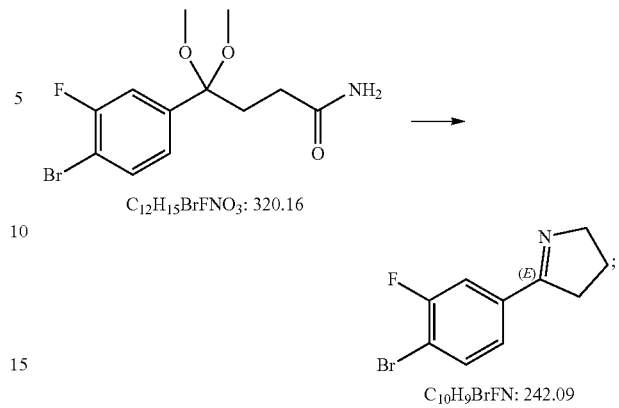

and

(76) synthesis of 2-(4-bromo-3-fluorophenyl)pyrrolidine, following the reaction formula as follows:

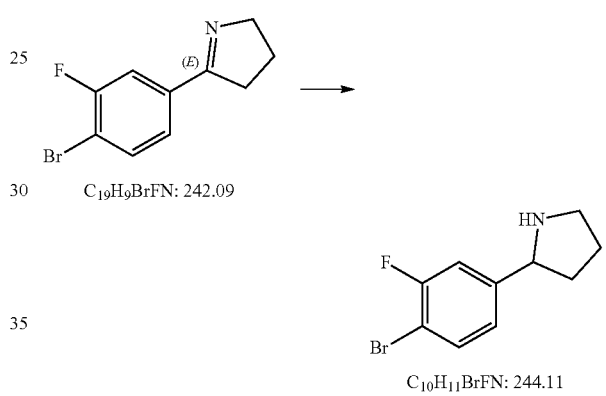

The synthesis of 2-(3-fluoro-5-iodophenyl)pyrrolidine includes the following methods:

(81) synthesis of (E)-4-(3-fluoro-5-iodophenyl)-4-oxobut-2-enoic acid, following the reaction formula as follows:

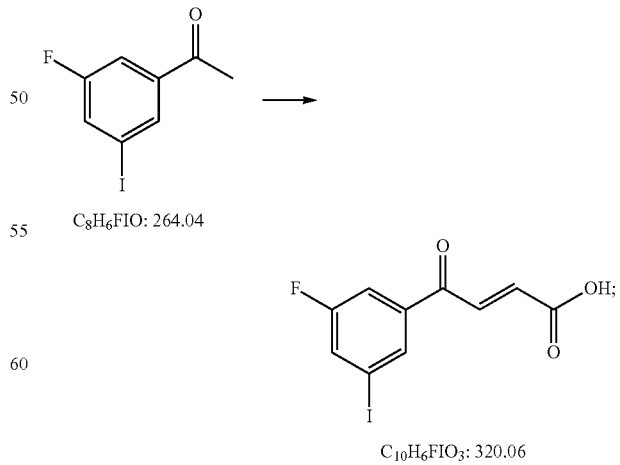

(82) synthesis of 4-(3-fluoro-5-iodophenyl)-4-oxobutanoic acid, following the reaction formula as follows:

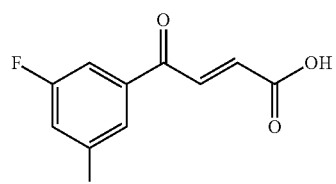

C₁₀H₆FIO₃: 320.06

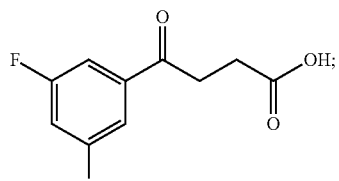

C₁₀H₈FIO₃: 322.07

(83) synthesis of methyl 4-(3-fluoro-5-iodophenyl)-4-oxobutanoate, following the reaction formula as follows:

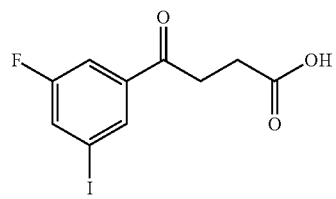

C₁₀H₈FIO₃: 322.07

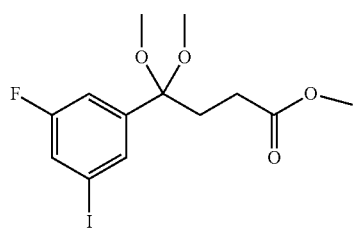

C₁₃H₁₆FIO₄: 382.17

(84) synthesis of 4-(3-fluoro-5-iodophenyl)-4-oxobutanamide, following the reaction formula as follows:

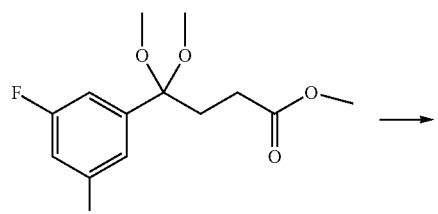

C₁₃H₁₆FIO₄: 382.17

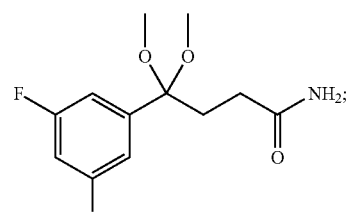

C₁₂H₁₅FINO₃: 367.16

(85) synthesis of 5-(3-fluoro-5-iodophenyl)-3,4-dihydro-2H-pyrrole, following the reaction formula as follows:

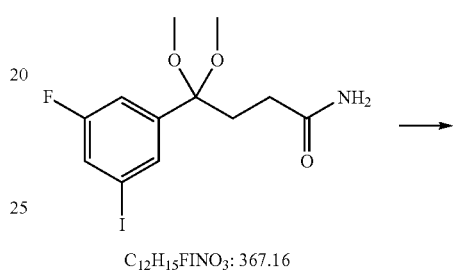

C₁₂H₁₅FINO₃: 367.16

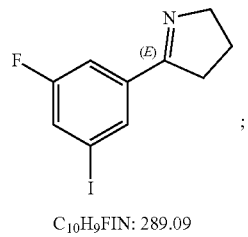

C₁₀H₉FIN: 289.09 and

(86) synthesis of 2-(3-fluoro-5-iodophenyl)pyrrolidine, following the reaction formula as follows:

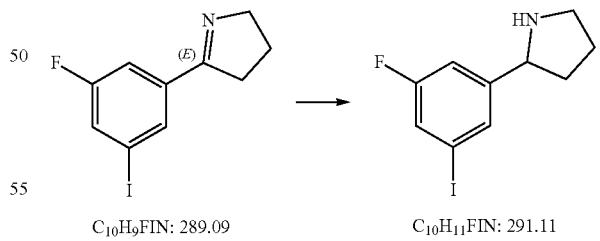

C₁₀H₉FIN: 289.09   C₁₀H₁₁FIN: 291.11

The key intermediate 8 in step 2 includes the following compound: (S)—N-(5-chloropyrazolo[1,5-a]pyrimidin-3-yl)-3-hydroxypyrrolidine-1-carboxamide: the synthesis of (S)—N-(5-chloropyrazolo[1,5-a]pyrimidin-3-yl)-3-hydroxypyrrolidine-1-carboxamide includes the following steps:

(1) synthesis of 5-chloropyrazolo[1,5-a]pyrimidin-3-amine, following the reaction formula as follows:

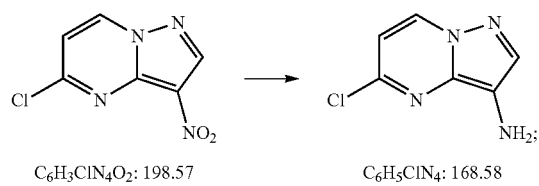 [SMILES: O=[N+]([O-])c1cnn2ccc(Cl)nc12 ; Nc1cnn2ccc(Cl)nc12]

C₆H₃ClN₄O₂: 198.57 → C₆H₅ClN₄: 168.58

(2) synthesis of 5-chloro-3-isocyanatopyrazolo[1,5-a]pyrimidine, following the reaction formula as follows:

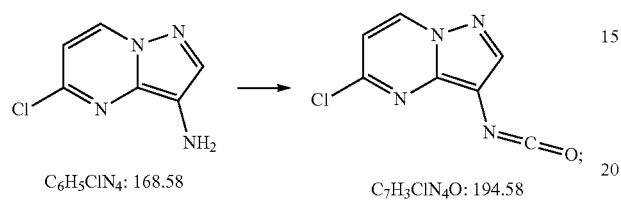

C₆H₅ClN₄: 168.58 → C₇H₃ClN₄O: 194.58 and (3) synthesis of (S)—N-(5-chloropyrazolo[1,5-a]pyrimidin-3-yl)-3-hydroxypyrrolidine-1-carboxamide, following the reaction formula as follows:

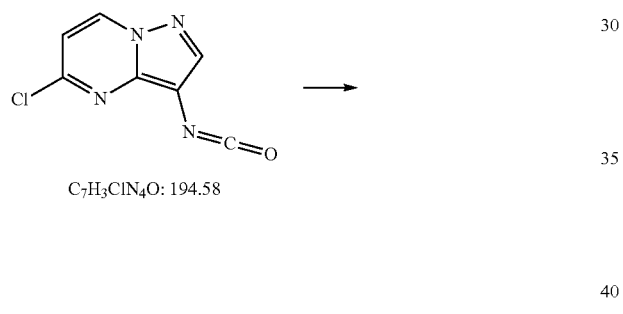

C₇H₃ClN₄O: 194.58

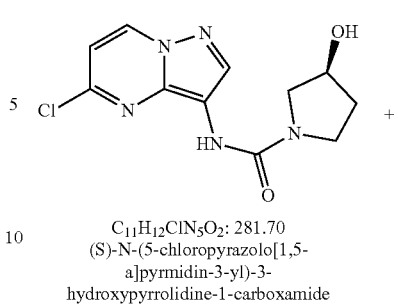

C₁₁H₁₂ClN₅O₂: 281.70
(S)-N-(5-chloropyrazolo[1,5-a]pyrmidin-3-yl)-3-hydroxypyrrolidine-1-carboxamide

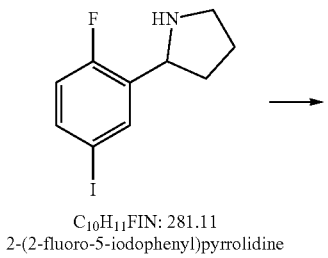

C₁₀H₁₁FIN: 281.11
2-(2-fluoro-5-iodophenyl)pyrrolidine

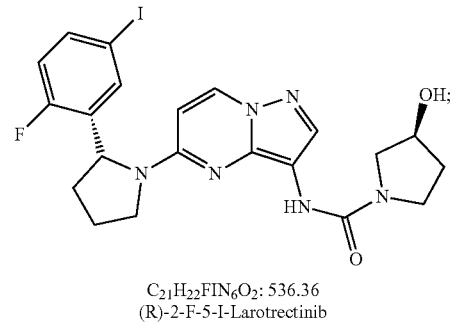

C₂₁H₂₂FIN₆O₂: 536.36
(R)-2-F-5-I-Larotrectinib (2) synthesis of halogenated larotrectinib compound (R)-2-Br-5-Br-LarotrectinibR)-2-Br-5-Br-Larotrectinib, following the reaction formula as follows:

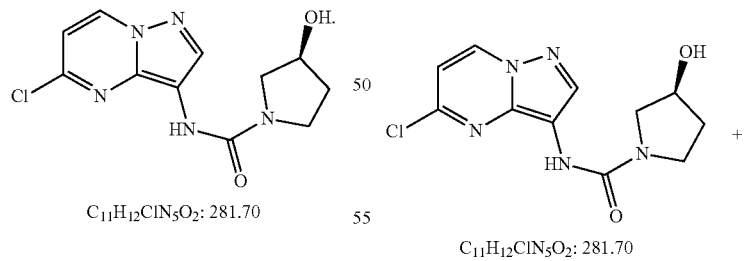

C₁₁H₁₂ClN₅O₂: 281.70    C₁₁H₁₂ClN₅O₂: 281.70

The preparation of the halogenated Larotrectinib analog 9 in step 3 includes: obtaining a racemic halogenated Larotrectinib analog by the reaction of intermediate 4 and intermediate 8, and then separating and purifying the racemic halogenated Larotrectinib analog by chiral LC, thus obtaining the chiral halogenated Larotrectinib analog 9; the preparation specifically includes the following methods:

(1) synthesis of halogenated larotrectinib compound (R)-2-F-5-I-Larotrectinib, following the reaction formula as follows:

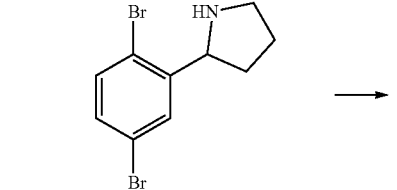

C₁₀H₁₁Br₂N: 305.01
2-(2,5-dibromophenyl)pyrrolidine

-continued

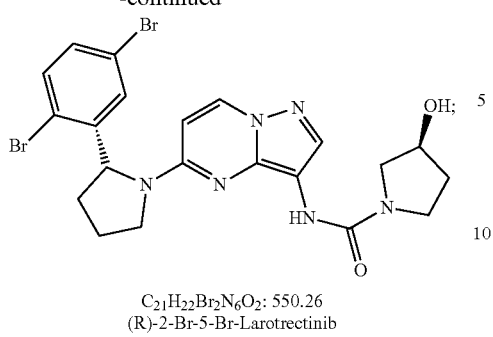

$C_{21}H_{22}Br_2N_6O_2$: 550.26
(R)-2-Br-5-Br-Larotrectinib (3) synthesis of halogenated larotrectinib compound (R)-5-F-2-I-Larotrectinib, following the reaction formula as follows:

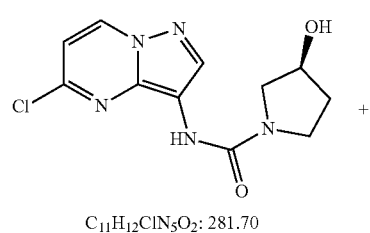

$C_{11}H_{12}ClN_5O_2$: 281.70

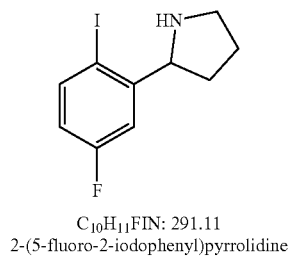

$C_{10}H_{11}FIN$: 291.11
2-(5-fluoro-2-iodophenyl)pyrrolidine

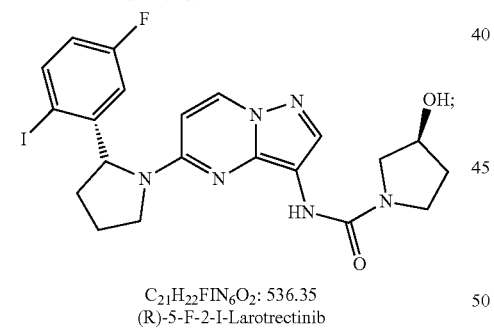

$C_{21}H_{22}FIN_6O_2$: 536.35
(R)-5-F-2-I-Larotrectinib (4) synthesis of halogenated larotrectinib compound (R)-5-I-2-I-Larotrectinib, following the reaction formula as follows:

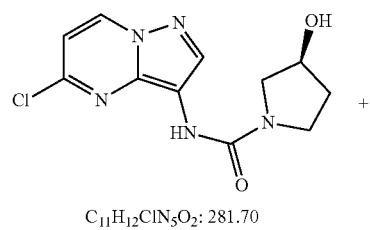

$C_{11}H_{12}ClN_5O_2$: 281.70

-continued

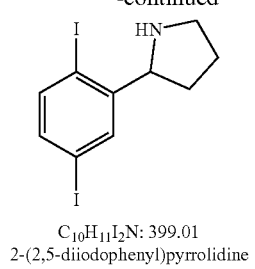

$C_{10}H_{11}I_2N$: 399.01
2-(2,5-diiodophenyl)pyrrolidine

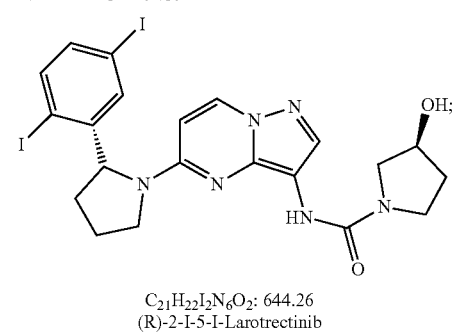

$C_{21}H_{22}I_2N_6O_2$: 644.26
(R)-2-I-5-I-Larotrectinib (5) synthesis of halogenated larotrectinib compound (R)-4-F-2-Br-Larotrectinib, following the reaction formula as follows:

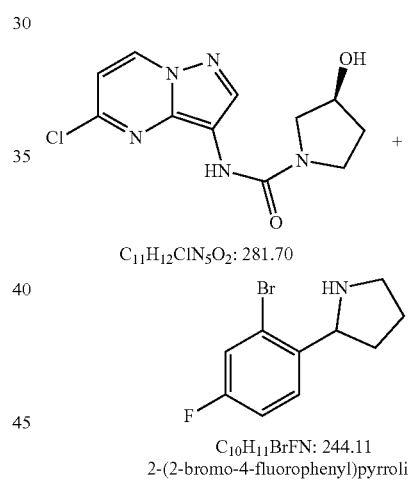

$C_{11}H_{12}ClN_5O_2$: 281.70

$C_{10}H_{11}BrFN$: 244.11
2-(2-bromo-4-fluorophenyl)pyrrolidine

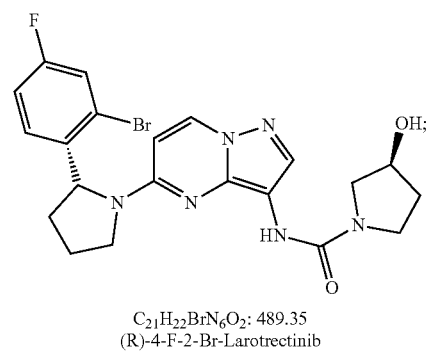

$C_{21}H_{22}BrN_6O_2$: 489.35
(R)-4-F-2-Br-Larotrectinib (6) synthesis of halogenated larotrectinib compound (R)-4-F-3-Br-LarotrectinibR)-4-F-2-Br-Larotrectinib, following the reaction formula as follows:

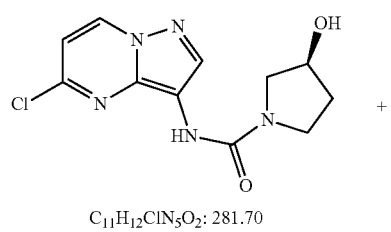

C₁₁H₁₂ClN₅O₂: 281.70

+

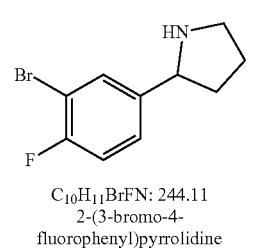

C₁₀H₁₁BrFN: 244.11
2-(3-bromo-4-fluorophenyl)pyrrolidine

⟶

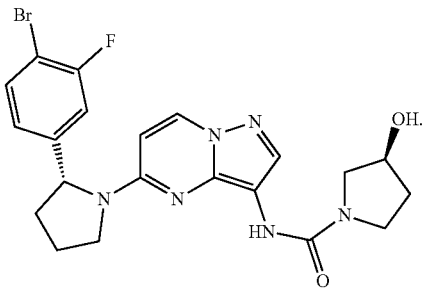

C₂₁H₂₂BrFN₆O₂: 489.35
(R)-4-Br-3-Fr-Larotrectinib

The preparation of the labeled precursor in step 3 includes the following methods:

(1) preparation of labeled precursor (R)-2-fluoro-5-tributyltin-Larotrectinib, following the reaction formula as follows:

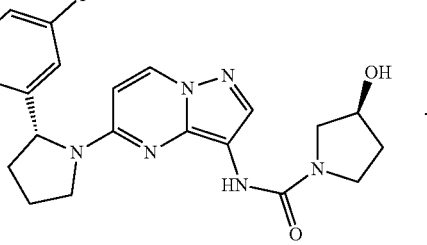

C₂₁H₂₂FIN₆O₂: 536.35
(R)-2-F-5-I-Larotrectinib

⟶

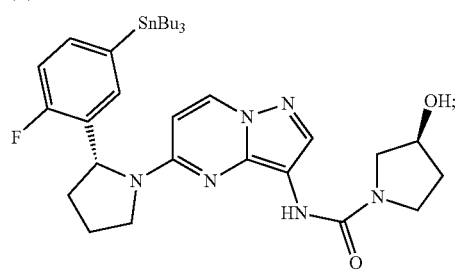

C₃₃H₄₉FIN₆O₂Sn: 699.50
(R)-2-F-5-SnBu₃-Larotrectinib or, and (7) synthesis of halogenated larotrectinib compound (R)-4-Br-3-F-Larotrectinib, following the reaction formula as follows:

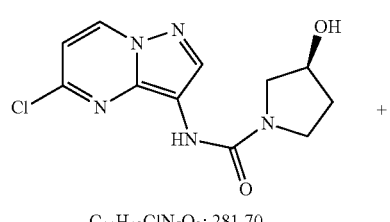

C₁₁H₁₂ClN₅O₂: 281.70

+

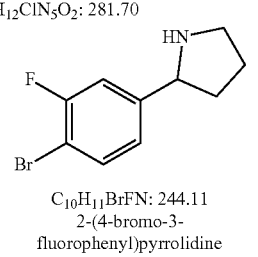

C₁₀H₁₁BrFN: 244.11
2-(4-bromo-3-fluorophenyl)pyrrolidine

⟶

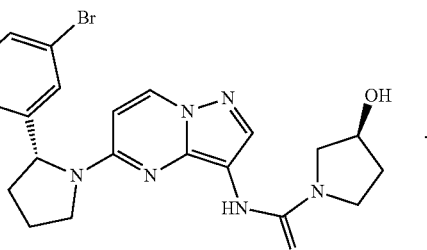

C₂₁H₂₂BrFN₆O₂: 489.35
(R)-2-F-5-Br-Larotrectinib

-continued

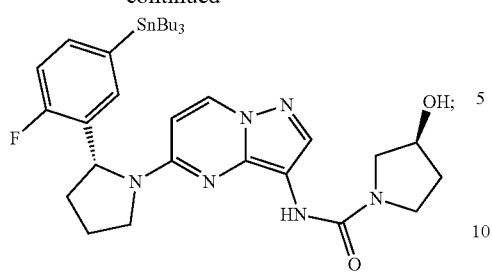

C₃₃H₄₉FN₆O₂Sn: 699.50
(R)-2-F-5-SnBu₃-Larotrectinib (2) preparation of labeled precursor (R)-5-F-2-SnMe₃-Larotrectinib, following the reaction formula as follows:

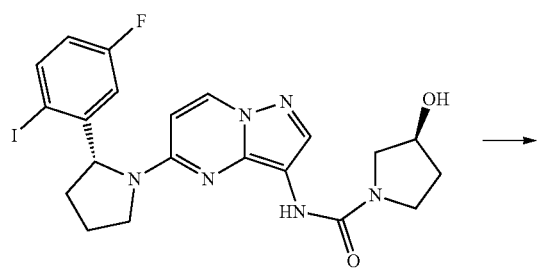

C₂₁H₂₂FIN₆O₂: 536.35
(R)-5-F-2-I-Larotrectinib

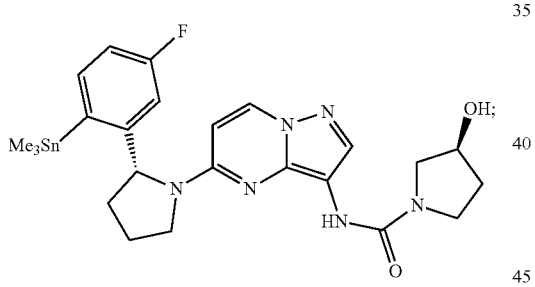

C₂₄H₃₁FN₆O₂Sn: 573.26
(R)-5-F-2-SnMe₃-Larotrectinib (3) preparation of labeled precursor (R)-3-F-5-SnMe₃-Larotrectinib, following the reaction formula as follows:

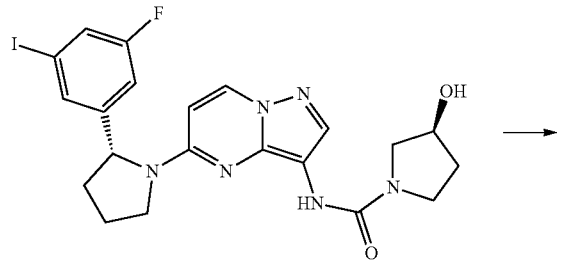

C₂₁H₂₂FIN₆O₂: 536.35
(R)-5-F-2-I-Larotrectinib

-continued

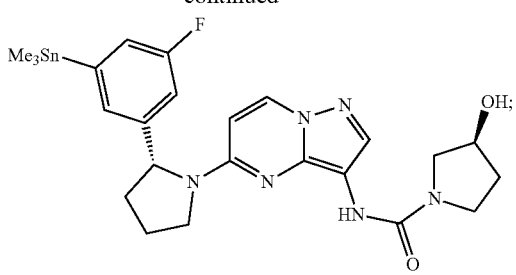

C₂₄H₃₁FN₆O₂Sn: 573.26
(R)-5-F-2-SnMe₃-Larotrectinib (4) preparation of labeled precursor (R)-4-F-2-SnMe₃-Larotrectinib, following the reaction formula as follows:

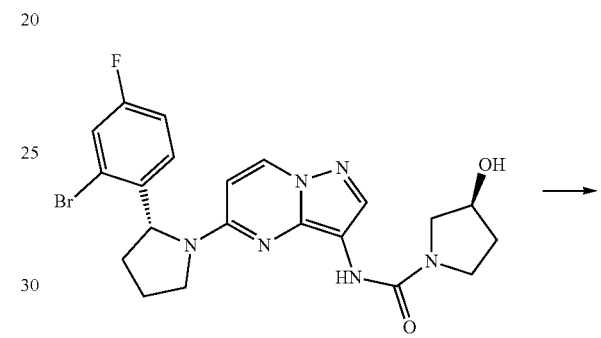

C₂₁H₂₂BrFN₆O₂: 489.35
(R)-4-F-2-Br-Larotrectinib

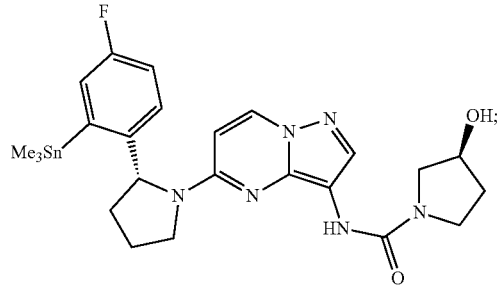

C₂₄H₃₁FN₆O₂Sn: 573.26
(R)-4-F-2-SnMe₃-Larotrectinib (5) preparation of labeled precursor (R)-2,5-bis(SnMe₃)-Larotrectinib, following the reaction formula as follows:

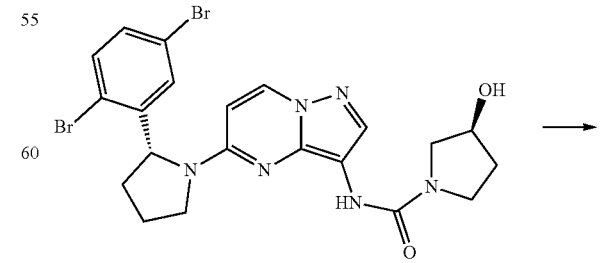

C₂₁H₂₂Br₂N₆O₂: 550.26
(R)-2-Br-5-Br-Larotrectinib

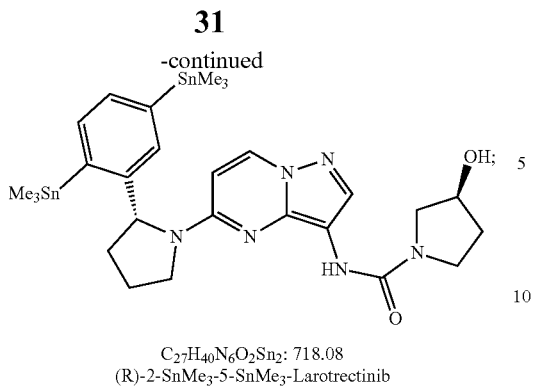

C₂₇H₄₀N₆O₂Sn₂: 718.08
(R)-2-SnMe₃-5-SnMe₃-Larotrectinib (6) preparation of labeled precursor (R)-2-F-4-SnMe₃-Larotrectinib, following the reaction formula as follows:

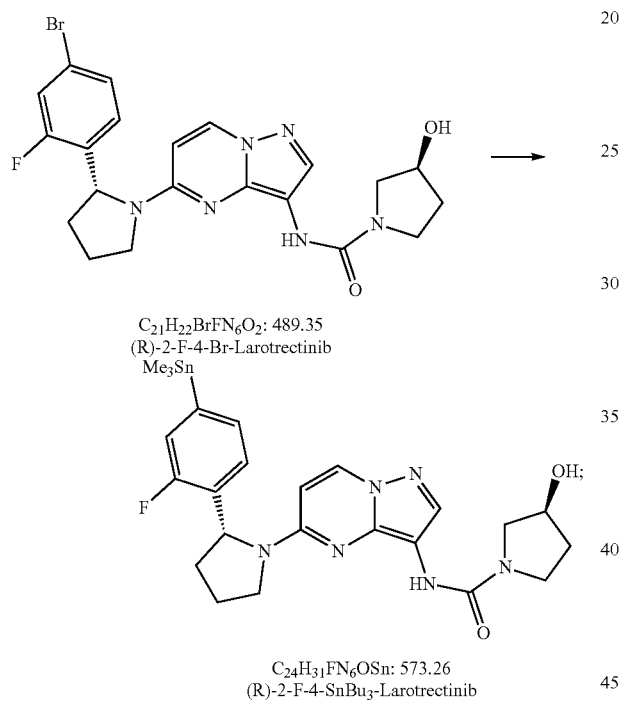

C₂₁H₂₂BrFN₆O₂: 489.35
(R)-2-F-4-Br-Larotrectinib

C₂₄H₃₁FN₆OSn: 573.26
(R)-2-F-4-SnBu₃-Larotrectinib and (7) preparation of labeled precursor (R)-4-F-3-SnMe₃-Larotrectinib, following the reaction formula as follows:

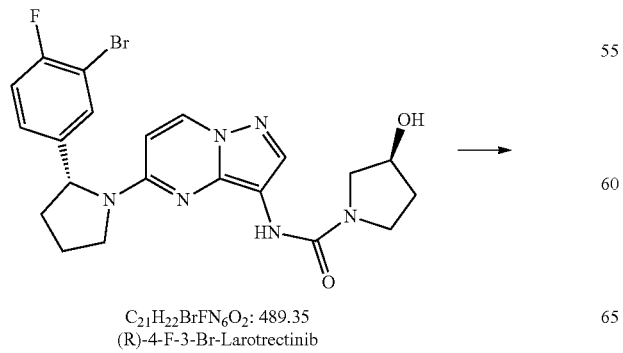

C₂₁H₂₂BrFN₆O₂: 489.35
(R)-4-F-3-Br-Larotrectinib

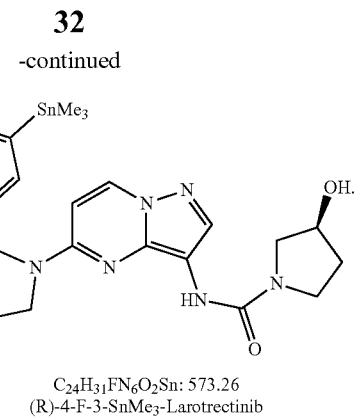

C₂₄H₃₁FN₆O₂Sn: 573.26
(R)-4-F-3-SnMe₃-Larotrectinib

The target product in step 5 includes (R)-2,5-bis-[¹²³, ¹²⁴, ¹²⁵, ¹³⁰, ¹³¹]I-Larotrectinib, (R)-5-F-2-[¹²³, ¹²⁴, ¹²⁵, ¹³⁰, ¹³¹]I-Larotrectinib, (R)-2-F-5-[123, 124, 125, 130, 131]I-Larotrectinib, (R)-4-F-3-[¹²³, ¹²⁴, ¹²⁵, ¹³⁰, ¹³¹]I-Larotrectinib, (R)-2-F-4-[¹²³, ¹²⁴, ¹²⁵, ¹³⁰, ¹³¹]I-Larotrectinib, and (R)-4-F-2-[123, 124, 125, 130, 131]I-Larotrectinib.

The preparation method of the target product is as follows:

(1) preparation of (R)-2,5-bis-[¹²³, ¹²⁴, ¹²⁵, ¹³⁰, ¹³¹]I-Larotrectinib by radioisotope iodine labeling, following the reaction formula as follows:

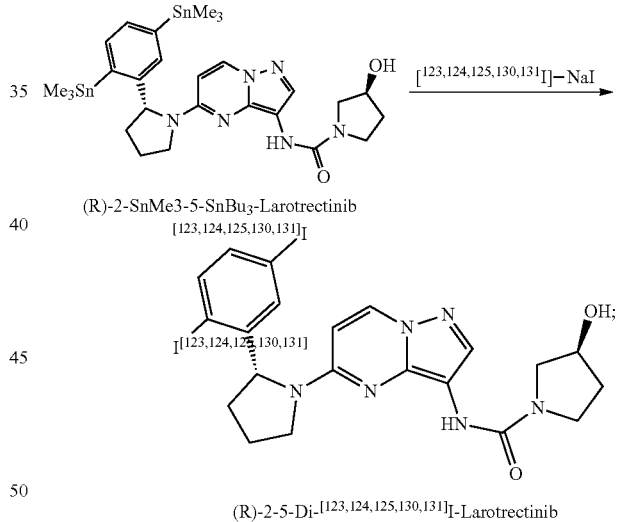

(2) preparation of (R)-5-F-2-[¹²³, ¹²⁴, ¹²⁵, ¹³⁰, ¹³¹]I-Larotrectinib by radioisotope iodine labeling, following the reaction formula as follows:

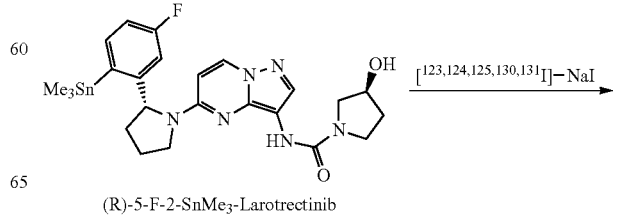

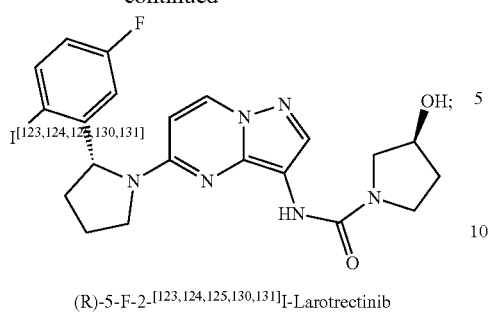

(R)-5-F-2-[123,124,125,130,131]I-Larotrectinib

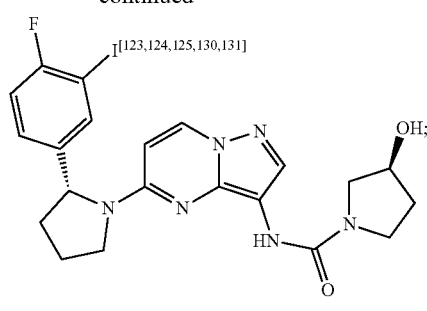

(R)-4-F-3-[123,124,125,130,131]I-Larotrectinib (3) preparation of (R)-2-F-5-[123, 124, 125, 130, 131]I-Larotrectinib by radioisotope iodine labeling, following the reaction formula as follows:

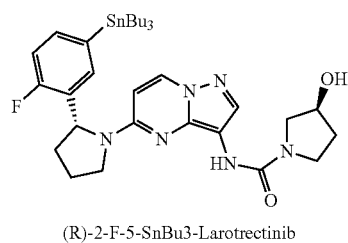

(R)-2-F-5-SnBu3-Larotrectinib

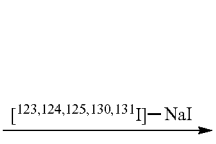

(5) preparation of (R)-2-F-4-[123, 124, 125, 130, 131]I-Larotrectinib by radioisotope iodine labeling, following the reaction formula as follows:

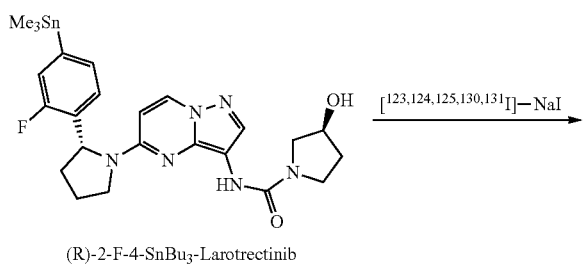

(R)-2-F-4-SnBu3-Larotrectinib

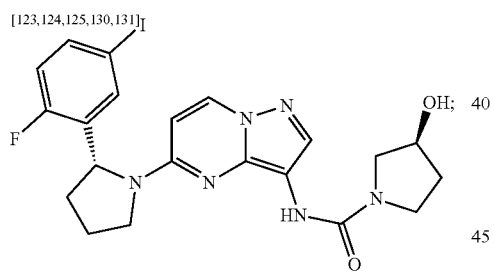

(R)-2-F-5-[123,124,125,130,131]I-Larotrectinib

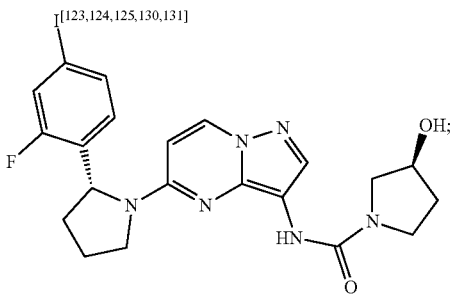

(R)-2-F-4-[123,124,125,130,131]I-Larotrectinib (4) preparation of (R)-4-F-3-[123, 124, 125, 130, 131]I-Larotrectinib by radioisotope iodine labeling, following the reaction formula as follows:

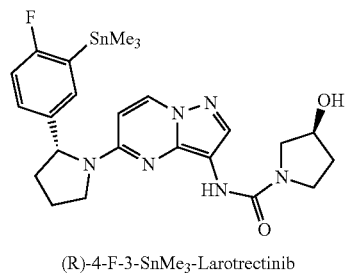

(R)-4-F-3-SnMe3-Larotrectinib (6) preparation of (R)-4-F-2-[123, 124, 125, 130, 131]I-Larotrectinib by radioisotope iodine labeling, following the reaction formula as follows:

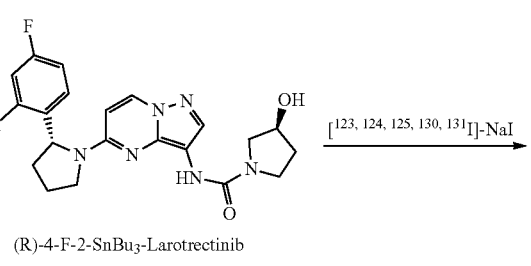

(R)-4-F-2-SnBu3-Larotrectinib

-continued

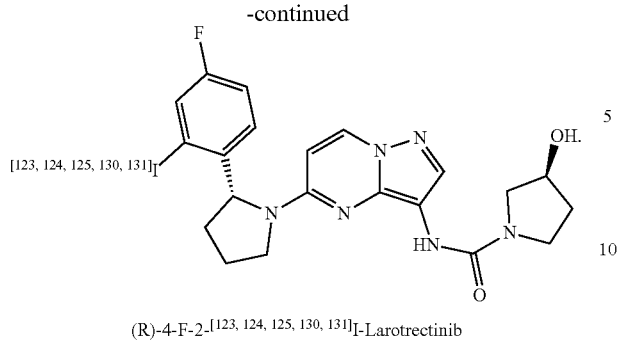

(R)-4-F-2-[123, 124, 125, 130, 131]I-Larotrectinib

Another objective of the invention is to provide application of the pyrazolo[1,5-a]pyrimidine compound, i.e., the radioiodine-substituted Larotrectinib derivative, in the preparation of a radioactive tumor imaging agent. As a radioactive tumor imaging agent precursor, the halogenated Larotrectinib derivative of the invention can be radiochemically synthesized into the corresponding iodine-123, 124, 125, 130, 131 substituted radioactive imaging agent; with TRK as a target, the imaging agent is used for specific tumor imaging. Moreover, the high-energy radioactive iodine of the imaging agent has a synergistic effect on tumor radiotherapy.

Compared with the prior art, the invention has the following beneficial technical effects.

The invention synthesizes a halogenated Larotrectinib compound and its analogues as the radioactive I-labeled precursors. The synthesis method has the following advantages: mature synthesis technology is adopted, reaction conditions are mild, and the operation is simple; radiochemical synthesis takes a short time and only needs 20-25 minutes; the separation is simple and convenient and does not need HPLC, and a Sep-Pak C-18 column can be used to obtain a product with a radiochemical purity of more than 98% and remove the labeled precursor at the same time to obtain a carrier-free product; the radiochemical yield is high, the uncorrected yield can reach 50% to 60%, and the specific radioactivity of the drug is high. In addition, the invention provides an [123, 124, 125, 130, 131]I-Larotrectinib compound labeled with I-123, I-124, I-125, I-130, I-131 and its analogues having the characteristics of emitting positrons or single photons; with the help of PET-CT positron or SPECT single-photon emission tomography technology, the distribution of Larotrectinib compounds and its analogues in vivo and tumors is visually displayed, and a new imaging agent is provided for early tumor diagnosis.

DESCRIPTION OF THE EMBODIMENTS

Unless otherwise stated, terms used in the invention generally have the meanings usually understood by those of ordinary skill in the art.

In the following embodiments, various processes and methods that are not described in detail are conventional methods known in the art. Unless otherwise specified, materials, reagents, devices, instruments, equipment, etc, used in the following examples can be commercially available.

The invention will be described in further detail in conjunction with specific embodiments and with reference to data. It should be understood that the embodiments are only for illustrating the invention, and are not intended to limit the scope of the invention in any way.

Step 1: Synthesis of Key Intermediate 4

Example 1: Synthesis of Key Intermediate 4: Synthesis of 2-(5-fluoro-2-iodophenyl)pyrrolidine Example 1a. Synthesis of (E)-4-(5-fluoro-2-iodophenyl)-4-oxobut-2-enoic acid

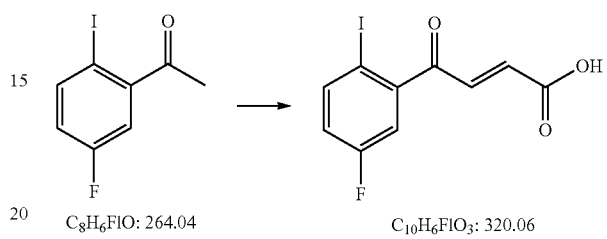

$C_8H_6FIO$: 264.04         $C_{10}H_6FIO_3$: 320.06

5-fluoro-2-iodoacetophenone (39.6 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 5% potassium carbonate aqueous solution (300 mL) was then dosed, and the mixture was extracted twice with ethyl acetate, 200 mL each time; after the aqueous layer was acidified (10% hydrochloric acid, 300 mL), and extraction was carried out twice with ethyl acetate, 200 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with ethyl acetate (300 mL) and rinsed with brine 3 times, 100 mL each time; organic phase was dried over anhydrous sodium sulfate, and the solvent was removed under reduced pressure, thus obtaining the target product (26.89 g, 56%) as a yellow solid with an M.P. of 146° C.

$^1$H NMR (400 MHz, DMSO-d6) δ 12.96 (brs, 1H), 8.00-7.74 (m, 3H), 7.30 (t, 1H, J=8.5 Hz), 6.64 (d, 1H, J=15.4 Hz).

MS (EI) m/z 320(M+).

Example 1b. Synthesis of 4-(5-fluoro-2-iodophenyl)-4-oxobutanoic acid

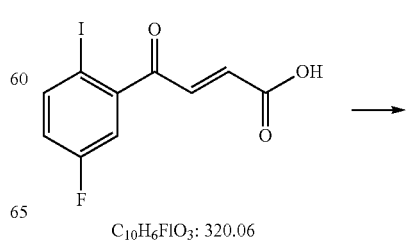

$C_{10}H_6FIO_3$: 320.06

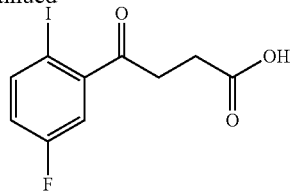

C₁₀H₈FIO₃: 322.07

210 mL of acetic acid, 75 mL of water, and starting material (47.1 g, 147 mmol) were dosed in a 500 mL reaction flask; zinc powder (10.9 g, 166 mmol) was dosed in the reaction mixture in batches within about 1 hour in a stirring way; the mixture was further stirred for 3 hours, reactant was then filtered, the filter cake was rinsed with ethyl acetate (300 mL), the organic phase was rinsed with brine 3 times, 100 mL each time, and dried over anhydrous sodium sulfate, and the solvent was removed under reduced pressure, thus obtaining the target product (29.8 g, 63%) with an M.P. of 152° C.

$^1$H NMR (400 MHz, CDCl$_3$) 12.00 (1H, brs), 7.91-7.71 (3H, m), 3.23 (2H, t, J=6.26), 2.57 (2H, t, J=6.24).

MS (EI) m/z 322 (M+).

Example 1c. Synthesis of methyl 4-(5-fluoro-2-iodophenyl)-4,4-dimethoxybutanoate

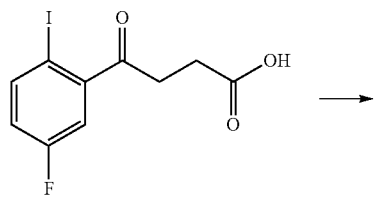

The starting material (32.2 g, 0.1 mol), trimethyl orthoformate (C4H10O3=106.12, 31.84 g, 0.3 mol) and methanol (90 mL) were dosed in a 250 mL reaction flask, and 10 drops of sulfuric acid was then dosed; the mixture was heated to 65° C. to react for 4 hours, TLC tracked the reaction process until the starting material was completely converted, and the solvent was distilled off under reduced pressure. The residue was diluted with isopropyl ether (190 mL), the reaction was quenched with saturated sodium bicarbonate (100 mL), the organic phase was separated, rinsed with brine twice, 120 mL each time, and dried over anhydrous magnesium sulfate, and the solvent was distilled off, thus obtaining the product (32.48 g, 85%) which was directly used in the next step.

$^1$H NMR (400 MHz, CDCl$_3$) 1.29-1.38 (2H, m), 2.25 (2H, t, J=7.2 Hz), 3.11 (3H, s), 3.17 (6H, s), 7.24-7.28 (1H, m), 7.31-7.38 (2H, m), 7.46 (1H, dt, J=8.6, 1.4 Hz);

MS (ESI) m/z 383 [M+H]+.

Example 1d. Synthesis of 4-(5-fluoro-2-iodophenyl)-4-oxobutanamide

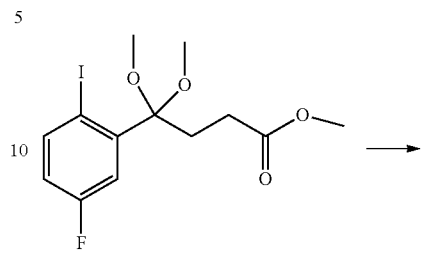

C₁₃H₁₆FIO₄: 382.17

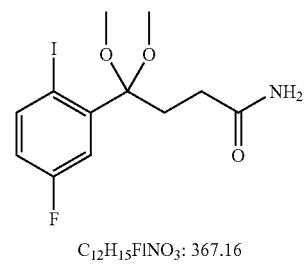

C₁₂H₁₅FINO₃: 367.16

100 mL of methanol was dosed in a 250 mL reaction flask and cooled to below 0° C., and ammonia gas was introduced until the solution was saturated (about 10-12 g); the esterification product (19.1 g, 0.05 mol) from step 1c was dosed in 50 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 1c in the reaction solution basically disappeared, the reaction was stopped, and the solvent was removed under reduced pressure, thus obtaining an oily product which was used directly in the next step of reaction.

MS (ESI) m/z: 368.1(M+H)+.

Example 1e. Synthesis of 5-(5-fluoro-2-iodophenyl)-3,4-dihydro-2H-pyrrole

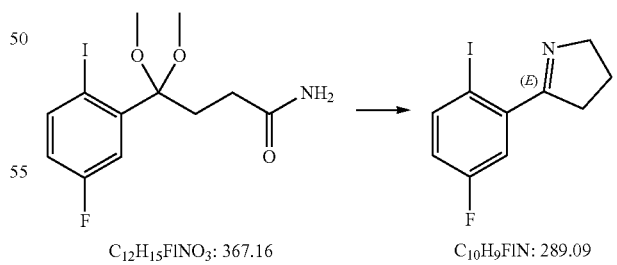

C₁₂H₁₅FINO₃: 367.16    C₁₀H₉FIN: 289.09

Dry tetrahydrofuran (300 mL), the amide (18.36 g, 0.05 mol) from step 1d, and sodium borohydride (29.26 g, 0.77 mol) were dosed in a 500 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, and TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% NaOH to neutrality, extracted with chloroform, dried over anhydrous sodium sulfate, filtered and concentrated under reduced pressure, thus obtaining oily 5-(5-fluoro-2-iodophenyl)-3,4-dihydro-2H-pyrrole (11.27 g, 78%).

The NMR data of the product obtained were as follows:

$^1$H NMR, 400 MHz, CD$_3$OD δ: 7.78 (m, 1H), 7.43-7.34 (m, 2H), 3.54 (m, 2H), 2.12 (dt, J=10.3, 2.0 Hz, 2H), 1.97 (dt, J=15.8, 7.9 Hz, 2H).

$^{13}$C NMR, 100 MHz, CD$_3$OD δ: 176.2, 158.2 (d, J=260.3), 155.0 (d, J=10.3), 124.0 (d, J=3.1), 119.4 (d, J=23.5), 118.4 (d, J=23.5), 62.3, 36.5, 21.0.

Example 1f: Synthesis of 2-(5-fluoro-2-iodophenyl)pyrrolidine

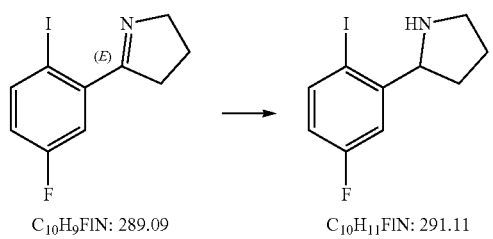 [SMILES: Fc1ccc(I)c(C2=NCCC2)c1 ; Fc1ccc(I)c(C2CCCN2)c1]

C$_{10}$H$_9$FIN: 289.09    C$_{10}$H$_{11}$FIN: 291.11

The oily 5-(5-fluoro-2-iodophenyl)-3,4-dihydro-2H-pyrrole (7.23 g, 0.025 mol) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with NaOH and then extracted with isopropyl ether; the ether layer was dried over anhydrous sodium sulfate overnight and filtered to remove the solvent, thus obtaining a light yellow oily product (6.23 g, 88.3%), which was directly used into next step of reaction.

$^1$H NMR, 400 MHz, CDCl$_3$ δ: 7.29 (m, 1H), 7.02 (m, 1H), 6.96 (m, 1H), 4.09 (t, J=7.8 Hz, 1H), 3.16 (m, 1H), 3.04 (m, 1H), 2.21-2.30 (m, 1H), 1.77-1.95 (m, 3H), 1.57-1.67 (m, 1H).

LC-ESI-MS (m/z) 292[M+H]$^+$.

Example 2: Synthesis of Key Intermediate 4: Synthesis of 2-(2-fluoro-5-iodophenyl)pyrrolidine

Example 2a. Synthesis of (E)-4-(2-fluoro-5-iodophenyl)-4-oxobut-2-enoic acid

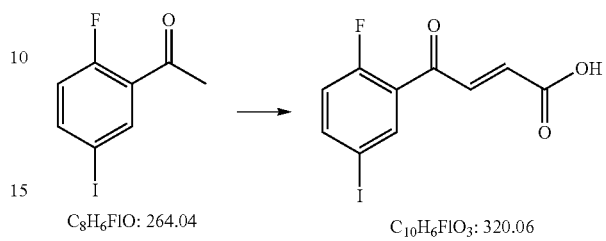

C$_8$H$_6$FIO: 264.04    C$_{10}$H$_6$FIO$_3$: 320.06

2-fluoro-5-iodoacetophenone (39.6 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 5% sodium carbonate aqueous solution (300 mL) was then dosed, and the mixture was extracted twice with isopropyl acetate, 200 mL each time; after the aqueous layer was acidified (10% hydrochloric acid, 300 mL), and extraction was carried out twice with isopropyl acetate, 200 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with isopropyl acetate (300 mL) and rinsed with brine 3 times, 100 mL each time; organic phase was dried over anhydrous sodium sulfate, and the solvent was removed under reduced pressure, thus obtaining the target product (29.28 g, 61%) as a yellow solid with an M.P. of 143° C. to 146° C.

MS (EI) m/z 320 (M+).

Example 2b. Synthesis of 4-(2-fluoro-5-iodophenyl)-4-oxobutanoic acid

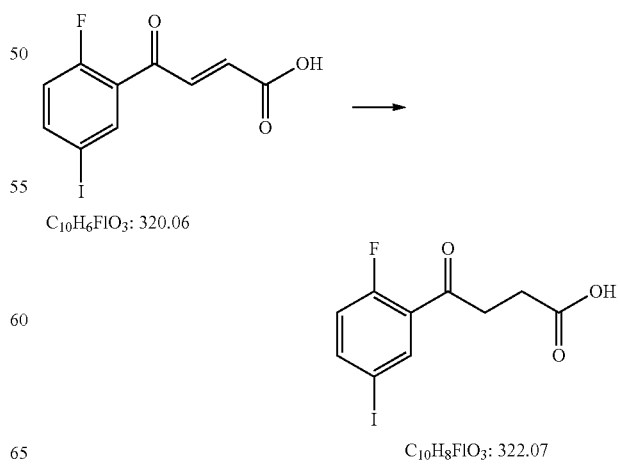

C$_{10}$H$_6$FIO$_3$: 320.06

C$_{10}$H$_8$FIO$_3$: 322.07

210 mL of acetic acid, 75 mL of water, and starting material (37.5 g, 147 mmol) were dosed in a 50 mL reaction flask; zinc powder (10.9 g, 166 mmol) was dosed in the reaction mixture in batches within about 1 hour in a stirring way; the mixture was further stirred for 3 hours, the reactant was then filtered, the filter cake was rinsed with ethyl acetate (300 mL), the organic phase was rinsed with brine (3×100 mL), and dried over anhydrous sodium sulfate, and the solvent was removed under reduced pressure, thus obtaining the target product (27.6 g, 58%) with an M.P. of 148° C. to 150° C.

MS (EI) m/z: 322 (M+).

Example 2c. Synthesis of methyl 4-(2-fluoro-5-iodophenyl)-4-oxobutanoate

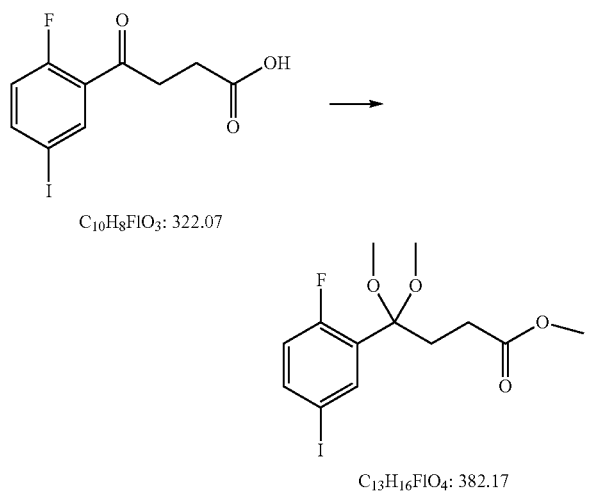

$C_{10}H_8FIO_3$: 322.07

$C_{13}H_{16}FIO_4$: 382.17

The starting material (32.2 g, 0.1 mol), trimethyl orthoformate (C4H10O3=106.12, 31.84 g, 0.3 mol) and methanol (90 mL) were dosed in a 250 mL reaction flask, and 10 drops of sulfuric acid was then dosed; the mixture was heated to 65° C. to react for 4 hours, TLC tracked the reaction process until the starting material was completely converted, and the solvent was distilled off under reduced pressure. The residue was diluted with methyl tert-butyl ether (190 mL), the reaction was quenched with saturated sodium bicarbonate (100 mL), the organic phase was separated, rinsed with brine twice, 120 mL each time, and dried over anhydrous magnesium sulfate, and the solvent was distilled off, thus obtaining the product (32.87 g, 86%), which was directly used in the next step.

MS (ESI) m/z 383 [M+H]+

Example 2d. Synthesis of 4-(2-fluoro-5-iodophenyl)-4-oxobutanamide

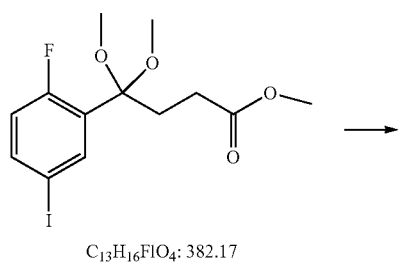

$C_{13}H_{16}FIO_4$: 382.17

-continued

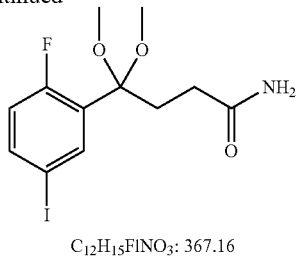

$C_{12}H_{15}FINO_3$: 367.16

100 mL of methanol was dosed in a 250 mL reaction flask and cooled to below 0° C., and ammonia gas was introduced until the solution was saturated (about 10-12 g); the esterification product from step 2c was dosed in 30 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 2c in the reaction solution basically disappeared, the reaction was stopped, and the solvent was removed under reduced pressure, thus obtaining an oily product which was used directly in the next step of reaction.

MS (ESI) m/z: 368.1(M+H)+.

Example 2e. Synthesis of 5-(2-fluoro-5-iodophenyl)-3,4-dihydro-2H-pyrrole

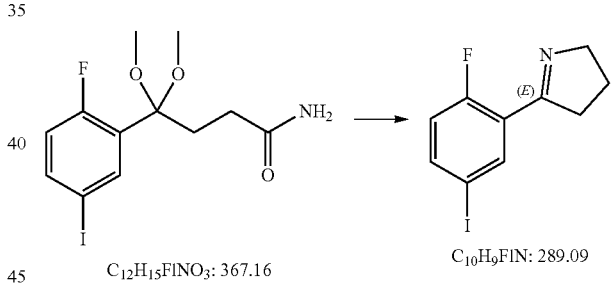

$C_{12}H_{15}FINO_3$: 367.16

$C_{10}H_9FIN$: 289.09

Dry 1,4-dioxane (300 mL), the amide (18.36 g, 0.05 mol) from step 2d, and sodium borohydride (29.26 g, 0.77 mol) were dosed in a 500 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% KOH to neutrality, extracted with dichloromethane, dried over anhydrous sodium sulfate, filtered and concentrated under reduced pressure, thus obtaining oily 5-5-(2-fluoro-5-iodophenyl)-3,4-dihydro-2H-pyrrole (11.7 g, 81%).

MS (EI) m/z 289 (M+).

Example 2f: Synthesis of 2-(5-fluoro-2-iodophenyl)pyrrolidine

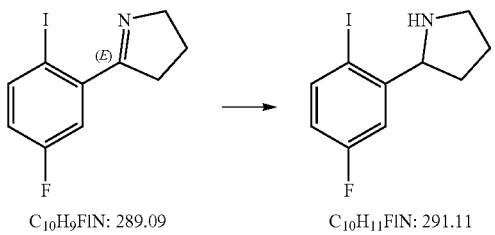 [SMILES: Fc1ccc(I)c(C2=NCCC2)c1 ; Fc1ccc(I)c(C2CCCN2)c1]

The oily 5-(5-fluoro-2-iodophenyl)-3,4-dihydro-2H-pyrrole (7.23 g, 0.025 mol) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with KOH and then extracted with methyl tert-butyl ether; the ether layer was dried over anhydrous sodium sulfate overnight and filtered to remove the solvent, thus obtaining a light yellow oily product, i.e., crude product (6.78 g, 89%), which was directly used into next step of reaction.

LC-ESI-MS (m/z) 292[M+H]$^+$.

Example 3: Synthesis of Key Intermediate 4: Synthesis of 2-(2,5-diiodophenyl)pyrrolidine

Example 3a. Synthesis of (E)-4-(2-iodo-5-iodophenyl)-4-oxobut-2-enoic acid

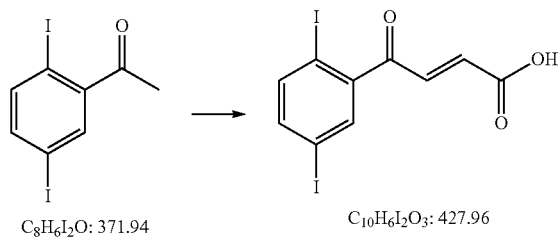

2,5-diiodoacetophenone (55.79 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 10% sodium bicarbonate aqueous solution (300 mL) was then dosed, and the mixture was extracted twice with dichloromethane, 300 mL each time; after the aqueous layer was acidified (10% hydrochloric acid, 300 mL), and extraction was carried out twice with dichloromethane, 300 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with dichloromethane (400 mL) and rinsed with brine 3 times, 100 mL each time; organic phase was dried over anhydrous sodium sulfate, and the solvent was removed under reduced pressure, thus obtaining the target product (31.32 g, 48.8%) as a yellow solid with an M.P. of 138° C. to 142° C.

MS (EI) m/z 427(M+).

Example 3b. Synthesis of 4-(2,5-diiodophenyl)-4-oxobutanoic acid

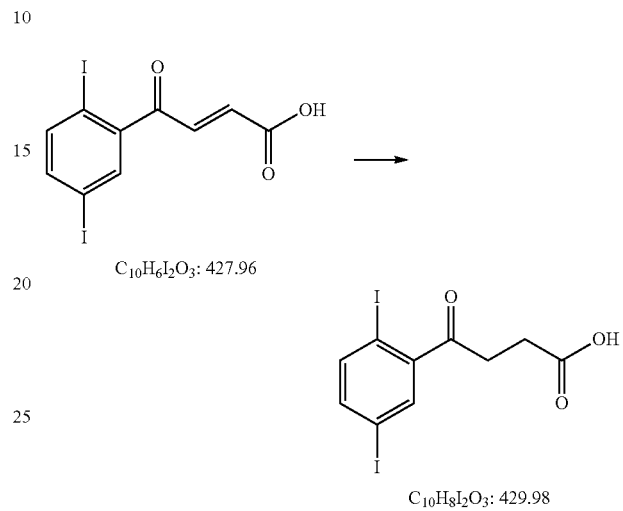

210 mL of acetic acid, 75 mL of water, and starting material (49.09 g, 147 mmol) were dosed in a 500 mL reaction flask; zinc powder (10.9 g, 166 mmol) was dosed in the reaction mixture in batches within about 1 hour in a stirring way; the mixture was further stirred for 3 hours, the reaction mixture was exacted and layered with dichloromethane (300 mL), the organic phase was rinsed with brine (3×100 mL) and dried over anhydrous sodium sulfate, and the solvent was removed under reduced pressure, thus obtaining the target product (34.76 g, 55%) with an M.P. of 146° C. to 148° C.

MS (EI) m/z:430(M+).

Example 3c. Synthesis of methyl 4-(2,5-diiodophenyl)-4-oxobutanoate

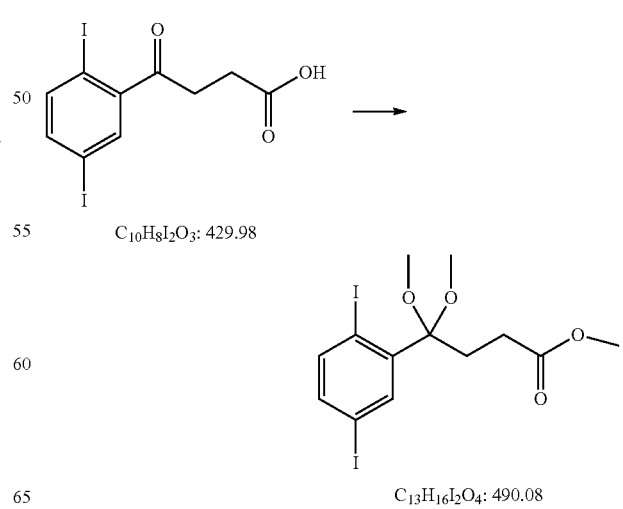

The starting material (43.0 g, 0.1 mol), trimethyl orthoformate (C4H10O3=106.12, 31.84 g, 0.3 mol) and methanol (90 mL) were dosed in a 250 mL reaction flask, and 10 drops of sulfuric acid was then dosed; the mixture was heated to 55° C. to react for 8 hours, TLC tracked the reaction process until the starting material was completely converted, and the solvent was distilled off under reduced pressure. The residue was diluted with methyl tert-butyl ketone (200 mL), the reaction was quenched with saturated potassium bicarbonate (100 mL), the organic phase was separated, rinsed with brine twice, 120 mL each time, and dried over anhydrous magnesium sulfate, and the solvent was distilled off, thus obtaining the product (43.62 g, 89%), which was directly used in the next step.

MS (ESI) m/z: 490, 491.

Example 3d. Synthesis of
4-(2,5-diiodophenyl)-4-oxobutanamide

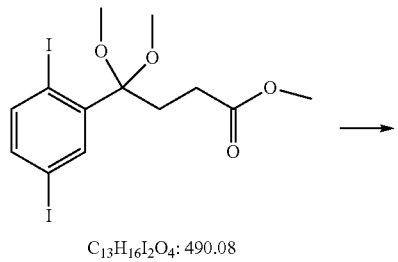

$C_{13}H_{16}I_2O_4$: 490.08

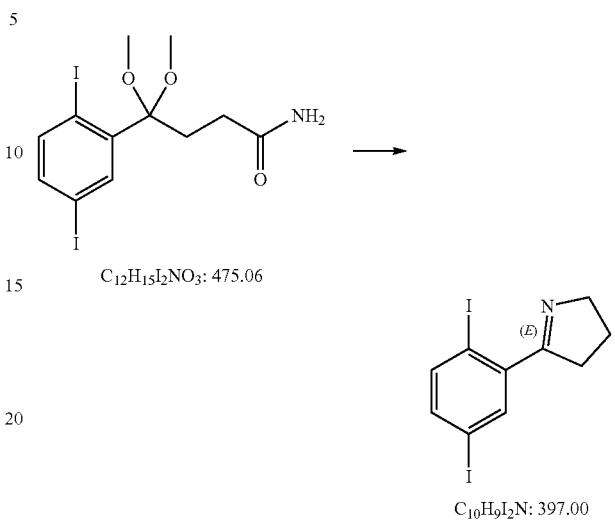

$C_{12}H_{15}I_2NO_3$: 475.06

100 mL of methanol was dosed in a 250 mL reaction flask and cooled to below 0° C., and ammonia gas was introduced until the solution was saturated (about 10-12 g); the esterification product from step 4c was dosed in 30 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 4c in the reaction solution basically disappeared, the reaction was stopped, and the solvent was removed under reduced pressure, thus obtaining an oily product which was used directly in the next step of reaction.

MS (ESI) m/z: 475(M+H)+.

Example 3e. Synthesis of
5-(2,5-iodophenyl)-3,4-dihydro-2H-pyrrole

Dry methyl tert-butyl ether (600 mL), the amide (23.75 g, 0.05 mol) from step 3d, and sodium borohydride (29.26 g, 0.77 mol) were dosed in a 1000 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% sodium bicarbonate to neutrality, extracted with isopropyl acetate, dried over anhydrous sodium sulfate, filtered and concentrated under reduced pressure, thus obtaining oily 5-(2,5-diiodophenyl)-3,4-dihydro-2H-pyrrole (13.5 g, 68%).

The NMR data of the product obtained were as follows:
$^1H$ NMR, 400 MHz, $CD_3OD$ δ:7.78 (m, 1H), 7.43-7.34 (m, 2H), 3.54 (m, 2H), 2.12 (dt, J=10.3, 2.0 Hz, 2H), 1.97 (dt, J=15.8, 7.9 Hz, 2H).
$^{13}C$ NMR, 100 MHz, $CD_3OD$ δ:176.2, 158.2 (d, J=260.3), 155.0 (d, J=10.3), 124.0 (d, J=3.1), 119.4 (d, J=23.5), 118.4 (d, J=23.5), 115.6, 62.3, 36.5, 21.0.

Example 3f: Synthesis of
2-(2,5-diiodophenyl)pyrrolidine

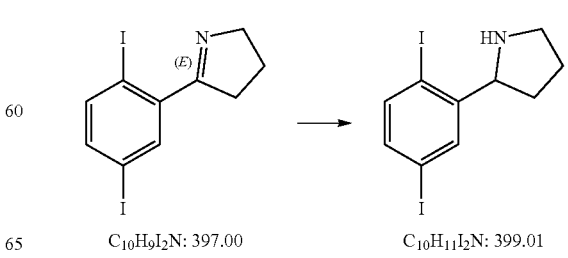

$C_{10}H_9I_2N$: 397.00          $C_{10}H_{11}I_2N$: 399.01

The oily 5-(2,5-diiodophenyl)-3,4-dihydro-2H-pyrrole (9.93 g, 0.025 mmoL) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with $NaHCO_3$ and then extracted with dichloromethane; the organic layer was dried over anhydrous sodium sulfate overnight and filtered to remove the solvent, thus obtaining a light yellow oily product, i.e., crude product (8.87 g, 88.9%), which was directly used into next step of reaction.

The NMR data were as follows:

$^1$H NMR, 400 MHz, $CDCl_3$ δ: 7.29 (m, 1H), 7.02 (m, 1H), 6.96 (m, 1H), 4.09 (t, J=7.8 Hz, 1H), 3.16 (m, 1H), 3.04 (m, 1H), 2.21-2.30 (m, 1H), 1.77-1.95 (m, 3H), 1.57-1.67 (m, 1H).

LC-ESI-MS (m/z): 400[M+H]$^+$, calculated value $C_{10}H_{11}F_2N$: 399.01.

Example 4: Synthesis of Key Intermediate 4: Synthesis of 2-(2,5-dibromophenyl)pyrrolidine Example 4a. Synthesis of (E)-4-(2,5-dibromophenyl)-4-oxobut-2-enoic acid

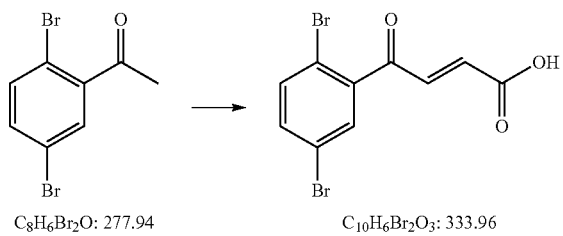

2,5-dibromoacetophenone (41.69 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 10% potassium bicarbonate aqueous solution (300 mL) was then dosed, and the mixture was extracted twice with chloroform, 300 mL each time; after the aqueous layer was acidified (10% hydrochloric acid, 300 mL), and extraction was carried out twice with chloroform, 300 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with chloroform (400 mL) and rinsed with brine 3 times, 100 mL each time; organic phase was dried over anhydrous sodium sulfate, and the solvent was removed under reduced pressure, thus obtaining the target product (26.75 g, 53.4%) as a yellow solid with an M.P. of 141° C. to 144° C.

MS (EI) m/z: 338, 336.

Example 4b. Synthesis of 4-(2,5-dibromophenyl)-4-oxobutanoic acid

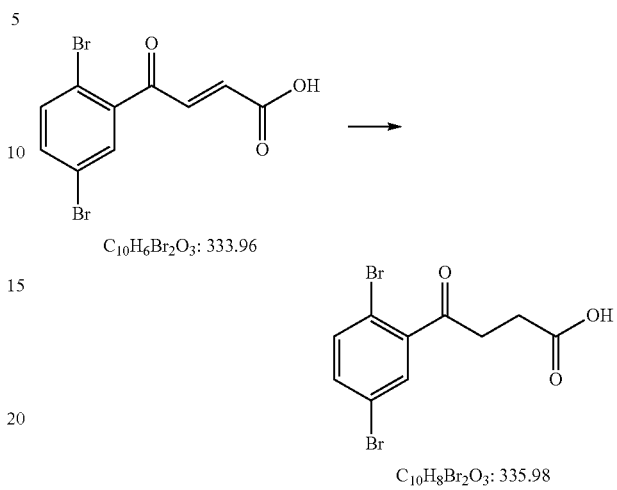

210 mL of acetic acid, 75 mL of water, and starting material (49.09 g, 147 mmol) were dosed in a 500 mL reaction flask; zinc powder (10.9 g, 166 mmol) was dosed in the reaction mixture in batches within about 1 hour in a stirring way; the mixture was further stirred for 3 hours, the reaction mixture was exacted and layered with chloroform (300 mL), the organic phase was rinsed with brine (3×100 mL) and dried over anhydrous sodium sulfate, and the solvent was removed under reduced pressure, thus obtaining the target product (26.07 g, 52.8%) with an M.P. of 145° C. to 148° C.

MS (EI) m/z: 340, 338.

Example 4c. Synthesis of methyl 4-(2,5-dibromophenyl)-4-oxobutanoate

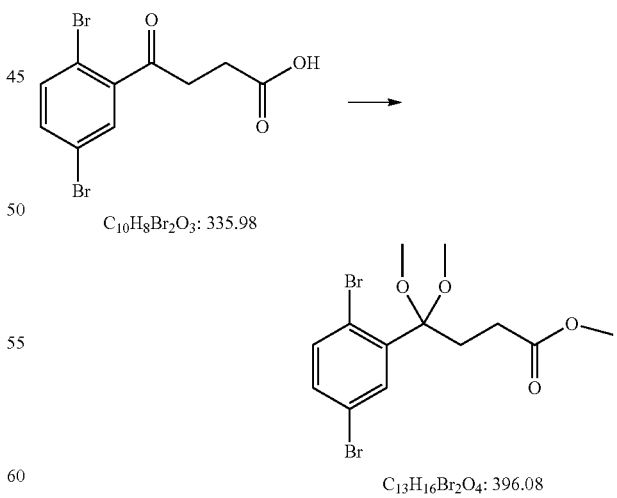

The starting material (33.6 g, 0.1 mol), trimethyl orthoformate (C4H10O3=106.12, 31.84 g, 0.3 mol) and methanol (90 mL) were dosed in a 250 mL reaction flask, and 10 drops of sulfuric acid was then dosed; the mixture was heated to 55° C. to react for 6 hours, TLC tracked the reaction process until the starting material was completely converted, and the solvent was distilled off under reduced pressure. The residue was diluted with dichloromethane (150 mL), the reaction was quenched with saturated potassium bicarbonate (100 mL), the organic phase was separated, rinsed with brine twice, 100 mL each time, and dried over anhydrous magnesium sulfate, and the solvent was distilled off, thus obtaining the product (35.25 g, 89%), which was directly used in the next step.

MS (ESI) m/z: 400, 398.

Example 4d. Synthesis of 4-(2,5-dibromophenyl)-4-oxobutanamide

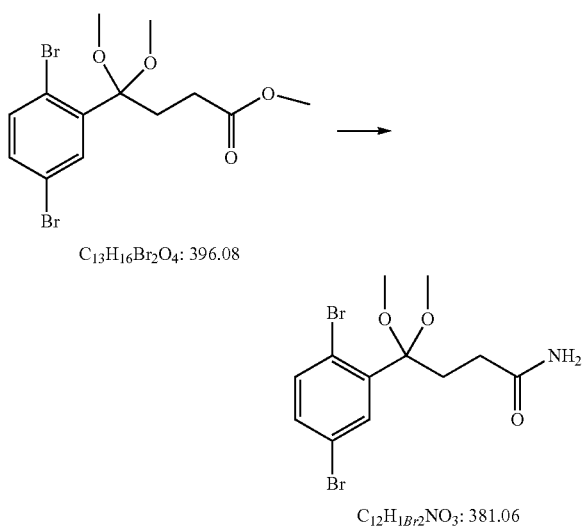

100 mL of methanol was dosed in a 250 mL reaction flask and cooled to below 0° C., and ammonia gas was introduced until the solution was saturated (about 10-12 g); the esterification product from step 4c was dosed in 30 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 4c in the reaction solution basically disappeared, the reaction was stopped, and the solvent was removed under reduced pressure, thus obtaining an oily product which was used directly in the next step of reaction.

MS (ESI) m/z: 385(M+H)+.

Example 4e. Synthesis of 5-(2,5-bromophenyl)-3,4-dihydro-2H-pyrrole

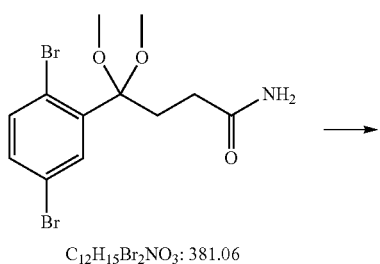

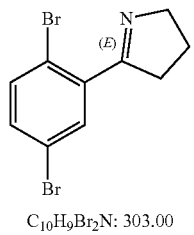

Dry isopropyl ether (600 mL), the amide (19.05 g, 0.05 mol) from step 4d, and sodium borohydride (29.26 g, 0.77 mol) were dosed in a 1000 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% potassium bicarbonate to neutrality, extracted with isopropyl acetate, dried over anhydrous sodium sulfate, filtered and concentrated under reduced pressure, thus obtaining oily 5-(2,5-dibromophenyl)-3,4-dihydro-2H-pyrrole (10.3 g, 68%).

$^1$H NMR, 400 MHz, CD$_3$OD δ:7.78 (m, 1H), 7.43-7.34 (m, 2H), 3.54 (m, 2H), 2.12 (dt, J=10.3, 2.0 Hz, 2H), 1.97 (dt, J=15.8, 7.9 Hz, 2H).

Example 4f. Synthesis of 2-(2,5-diiodophenyl)pyrrolidine

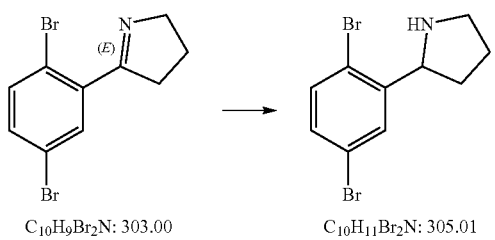 [SMILES: Brc1ccc(Br)c(C2=NCCC2)c1 ; Brc1ccc(Br)c(C2CCCN2)c1]

The oily 5-(2,5-dibromophenyl)-3,4-dihydro-2H-pyrrole (7.58 g, 0.025 mmoL) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with NaHCO$_3$ and then extracted with trichloromethane; the organic layer was dried over anhydrous sodium sulfate overnight and filtered to remove the solvent, thus obtaining a light yellow oily product, i.e., crude product (6.92 g, 90.7%), which was directly used into next step of reaction.

LC-ESI-MS (m/z): 309[M+H]$^+$.

Example 5: Synthesis of Key Intermediate 4: Synthesis of 2-(2-bromo-4-fluorophenyl)pyrrolidine

Example 5a. Synthesis of (E)-4-(2-bromo-4-fluorohenyl)-4-oxobut-2-enoic acid

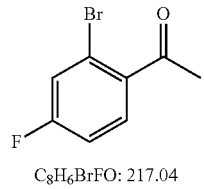

C$_8$H$_6$BrFO: 217.04

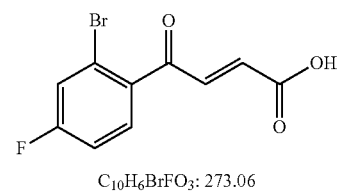

C$_{10}$H$_6$BrFO$_3$: 273.06

2-bromo-4-fluoroacetophenone (32.56 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 5% sodium carbonate-10% sodium bicarbonate aqueous solution (200 mL) was then dosed, and the mixture was extracted twice with isopropyl acetate, 200 mL each time; after the aqueous layer was acidified (10% hydrochloric acid, 300 mL), and extraction was carried out twice with isopropyl acetate, 200 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with isopropyl acetate (300 mL) and rinsed with brine 3 times, 100 mL each time; organic phase was dried over anhydrous sodium sulfate, and the solvent was removed under reduced pressure, thus obtaining the target product (24.41 g, 59.6%) as a yellow solid with an M.P. of 146° C. to 148° C.

MS (EI) m/z:273 (M+).

Example 5b. Synthesis of 4-(2-bromo-4-fluorophenyl)-4-oxobutanoic acid

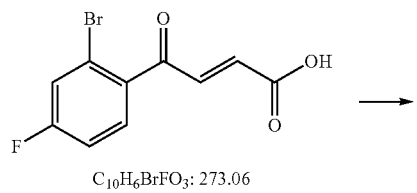

C$_{10}$H$_6$BrFO$_3$: 273.06

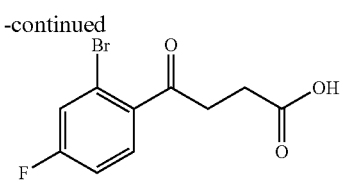

C$_{10}$H$_8$BrFO$_3$: 275.07

210 mL of acetic acid, 75 mL of water, and starting material (40.13 g, 147 mmol) were dosed in a 500 mL reaction flask; zinc powder (10.9 g, 166 mmol) was dosed in the reaction mixture in batches within about 1 hour in a stirring way; the mixture was further stirred for 3 hours, the reaction mixture was exacted and layered with isopropyl acetate (300 mL), the organic phase was rinsed with brine (3×100 mL) and dried over anhydrous sodium sulfate, and the solvent was removed under reduced pressure, thus obtaining the target product (25.07 g, 62.8%) with an M.P. of 150° C. to 153° C.

MS (EI) m/z: 275 (M+).

Example 5c. Synthesis of methyl 4-(2-bromo-4-fluorophenyl)-4-oxobutanoate

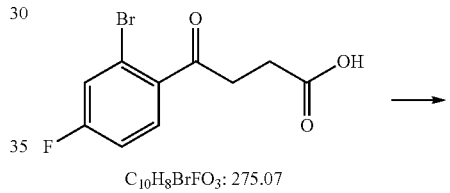

C$_{10}$H$_8$BrFO$_3$: 275.07

C$_{13}$H$_{16}$BrFO$_4$: 335.17

The starting material (27.6 g, 0.1 mol), trimethyl orthoformate (C4H10O3=106.12, 31.84 g, 0.3 mol) and methanol (90 mL) were dosed in a 250 mL reaction flask, and 10 drops of sulfuric acid was then dosed; the mixture was heated to 60° C. to react for 5 hours, TLC tracked the reaction process until the starting material was completely converted, and the solvent was distilled off under reduced pressure. The residue was diluted with chloroform (150 mL), the reaction was quenched with 5% potassium carbonate (100 mL), the organic phase was separated, rinsed with brine twice, 100 mL each time, and dried over anhydrous magnesium sulfate, and the solvent was distilled off, thus obtaining the product (30.84 g, 92%), which was directly used in the next step.

MS (ESI) m/z: 337 [M+H]$^+$.

Example 5d. Synthesis of 4-(2-bromo-4-fluorophenyl)-4-oxobutanamide

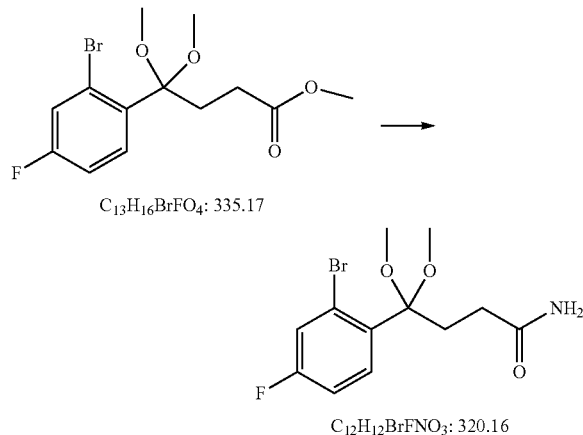

100 mL of methanol was dosed in a 250 mL reaction flask and cooled to below 0° C., and ammonia gas was introduced until the solution was saturated (about 10-12 g); the esterification product from step 5c was dosed in 30 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 5c in the reaction solution basically disappeared, the reaction was stopped, and the solvent was removed under reduced pressure, thus obtaining an oily product which was used directly in the next step of reaction.

MS (ESI) m/z: 322.1(M+H)+.

Example 5e. Synthesis of 5-(2-bromo-4-fluorophenyl)-3,4-dihydro-2H-pyrrole

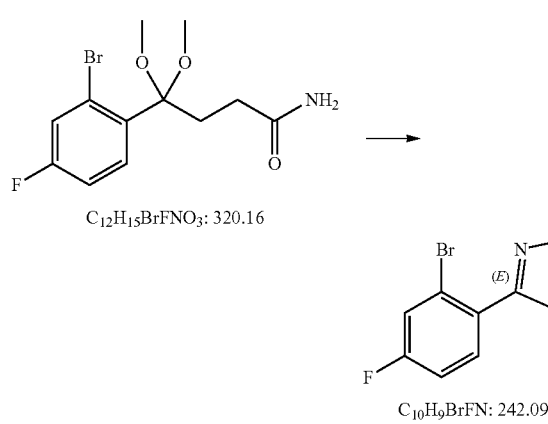

Dry tetrahydrofuran (300 mL), the amide (16.0 g, 0.05 mol) from step 5d, and sodium borohydride (29.26 g, 0.77 mol) were dosed in a 500 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% potassium bicarbonate to neutrality, extracted with dichloromethane, dried over anhydrous sodium sulfate, filtered and concentrated under reduced pressure, thus obtaining oily 5-(2-bromo-4-fluorophenyl)-3,4-dihydro-2H-pyrrole (9.8 g, 81%).

LC-ESI-MS (m/z): 244[M+H]$^+$.

Example 5f: Synthesis of 2-(2-bromo-4-fluorophenyl)pyrrolidine

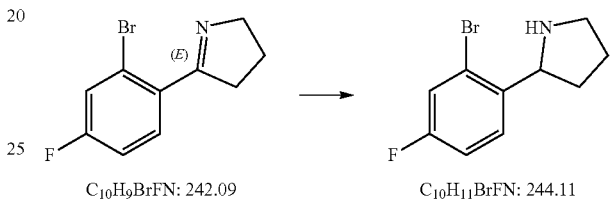

The oily 5-(2-bromo-4-fluorophenyl)-3,4-dihydro-2H-pyrrole (6.05 g, 0.025 mmoL) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with KHCO3 and then extracted with ethyl acetate; the organic layer was dried over anhydrous sodium sulfate overnight and filtered to remove the solvent, thus obtaining a light yellow oily product, i.e., crude product (5.84 g, 95.7%), which was directly used into next step of reaction.

LC-ESI-MS (m/z): 246[M+H]$^+$.

Example 6: Synthesis of Key Intermediate 4: Synthesis of 2-(3-bromo-4-fluorophenyl)pyrrolidine

Example 6a. Synthesis of (E)-4-(3-bromo-4-fluorohenyl)-4-oxobut-2-enoic acid

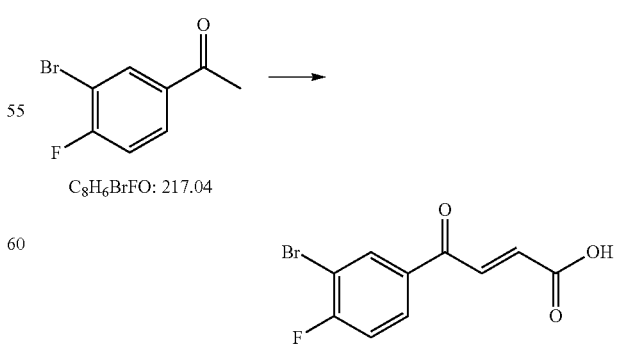

3-bromo-4-fluoroacetophenone (32.56 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 10% sodium bicarbonate aqueous solution (300 mL) was then dosed, and the mixture was extracted twice with toluene, 200 mL each time; after the aqueous layer was acidified (10% hydrochloric acid, 300 mL), and extraction was carried out twice with toluene, 200 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with toluene (300 mL) and rinsed with brine 3 times, 100 mL each time; organic phase was dried over anhydrous sodium sulfate, and the solvent was removed under reduced pressure, thus obtaining the target product (24.78 g, 60.5%) as a yellow solid with an M.P. of 143° C. to 146° C.

MS (EI) m/z: 275 (M+).

Example 6b. Synthesis of 4-(3-bromo-4-fluorophenyl)-4-oxobutanoic acid

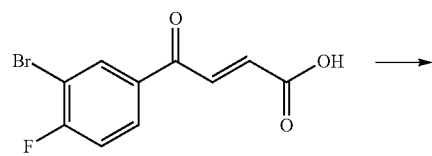

$C_{10}H_6BrFO_3$: 273.06

210 mL of acetic acid, 75 mL of water, and starting material (40.13 g, 147 mmol) were dosed in a 500 mL reaction flask; zinc powder (10.9 g, 166 mmol) was dosed in the reaction mixture in batches within about 1 hour in a stirring way; the mixture was further stirred for 3 hours, the reaction mixture was exacted and layered with toluene (300 mL), the organic phase was rinsed with brine (3×100 mL) and dried over anhydrous sodium sulfate, and the solvent was removed under reduced pressure, thus obtaining the target product (25.07 g, 62%) with an M.P. of 145° C. to 149° C.

MS (EI) m/z: 277 (M+).

Example 6c. Synthesis of methyl 4-(3-bromo-4-fluorophenyl)-4-oxobutanoate

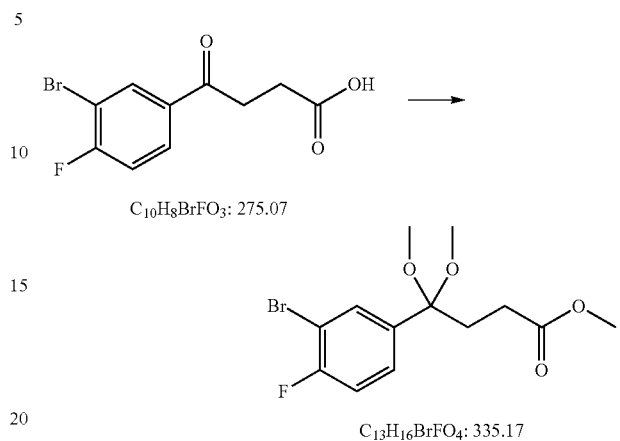

$C_{10}H_8BrFO_3$: 275.07

$C_{13}H_{16}BrFO_4$: 335.17

The starting material (27.6 g, 0.1 mol), trimethyl orthoformate (C4H10O3=106.12, 31.84 g, 0.3 mol) and methanol (90 mL) were dosed in a 250 mL reaction flask, and 10 drops of sulfuric acid was then dosed; the mixture was heated to 60° C. to react for 5 hours, TLC tracked the reaction process until the starting material was completely converted, and the solvent was distilled off under reduced pressure. The residue was diluted with ethyl acetate (180 mL), the reaction was quenched with 5% sodium carbonate (100 mL), the organic phase was separated, rinsed with brine twice, 100 mL each time, and dried over anhydrous magnesium sulfate, and the solvent was distilled off, thus obtaining the product (31.17 g, 93%), which was directly used in the next step.

MS (ESI) m/z: 337(M+H)+.

Example 6d. Synthesis of 4-(3-bromo-4-fluorophenyl)-4-oxobutanamide

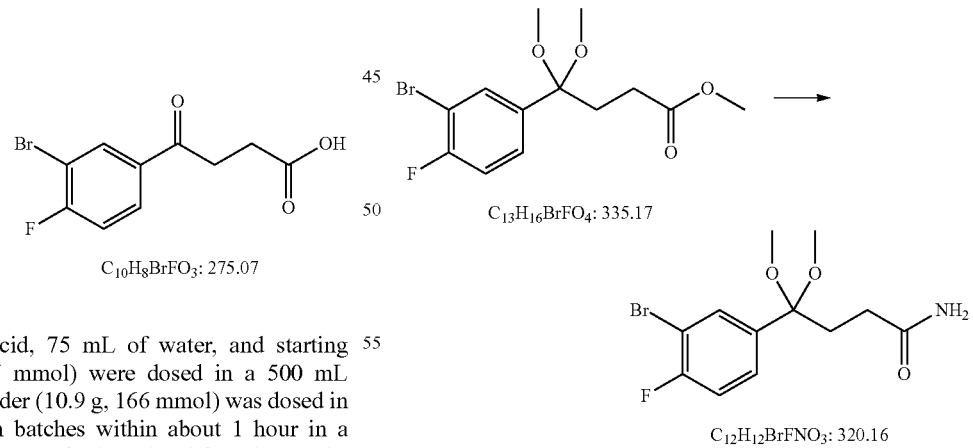

$C_{13}H_{16}BrFO_4$: 335.17

$C_{12}H_{12}BrFNO_3$: 320.16

100 mL of methanol was dosed in a 250 mL reaction flask and cooled to below 0° C., and ammonia gas was introduced until the solution was saturated (about 10-12 g); the esterification product from step 6c was dosed in 30 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 6c in the reaction solution basically disappeared, the reaction was stopped, and the solvent was removed under reduced pressure, thus obtaining an oily product which was used directly in the next step of reaction.

MS (ESI) m/z: 322.1(M+H)+.

Example 6e. Synthesis of 5-(3-bromo-4-fluorophenyl)-3,4-dihydro-2H-pyrrole

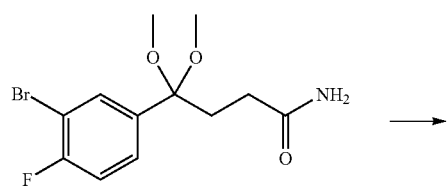

C$_{12}$H$_{15}$BrFNO$_3$: 320.16

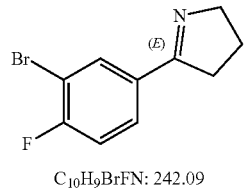

C$_{10}$H$_9$BrFN: 242.09

Dry tetrahydrofuran (300 mL), the amide (16.0 g, 0.05 mol) from step 6d, and sodium borohydride (29.26 g, 0.77 mol) were dosed in a 500 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% potassium bicarbonate to neutrality, extracted with chloroform, dried over anhydrous sodium sulfate, filtered and concentrated under reduced pressure, thus obtaining oily 5-(3-bromo-4-fluorophenyl)-3,4-dihydro-2H-pyrrole (9.56 g, 79%).

LC-ESI-MS (m/z): 244[M+H]$^+$.

Example 6f: Synthesis of 2-(3-bromo-4-fluorophenyl)pyrrolidine

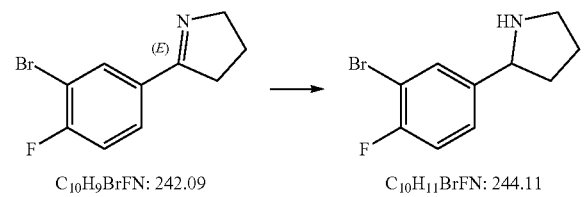

C$_{10}$H$_9$BrFN: 242.09    C$_{10}$H$_{11}$BrFN: 244.11

The oily 5-(3-bromo-4-fluorophenyl)-3,4-dihydro-2H-pyrrole (6.05 g, 0.025 mmoL) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with NaHCO$_3$ and then extracted with isopropyl acetate; the organic layer was dried over anhydrous sodium sulfate overnight and filtered to remove the solvent, thus obtaining a light yellow oily product, i.e., crude product (5.83 g, 95.5%), which was directly used into next step of reaction.

LC-ESI-MS (m/z): 246[M+H]$^+$.

Example 7: Synthesis of Key Intermediate 4: Synthesis of 2-(4-bromo-4-fluorophenyl)pyrrolidine Example 7a. Synthesis of (E)-4-(4-bromo-3-fluorohenyl)-4-oxobut-2-enoic acid

C$_8$H$_6$BrFO: 217.04

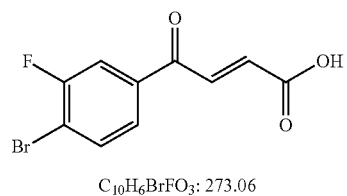

C$_{10}$H$_6$BrFO$_3$: 273.06

4-bromo-3-fluoroacetophenone (32.56 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 5% sodium hydroxide aqueous solution (300 mL) was then dosed, and the mixture was extracted twice with methyl tert-butyl ether, 200 mL each time; after the aqueous layer was acidified (5% hydrochloric acid, 300 mL), and extraction was carried out twice with methyl tert-butyl ether, 200 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with methyl tert-butyl ether (300 mL) and rinsed with brine 3 times, 100 mL each time; organic phase was dried over anhydrous sodium sulfate, and the solvent was removed under reduced pressure, thus obtaining the target product (23.96 g, 58.5%) as a yellow solid with an M.P. of 144° C. to 146° C.

MS (EI) m/z: 275 (M+).

Example 7b. Synthesis of 4-(4-bromo-3-fluorophenyl)-4-oxobutanoic acid

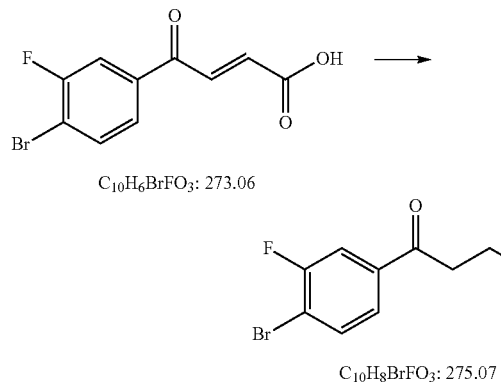

C₁₀H₆BrFO₃: 273.06

C₁₀H₈BrFO₃: 275.07

210 mL of acetic acid, 75 mL of water, and starting material (40.15 g, 147 mmol) were dosed in a 500 mL reaction flask; zinc powder (10.9 g, 166 mmol) was dosed in the reaction mixture in batches within about 1 hour in a stirring way; the mixture was further stirred for 3 hours, the reaction mixture was exacted and layered with methyl tert-butyl ether (300 mL), the organic phase was rinsed with brine (3×100 mL) and dried over anhydrous sodium sulfate, and the solvent was removed under reduced pressure, thus obtaining the target product (25.07 g, 62%) with an M.P. of 145° C. to 149° C.

MS (EI) m/z: 277 (M+).

Example 7c. Synthesis of methyl 4-(4-bromo-3-fluorophenyl)-4-oxobutanoate

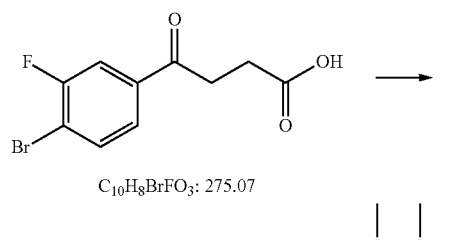

C₁₀H₈BrFO₃: 275.07

C₁₃H₁₆BrFO₄: 335.17

The starting material (27.6 g, 0.1 mol), trimethyl orthoformate (C4H10O3=106.12, 31.84 g, 0.3 mol) and methanol (90 mL) were dosed in a 250 mL reaction flask, and 10 drops of sulfuric acid was then dosed; the mixture was heated to 68° C. to react for 6 hours, TLC tracked the reaction process until the starting material was completely converted, and the solvent was distilled off under reduced pressure. The residue was diluted with isopropyl acetate (180 mL), the reaction was quenched with 5% sodium carbonate (100 mL), the organic phase was separated, rinsed with brine twice, 100 mL each time, and dried over anhydrous magnesium sulfate, and the solvent was distilled off, thus obtaining the product (31.84 g, 95%), which was directly used in the next step.

MS (ESI) m/z: 337(M+H).

Example 7d. Synthesis of 4-(4-bromo-3-fluorophenyl)-4-oxobutanamide

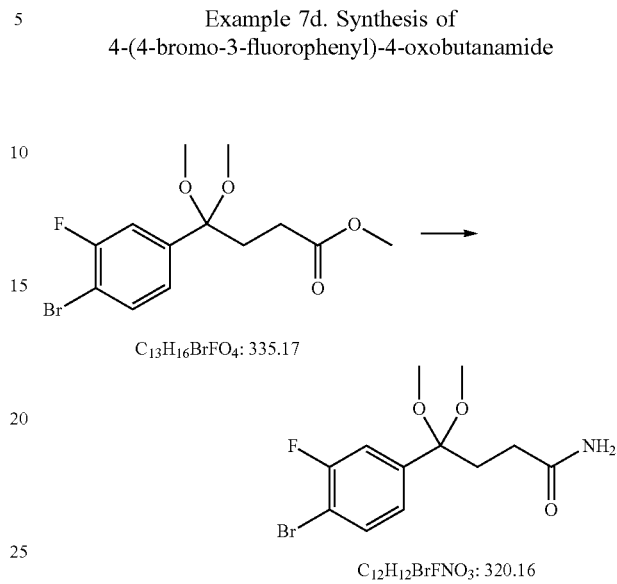

C₁₃H₁₆BrFO₄: 335.17

C₁₂H₁₂BrFNO₃: 320.16

100 mL of methanol was dosed in a 250 mL reaction flask and cooled to below 0° C., and ammonia gas was introduced until the solution was saturated (about 10-12 g); the esterification product from step 7c was dosed in 30 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 7c in the reaction solution basically disappeared, the reaction was stopped, and the solvent was removed under reduced pressure, thus obtaining an oily product which was used directly in the next step of reaction.

MS (ESI) m/z: 322.1(M+H)+.

Example 7e. Synthesis of 5-(4-bromo-3-fluorophenyl)-3,4-dihydro-2H-pyrrole

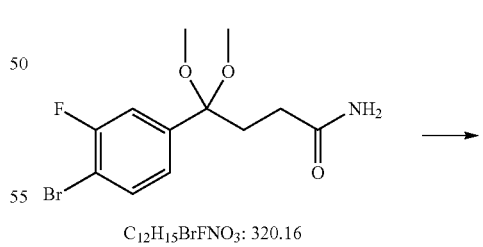

C₁₂H₁₅BrFNO₃: 320.16

C₁₀H₉BrFN: 242.09

Dry tetrahydrofuran (300 mL), the amide (16.0 g, 0.05 mol) from step 7d, and sodium borohydride (29.26 g, 0.77 mol) were dosed in a 500 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% sodium bicarbonate to neutrality, extracted with isopropyl acetate, dried over anhydrous sodium sulfate, filtered and concentrated under reduced pressure, thus obtaining oily 5-(4-bromo-3-fluorophenyl)-3,4-dihydro-2H-pyrrole (10.04 g, 83%).

LC-ESI-MS (m/z): 244[M+H]$^+$.

Example 7f: Synthesis of 2-(4-bromo-3-fluorophenyl)pyrrolidine

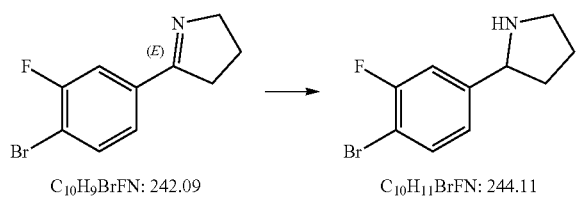

The oily 5-(4-bromo-3-fluorophenyl)-3,4-dihydro-2H-pyrrole (6.05 g, 0.025 mmoL) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with NaHCO$_3$ and then extracted with isopropyl acetate; the organic layer was dried over anhydrous sodium sulfate overnight and filtered to remove the solvent, thus obtaining a light yellow oily product, i.e., crude product (5.86 g, 95.5%), which was directly used into next step of reaction.

LC-ESI-MS (m/z): 246[M+H]$^+$.

Example 8: Synthesis of Key Intermediate 4: Synthesis of 2-(3-fluoro-5-iodophenyl)pyrrolidine Example 8a. Synthesis of (E)-4-(3-fluoro-5-iodophenyl)-4-oxobut-2-enoic acid

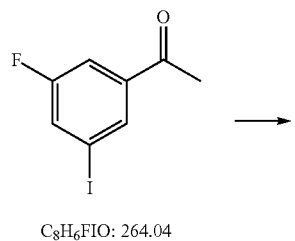

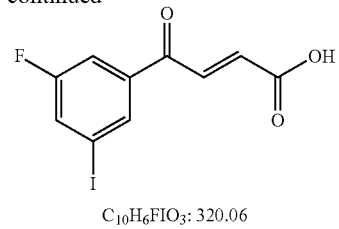

3-fluoro-5-iodoacetophenone (39.6 g, 150 mmol) and glyoxylic acid monohydrate (13.9 g, 151 mmol) were dosed in a 500 mL reactor, and then heated to react and distilled off water under reduced pressure (95° C., 0.1 Mpa); after 3 hours of reaction, the reaction mixture was cooled to room temperature, 5% potassium hydroxide aqueous solution (300 mL) was then dosed, and the mixture was extracted twice with methyl tert-butyl ketone, 200 mL each time; after the aqueous layer was acidified (5% hydrochloric acid, 300 mL), and extraction was carried out twice with methyl tert-butyl ether, 200 mL each time; the organic phases were combined, rinsed with brine, and dried over anhydrous sodium sulfate, and the solvent was removed under reduced pressure, thus obtaining an orange solid. The solid was dissolved in glacial acetic acid (50 mL) and concentrated hydrochloric acid (36%, 5 mL), the mixture was heated to reflux for 4 hours, and the acetic acid was removed under reduced pressure. The residue was extracted with methyl tert-butyl ketone (300 mL) and rinsed with brine 3 times, 100 mL each time; organic phase was dried over anhydrous sodium sulfate, and the solvent was removed under reduced pressure, thus obtaining the target product (26.54 g, 55.3%) as a yellow solid with an M.P. of 141° C. to 145° C.

MS (EI) m/z: 320 (M+).

Example 8b. Synthesis of 4-(3-fluoro-5-iodophenyl)-4-oxobutanoic acid

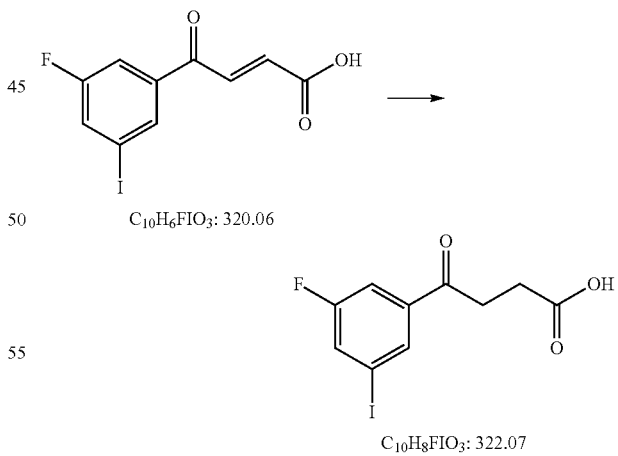

210 mL of acetic acid, 75 mL of water, and starting material (47.05 g, 147 mmol) were dosed in a 500 mL reaction flask; zinc powder (10.9 g, 166 mmol) was dosed in the reaction mixture in batches within about 1 hour in a stirring way; the mixture was further stirred for 3 hours, the reaction mixture was exacted and layered with methyl tert-butyl ketone (300 mL), the organic phase was rinsed with brine (3×100 mL) and dried over anhydrous sodium sulfate, and the solvent was removed under reduced pressure, thus obtaining the target product (27.55 g, 58.2%) with an M.P. of 147° C. to 150° C.

MS (EI) m/z: 322 (M+).

Example 8c. Synthesis of methyl 4-(3-fluoro-5-iodophenyl)-4-oxobutanoate

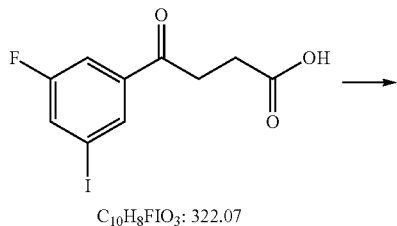

C₁₀H₈FIO₃: 322.07

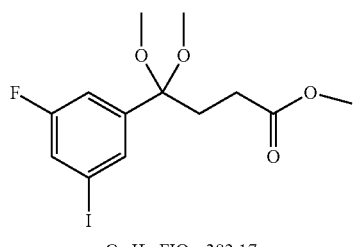

C₁₃H₁₆FIO₄: 382.17

The starting material (27.6 g, 0.1 mol), trimethyl orthoformate (C4H10O3=106.12, 34.78 g, 0.3 mol) and methanol (90 mL) were dosed in a 250 mL reaction flask, and 10 drops of sulfuric acid was then dosed; the mixture was heated to 60° C. to react for 8 hours, TLC tracked the reaction process until the starting material was completely converted, and the solvent was distilled off under reduced pressure. The residue was diluted with isopropyl acetate (180 mL), the reaction was quenched with 5% sodium carbonate (100 mL), the organic phase was separated, rinsed with brine twice, 100 mL each time, and dried over anhydrous magnesium sulfate, and the solvent was distilled off, thus obtaining the product (34.78 g, 910%), which was directly used in the next step.

MS (ESI) m/z: 383.1(M+H).

Example 8d. Synthesis of 4-(3-fluoro-5-iodophenyl)-4-oxobutanamide

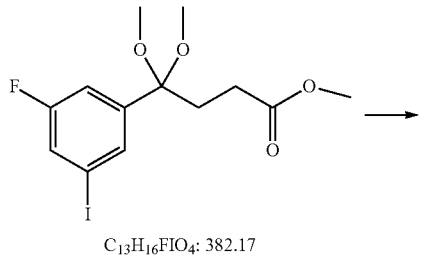

C₁₃H₁₆FIO₄: 382.17

-continued

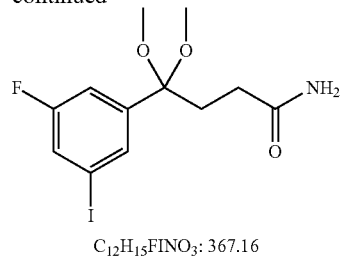

C₁₂H₁₅FINO₃: 367.16

100 mL of methanol was dosed in a 250 mL reaction flask and cooled to below 0° C., and ammonia gas was introduced until the solution was saturated (about 10-12 g); the esterification product from step 8c was dosed in 30 mL of methanol to obtain a liquid, the liquid was dropwise dosed in the methanol-ammonia saturated solution, and the internal temperature was maintained at about 0° C. After the liquid was completely dosed dropwise, the reaction solution continued to react for 16 hours at 0° C. When TLC detected that the esterification product from step 8c in the reaction solution basically disappeared, the reaction was stopped, and the solvent was removed under reduced pressure, thus obtaining an oily product which was used directly in the next step of reaction.

MS (ESI) m/z: 368.1(M+H)+.

Example 8e. Synthesis of 5-(3-fluoro-5-iodophenyl)-3,4-dihydro-2H-pyrrole

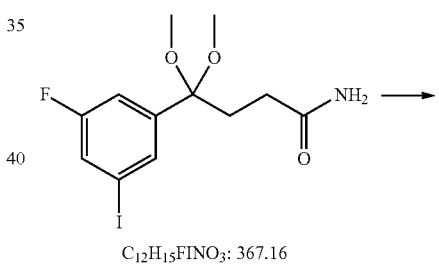

C₁₂H₁₅FINO₃: 367.16

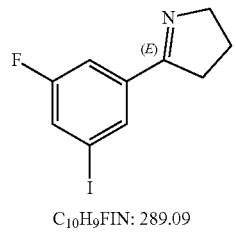

C₁₀H₉FIN: 289.09

Dry tetrahydrofuran (300 mL), the amide (18.4 g, 0.05 mol) from step 8d, and sodium borohydride (29.26 g, 0.77 mol) were dosed in a 500 mL reactor, stirred to be uniform, and then cooled to 0° C. with an ice bath; in the presence of nitrogen, boron trifluoride ether solution (36.75 mL, 0.3 mol) was dosed dropwise within about 2 hours, the ice bath was removed, the mixture was heated to reflux for 16 hours, TLC detected the reaction until raw material was completely converted, the reaction solution was cooled to 5° C., 6N hydrochloric acid (35 mL) was slowly dosed dropwise, the mixture was heated to reflux for 1 hour, the reaction solution was cooled to 40° C., and the solvent was removed under reduced pressure. The residue was diluted with water, neutralized with 10% sodium bicarbonate to neutrality, extracted with isopropyl acetate, dried over anhydrous sodium sulfate, filtered and concentrated under reduced pressure, thus obtaining oily 5-(3-fluoro-5-iodophenyl)-3,4-dihydro-2H-pyrrole (11.27 g, 78%).

The NMR data of the product obtained were as follows:
$^1$H NMR, 400 MHz, CD$_3$OD δ:7.78 (m, 1H), 7.43-7.34 (m, 2H), 3.54 (m, 2H), 2.12 (dt, J=10.3, 2.0 Hz, 2H), 1.97 (dt, J=15.8, 7.9 Hz, 2H).
$^{13}$C NMR, 100 MHz, CD$_3$OD δ:176.2, 158.2 (d, J=260.3), 155.0 (d, J=10.3), 124.0 (d, J=3.1), 119.4 (d, J=23.5), 118.4 (d, J=23.5), 62.3, 36.5, 21.0.

Example 8f: Synthesis of 2-(3-fluoro-5-iodophenyl)pyrrolidine

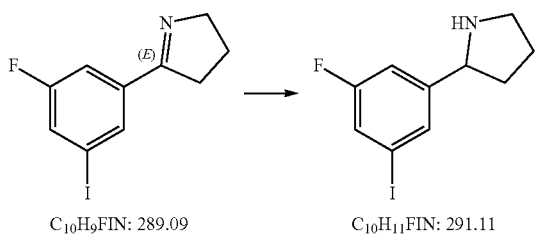

C$_{10}$H$_9$FIN: 289.09    C$_{10}$H$_{11}$FIN: 291.11

The oily 5-(3-fluoro-5-iodophenyl)-3,4-dihydro-2H-pyrrole (7.23 g, 0.025 mmoL) was dosed in 100 mL of a solution of methanol and water (4:1); the mixed solution was cooled to 0° C., sodium borohydride (0.95 g, 0.025 mol) was dosed in batches, hydrogen was released, and the reaction solution turned into a yellow turbid liquid; 3 hours later, the reaction solution was heated to room temperature, and the solvent was distilled off. The residue was treated with NaHCO$_3$ and then extracted with dichloromethane; the organic layer was dried over anhydrous sodium sulfate overnight and filtered to remove the solvent, thus obtaining a light yellow oily product, i.e., crude product (6.8 g, 93.5%), which was directly used into next step of reaction.
$^1$H NMR, 400 MHz, CDCl$_3$ δ: 7.29 (m, 1H), 7.02 (m, 1H), 6.96 (m, 1H), 4.09 (t, J=7.8 Hz, 1H), 3.16 (m, 1H), 3.04 (m, 1H), 2.21-2.30 (m, 1H), 1.77-1.95 (m, 3H), 1.57-1.67 (m, 1H).
LC-ESI-MS (m/z) 292[M+H]$^+$.

Step 2: Synthesis of Key Intermediate 8

Example 9: Synthesis of (S)—N-(5-chloropyrazolo[1,5-a]pyrimidin-3-yl)-3-hydroxypyrrolidine-1-carboxamide Example 9a. Synthesis of 5-chloropyrazolo[1,5-a]pyrimidin-3-amine

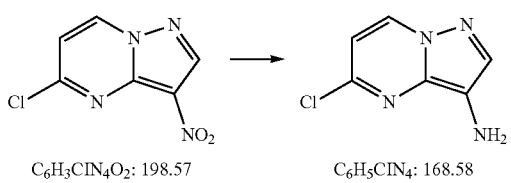

C$_6$H$_3$ClN$_4$O$_2$: 198.57    C$_6$H$_5$ClN$_4$: 168.58

5-chloro-3-nitropyrazolo[1,5-a]pyrimidine compound (25 g, 0.125 mol), ethanol (250 mL), and iron powder (75 g, 1.25 mol) were dosed in a 1000 mL reaction flask and heated to reflux in the presence of nitrogen, and ammonium chloride (66.5 g, 1.25 mol) aqueous solution (250 mL) was dosed dropwise at the same time within about 1 hour; the reflux reaction was continued for 6 hours; TLC tracked the reaction until the reaction was completed, the reactant was concentrated to paste under reduced pressure. The residue was diluted with water (100 mL), then layered with dichloromethane and extracted 4-6 times, 200 mL each time; the organic phases were combined, rinsed with saturated brine, dried over anhydrous magnesium sulfate, and concentrated under reduced pressure, thus obtaining 5-chloropyrazolo[1,5-a]pyrimidin-3-amine compound (419.7 g, 93.5%).
$^1$H NMR, 400 MHz, CD$_3$OD δ:9.29(d, J=7.2 Hz, 1H), 8.71 (s, 1H), 8.16(d, J=7.2 Hz, 1H), 5.92 (s, 2H):
MS(ESI)m/z: 169.8[M+H]$^+$.

Example 9b. Synthesis of 5-chloro-3-isocyanatopyrazolo[1,5-a]pyrimidine

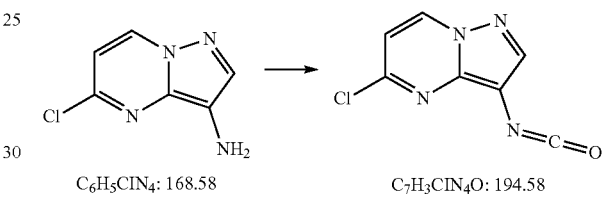

C$_6$H$_5$ClN$_4$: 168.58    C$_7$H$_3$ClN$_4$O: 194.58

Triphosgene (9.91 g, 33.38 mmol) was dissolved in 50 ml of tetrahydrofuran, 5-chloropyrazolo[1,5-a]pyrimidin-3-amine (16.86 g, 0.1 mol) and triethylamine (0.47 g, 4.64 mmol) were dosed, and the reaction system was stirred to react for 1 hour at 25° C. A suspension of 5-chloro-3-isocyanatopyrazolo[1,5-a]pyrimidine was obtained, and the product was directly subjected to the next reaction without purification.

Example 9c. Synthesis of (S)—N-(5-chloropyrazolo[1,5-a]pyrimidin-3-yl)-3-hydroxypyrrolidine-1-carboxamide

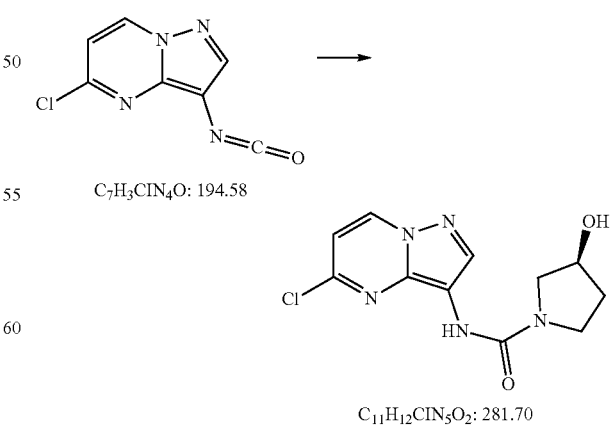

C$_7$H$_3$ClN$_4$O: 194.58

C$_{11}$H$_{12}$ClN$_5$O$_2$: 281.70

Sodium bicarbonate solution (80 ml, 0.5M, 40 mmol) was dosed in a 250 mL reactor, (S)-pyrrol-3-ol (79 g, 55 mmol)

was then dosed, the isocyanate solution prepared in step 9b (62 mL, 100 mmol, calculated on the basis of 5-chloropyrazolo[1,5-a]pyrimidin-3-amine) was dosed dropwise, and the temperature was maintained at about 0° C.; and then the mixture was further stirred at 0° C. for 3 hours and then heated to 50° C. to further react for 5 hours; the reaction solution was cooled to room temperature, extracted 3 times with ethyl acetate, 100 mL each time. The organic phases were combined, rinsed with 2N hydrochloric acid, then with brine, dried over anhydrous sodium sulfate, filtered, and concentrated under reduced pressure. The residue was subjected to silica gel column chromatography and elution with ethyl acetate/petroleum ether (5:5, v/v) was carried out, thus obtaining a product (22 g, 78%).

$^1$H NMR (300 MHz, $d_6$DMSO) δ: 9.26(d, J=7.2 Hz 1H), 8.73 (s, 1H), 8.78 (s, 1H), 8.07(d, J 7.2 Hz, 1H), 4.02 (m, 1H), 3.62 (m, 2H), 3.48 (m, 2H), 2.36 (m, 2H);

MS(ESI)m/z: 282[M+H]$^+$.

Step 3: Preparation of Halogenated Larotrectinib Analog 9

Example 10: Synthesis of Halogenated Larotrectinib Compound (R)-2-F-5-I-Larotrectinib

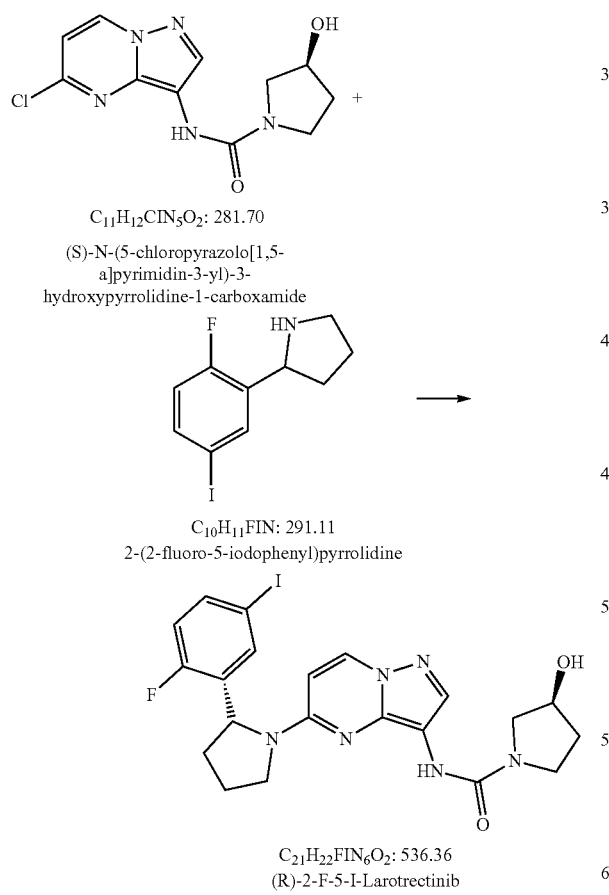

Pyrazolo (1,5a) pyrimidine compound (30 g, 106 mmol), 2-F-5-I-pyrrole compound (30.8 g, 106 mmol) and ethanol (200 mL) were dosed in a reaction flask, N,N-di Isopropylethylamine (27.3 g, 212 mmol) was dosed dropwise, and the reaction temperature was maintained within 30° C.; then, the reaction was continued for 5-8 hours under the control of TLC; after the reaction was completed, methyl tert-butyl ether (300 mL) was dosed and a solid precipitates out; the reaction solution was stirred at this temperature for 30 minutes, then filtered, and suction dried, thus obtaining 38.6 g of racemic mixture 2-F-5-I-Larotrectinib as a light yellow solid; the mother liquor is concentrated and subjected to silica gel column chromatography, and elution with ethyl acetate/n-hexane (5:5, v/v) was carried out, thus obtaining a product (12.8 g, 90.4%). Then, by chiral LC separation and purification, (R)-2-F-5-I-Larotrectinib was obtained as a pure white chiral solid, and (S)-2-F-5-I-Larotrectinib was obtained as a pure white chiral solid.

1H NMR (300 MHz, $d_6$DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H);

MS(ESI)m/z: 536.3, 537.3.

Example 11: Synthesis of Halogenated Larotrectinib Compound (R)-2-F-5-Br-Larotrectinib

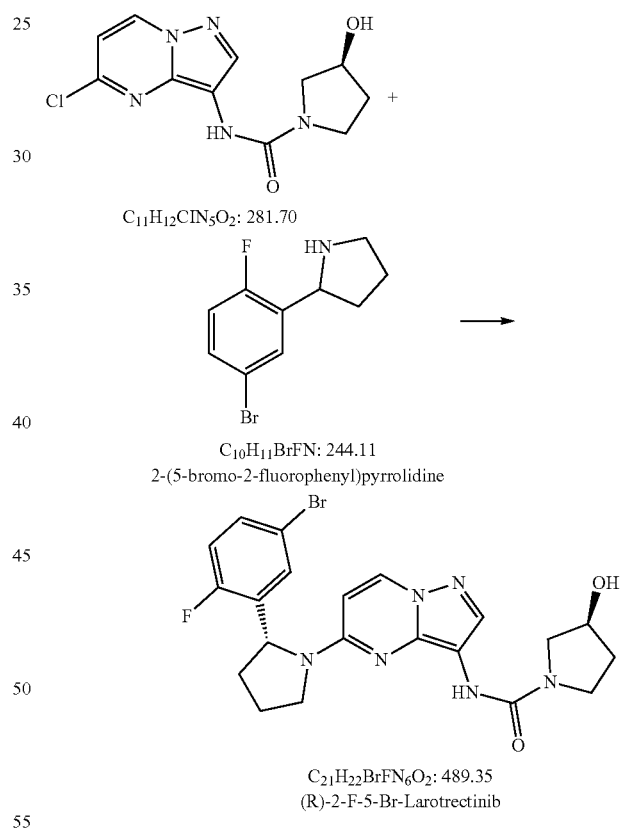

Pyrazolo (1,5a) pyrimidine compound (30 g, 106 mmol), 2-F-5-Br-pyrazole compound (25.8 g, 106 mmol) and acetonitrile (220 mL) were dosed in a reaction flask, a mixed solution of N,N-diisopropylethylamine (13.6 g, 106 mmol) and triethylamine (5.3 g, 53 mmol) was dosed dropwise, and the reaction temperature was maintained within 30° C.; then, the reaction was continued for 5 hours and the whole reaction was under the control of TLC; the post treatment was carried out in the same way as that in Example 6, and the racemic mixture 2-F-5-Br-Larotrectinib (48.6 g, 93.6%) was obtained as a white solid. Then, by chiral LC separation and purification, (R)-2-F-5-Br-Larotrectinib was obtained as a pure white chiral solid, and (S)-2-F-5-Br-Larotrectinib was obtained as a pure white chiral solid.

1H NMR (300 MHz, d₆DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H);

MS(ESI)m/z: 491.3(M+H)+.

Example 12: Synthesis of Halogenated Larotrectinib Compound (R)-2-Br-5-Br-Larotrectinib

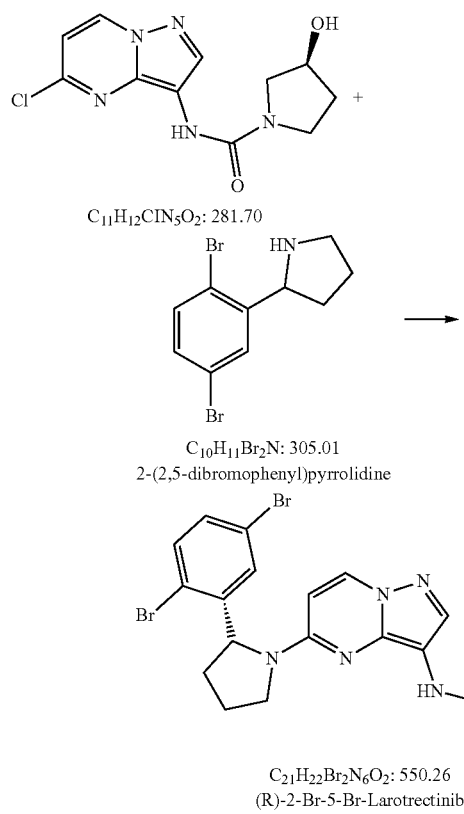

Example 13: Synthesis of Halogenated Larotrectinib Compound (R)-5-F-2-I-Larotrectinib

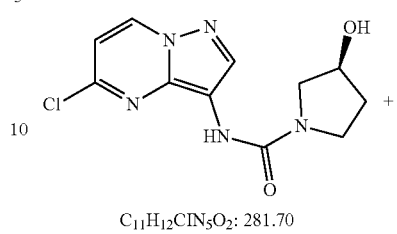

C₁₁H₁₂ClN₅O₂: 281.70

C₁₀H₁₁FIN: 291.11
2-(5-fluoro-2-iodophenyl)pyrrolidine

C₂₁H₂₂FIN₆O₂: 536.35
(R)-5-F-2-I-Larotrectinib

Pyrazolo (1,5a) pyrimidine compound (30 g, 106 mmol), 2-Br-5-Br-pyrazole compound (32.3 g, 106 mmol) and isopropanol (180 mL) were dosed in a reaction flask, N-methylmorpholine (C5H11NO=101.15, 21.4 g, 212 mmol) was dosed dropwise, and the reaction temperature was maintained within 25° C.; then, the reaction was continued for 8 hours and the whole reaction was under the control of TLC; the post treatment was carried out in the same way as that in Example 6, and the racemic mixture 2-Br-5-Br-Larotrectinib (52.7 g, 90.3%) was obtained as a white solid. Then, by chiral LC separation and purification, (R)-2-Br-5-Br-Larotrectinib was obtained as a pure white chiral solid and (S)-2-Br-5-Br-Larotrectinib was obtained as a pure white chiral solid. 1H NMR (300 MHz, d₆DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H);

MS(ESI)m/z: 554.2(M+H)+.

Pyrazolo (1,5a) pyrimidine compound (30 g, 106 mmol), 5-F-2-I-pyrrole compound (30.9 g, 106 mmol) and 1,4-dioxane (150 mL) were dosed in a reaction flask, N,N-lutidine (C7H10N2=122.17, 25.9 g, 212 mmol) was dosed dropwise, and the reaction temperature was maintained within 30° C.; then, the reaction was continued for 6 hours and the whole reaction was under the control of TLC; the post treatment was carried out in the same way as that in Example 6, and the racemic mixture 5-F-2-I-Larotrectinib (53.8 g, 94.6%) was obtained as a white solid. Then, by chiral LC separation and purification, (R)-5-F-2-I-Larotrectinib was obtained as a pure white chiral solid, and (S)-5-F-2-I-Larotrectinib was obtained as a pure white chiral solid. 1H NMR (300 MHz, d₆DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H);

MS(ESI)m/z: 536.3(M+H)+.

Example 14: Synthesis of Halogenated Larotrectinib Compound (R)-5-I-2-I-Larotrectinib

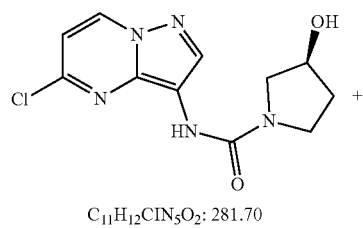

C$_{11}$H$_{12}$ClN$_5$O$_2$: 281.70

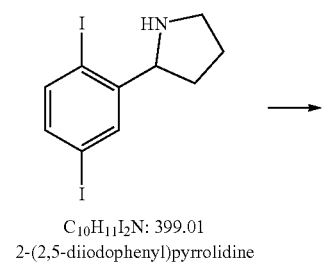

C$_{10}$H$_{11}$I$_2$N: 399.01
2-(2,5-diiodophenyl)pyrrolidine

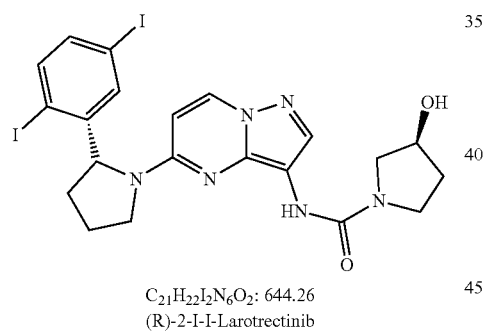

C$_{21}$H$_{22}$I$_2$N$_6$O$_2$: 644.26
(R)-2-I-I-Larotrectinib

Pyrazolo (1,5a) pyrimidine compound (30 g, 106 mmol), 2-I-5-I-pyrrole compound (32.3 g, 106 mmol), n-butanol (120 mL) and tert-butanol (80 mL) were dosed in a reaction flask, tetrabutylammonium iodide (C16H36IN=369.37, 0.39 g, 0.01 mmol) was then dosed, pyridine (12.6 g, 159 mmol) was dosed dropwise, and the reaction temperature was maintained within 15° C.; then, the reaction was continued for 10 hours and the whole reaction was under the control of TLC; the post treatment was carried out in the same way as that in Example 6, and the racemic mixture 2-I-5-I-Larotrectinib (58.4 g, 85.5%) was obtained as a light yellow solid. Then, by chiral LC separation and purification, (R)-2-I-5-I-Larotrectinib was obtained as a pure white chiral solid, and (S)-2-I-5-I-Larotrectinib was obtained as a pure white chiral solid. 1H NMR (300 MHz, d$_6$DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H); MS(ESI)m/z: 644.2(M+H)+.

Example 15: Synthesis of Halogenated Larotrectinib Compound (R)-4-F-2-Br-Larotrectinib

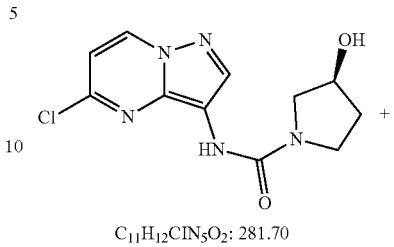

C$_{11}$H$_{12}$ClN$_5$O$_2$: 281.70

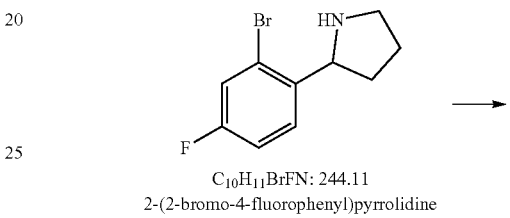

C$_{10}$H$_{11}$BrFN: 244.11
2-(2-bromo-4-fluorophenyl)pyrrolidine

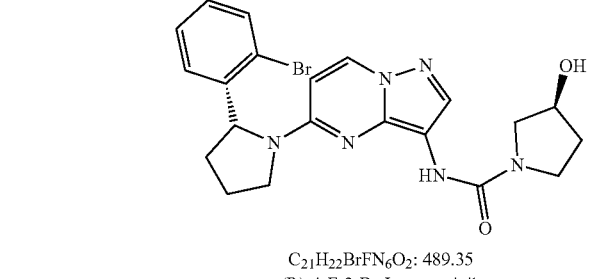

C$_{21}$H$_{22}$BrFN$_6$O$_2$: 489.35
(R)-4-F-2-Br-Larotrectinib

Pyrazolo (1,5a) pyrimidine compound (30 g, 106 mmol), 4-F-2-Br-pyrrole compound (30.9 g, 106 mmol) and tetrahydrofuran (150 mL) were dosed in a reaction flask, N-methylpiperidine was then dosed dropwise, pyridine (C6H13N=99.17, 21.0 g, 212 mmol) was dosed dropwise, and the reaction temperature was maintained within 35° C.; then, the reaction was continued for 6 hours and the whole reaction was under the control of TLC; the post treatment was carried out in the same way as that in Example 6, and the racemic mixture 4-F-2-Br-Larotrectinib (45.3 g, 87.4%) was obtained. Then, by chiral LC separation and purification, (R)-4-F-2-Br-Larotrectinib was obtained as a pure white chiral solid, and (S)-4-F-2-Br-Larotrectinib was obtained as a pure white chiral solid.

$^1$H NMR (300 MHz, d$_6$DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H);

MS(ESI)m/z: 491.4(M+H)+.

Example 16: Synthesis of Halogenated Larotrectinib Compound (R)-4-F-3-Br-Larotrectinib

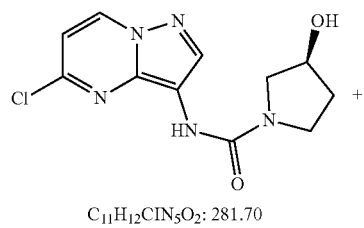

C₁₁H₁₂ClN₅O₂: 281.70

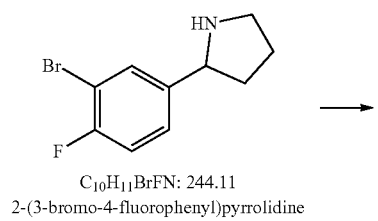

C₁₀H₁₁BrFN: 244.11
2-(3-bromo-4-fluorophenyl)pyrrolidine

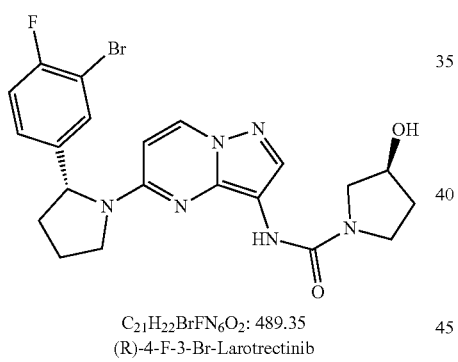

C₂₁H₂₂BrFN₆O₂: 489.35
(R)-4-F-3-Br-Larotrectinib

Pyrazolo (1,5a) pyrimidine compound (30 g, 106 mmol), 4-F-3-Br-pyrrole compound (30.9 g, 106 mmol) and toluene (200 mL) were dosed in a reaction flask, dimethylethylamine (C4H11N=73.14, 15.5 g, 212 mmol) was dosed dropwise, and the reaction temperature was maintained within 40° C.; then, the reaction was continued for 6 hours and the whole reaction was under the control of TLC; the post treatment was carried out in the same way as that in Example 6, and the racemic mixture 4-F-3-Br-Larotrectinib (44.1 g, 85.1%) was obtained as a white solid. Then, by chiral LC separation and purification, (R)-4-F-3-Br-Larotrectinib was obtained as a pure white chiral solid and (S)-4-F-3-Br-Larotrectinib was obtained as a pure white chiral solid.

¹H NMR (300 MHz, d₆DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H);

MS(ESI)m/z: 491.3(M+H)+.

Example 17: Synthesis of Halogenated Larotrectinib Compound (R)-4-Br-3-F-Larotrectinib

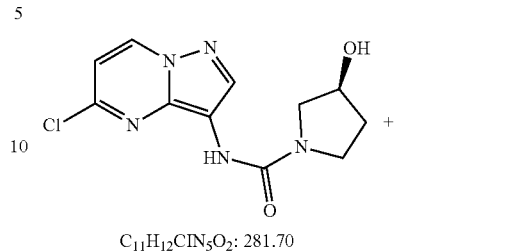

C₁₁H₁₂ClN₅O₂: 281.70

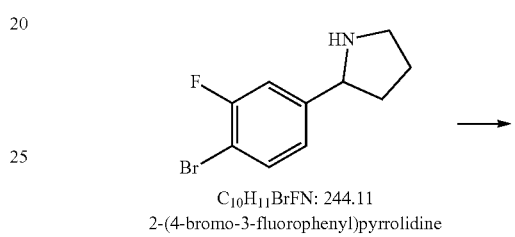

C₁₀H₁₁BrFN: 244.11
2-(4-bromo-3-fluorophenyl)pyrrolidine

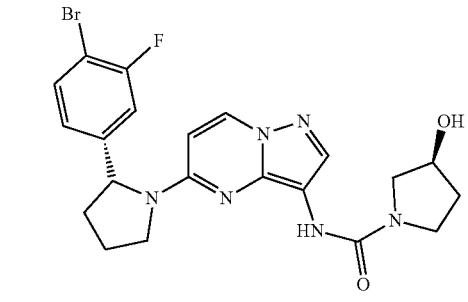

C₂₁H₂₂BrFN₆O₂: 489.35
(R)-4-Br-3-Fr-Larotrectinib

Pyrazolo (1,5a) pyrimidine compound (30 g, 106 mmol), 4-Br-3-F-pyrrole compound (30.9 g, 106 mmol) and acetone (200 mL) were dosed in a reaction flask, sodium carbonate (11.3 g, 106 mmol) was then dosed dropwise, and the reaction temperature was maintained within 35° C.; then, the reaction was continued for 8 hours and the whole reaction was under the control of TLC; the post treatment was carried out in the same way as that in Example 6, and the racemic mixture 4-Br-3-Br-Larotrectinib (42.8 g, 82.5%) was obtained as a white solid. Then, by chiral LC separation and purification, (R)-4-Br-3-F-Larotrectinib was obtained as a pure white chiral solid and (S)-4-Br-3-F-Larotrectinib was obtained as a pure white chiral solid.

¹H NMR (300 MHz, d₆DMSO) δ 9.12(d, J=7.2 Hz 1H), 8.73 (s, 1H), 8.78 (s, 1H), 8.07 (d, J=7.2 Hz, 1H), 6.8-7.3(m, 3H), 4.17 (m, 1H), 4.02 (m, 1H), 3.62 (m, 2H), 3.48 (m, 2H), 1.75-2.86 (m, 8H);

MS(ESI)m/z: 491.3(M+H)+.

Step 4: Preparation of Labeled Precursor

Example 18. Preparation of Labeled Precursor (R)-2-fluoro-5-tributyltin-Larotrectinib

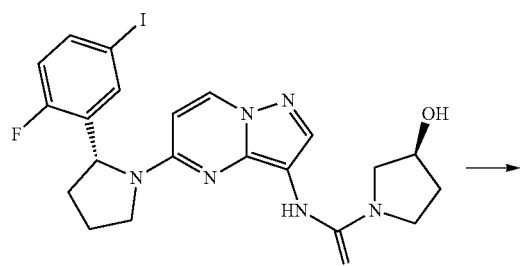

C₂₁H₂₂FIN₆O₂: 536.35
(R)-2-F-5-I-Larotrectinib

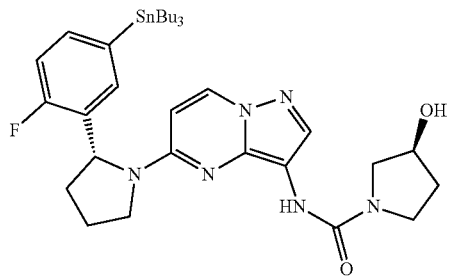

C₃₃H₄₉FN₆O₂Sn: 699.50
(R)-2-F-5-SnBu₃-Larotrectinib

Dry THF (2.5 mL), (R)-2-F-5-I-Larotrectinib (107 mg, 0.2 mmol), bistributyltin (C24H54Sn2=580.12, 417.9 mg, 0.72 mmol), and tetrakis (triphenylphosphorus) palladium (8.1 mg, 0.007 mmol) were sequentially dosed in a 5 mL reaction flask; in the presence of nitrogen, the mixture was refluxed for 8 hours and then cooled, the solvent was removed under reduced pressure; the remaining crude product was purified by aluminum oxide column chromatography (70-230 meshes), and elution with n-hexane/dichloromethane (20:80, v/v) and rinsing with 100% dichloromethane were then carried out, thus obtaining the target product (44.77 mg, 32%) as a white low-melting solid with a melting point of 36° C. to 39° C.

MS(ESI)m/z:700.29, C₃₃H₄₉FN₆O₂Sn=699.50.

Similarly, (R)-2-F-5-Br-Larotrectinib was dosed in the THF system to synthesize the labeled precursor (R)-2-fluoro-5-tributyltin-Larotrectinib.

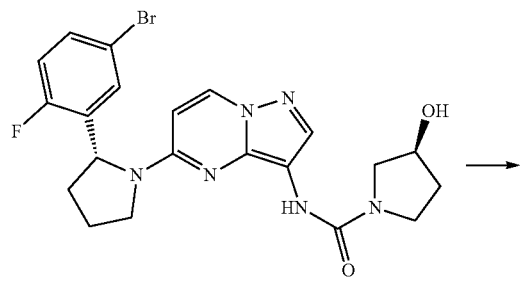

C₂₁H₂₂BrFN₆O₂: 489.35
(R)-2-F-5-Br-Larotrectinib

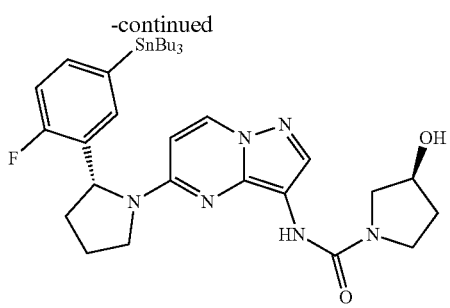

C₃₃H₄₉FN₆O₂Sn: 699.50
(R)-2-F-5-SnBu₃-Larotrectinib

Example 19. Preparation of Labeled Precursor (R)-5-F-2-SnMe₃-Larotrectinib

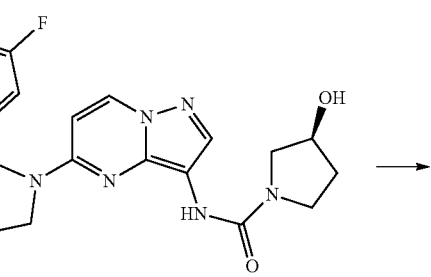

C₂₁H₂₂FIN₆O₂: 536.35
(R)-5-F-2-I-Larotrectinib

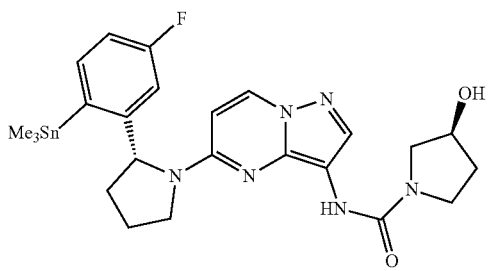

C₂₄H₃₁FN₆O₂Sn: 573.26
(R)-5-F-2-SnMe₃-Larotrectinib

Dry 1,4-dioxane (2.5 mL), (R)-5-F-2-I-Larotrectinib (107 mg, 0.2 mmol), Bistrimethyltin (C6H18Sn2=327.63, 235.9 mg, 0.72 mmol), Bis(triphenylphosphorus) palladium dichloride (5 mg, 0.007 mmol) were sequentially dosed in a 5 mL reaction flask; in the presence of nitrogen, the mixture was refluxed for 2 hours and then cooled, the solvent was removed under reduced pressure; the remaining crude product was purified by aluminum oxide column chromatography (70-230 meshes), and elution with n-hexane/dichloromethane (20:80, v/v) and rinsing with 100% dichloromethane were then carried out, thus obtaining the target product (R)-5-F-2-SnMe₃-Larotrectinib (48.2 mg, 42%) as a white low-melting solid with a melting point of 41° C. to 43° C.

MS(ESI)m/z:574.15, C₂₄H₃₁FN₆O₂Sn=573.26

Example 20. Preparation of Labeled Precursor (R)-3-F-5-SnMe₃-Larotrectinib

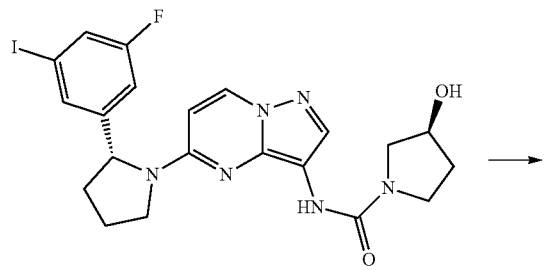

C₂₁H₂₂FIN₆O₂: 536.35
(R)-5-F-2-I-Larotrectinib

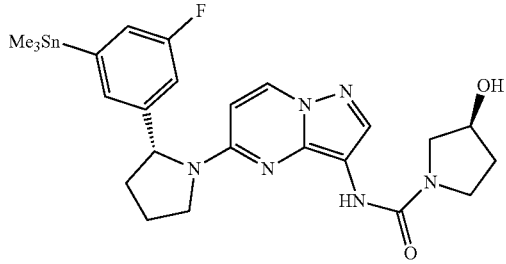

C₂₄H₃₁FN₆O₂Sn: 573.26
(R)-5-F-2-SnMe₃-Larotrectinib

Dry 1,4-Dioxane (2.5 mL), (R)-3-F-5-I-Larotrectinib (107 mg, 0.2 mmol), bistrimethyltin (C6H18Sn2=327.63, 235.9 mg, 0.72 mmol), and bis(triphenylphosphorus) palladium dichloride (5 mg, 0.007 mmol) were sequentially dosed in a 5 mL reaction flask; in the presence of nitrogen, the mixture was refluxed for 2 hours and then cooled, the solvent was removed under reduced pressure; the remaining crude product was purified by aluminum oxide column chromatography (70-230 meshes), and elution with n-hexane/dichloromethane (20:80, v/v) and rinsing with 100% dichloromethane were then carried out, thus obtaining the target product (48.2 mg, 42%) as a white low-melting solid with a melting point of 41° C. to 43° C.

MS(ESI)m/z:574.15, C24H31FN6O2Sn=573.26

Example 21. Preparation of Labeled Precursor (R)-4-F-2-SnMe₃-Larotrectinib

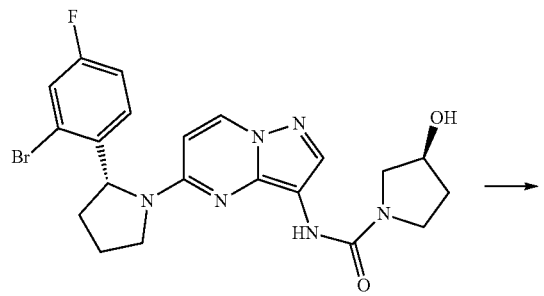

C₂₁H₂₂BrFN₆O₂: 489.35
(R)-4-F-2-Br-Larotrectinib

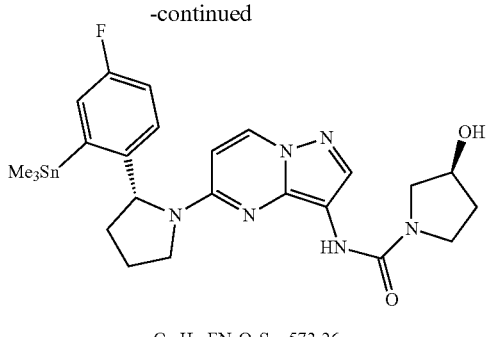

C₂₄H₃₁FN₆O₂Sn: 573.26
(R)-4-F-2-SnMe₃-Larotrectinib (R)-4-F-3-Br-Larotrectinib (98 mg, 0.2 mmol), solvent 1,4-dioxane (1 mL), bis(triphenylphosphorus) palladium dichloride (5 mg, 0.007 mmol, 0.03 eq), and hexamethyl ditin (237 mg, 0.15 mL, 0.72 mmol, 3.6 eq) were sequentially dosed in a 5 mL reaction flask. The reaction mixture was heated to 85° C. and stirred to react for 30 minutes, and TLC (acetone/chloroform=1:19, v/v) tracked the conversion of the labeled precursor and the formation process of the product until the conversion of the labeled precursor was completed. The mixture was filtered with diatomaceous earth, the filtrate was concentrated under reduced pressure, and the residue was eluted with a Sep-pak C-18 solid-phase extraction short column (ethyl acetate/n-hexane=2:8, v/v), thus obtaining a white viscous labeled precursor (64.2 mg, 56%).

MS(ESI)m/z:574.15, C₂₄H₃₁FN₆O₂Sn=573.26

Example 22. Preparation of Labeled Precursor (R)-2,5-bis(SnMe₃)-Larotrectinib

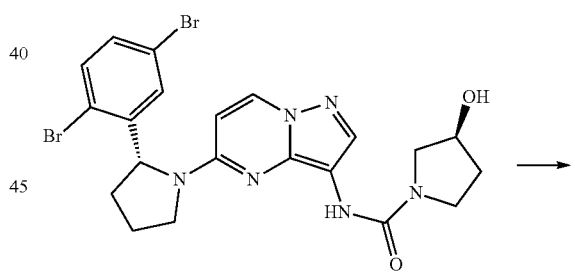

C₂₁H₂₂BrN₆O₂: 550.26
(R)-2-Br-5-Br-Larotrectinib

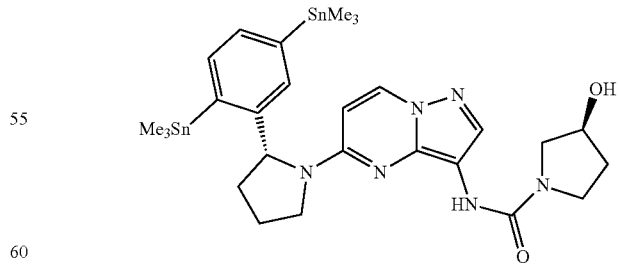

C₂₇H₄₀N₆O₂Sn: 718.08
(R)-2-SnMe₃-5-SnMe₃-Larotrectinib (R)-4-Br-3-Br-Larotrectinib (100 mg, 0.2 mmol), solvent toluene (10 mL), hexamethyl ditin (C6H18Sn2=327.63, 472 mg, 0.3 mL, 1.44 mmol, 7.2 eq), tetra(triphenylphosphorus)

palladium (Pd(PPh3)4, C72H60P4Pd=1155.56, 16.2 mg, 0.014 mmol), and hexamethyl ditin (237 mg, 0.15 mL, 0.72 mmol, 3.6 eq) were sequentially dosed in a 25 mL reaction flask. In the presence of nitrogen, the reaction mixture was heated to reflux and stirred to react for 4 hours, and TLC (acetone/chloroform=1:19, v/v) tracked the conversion of the labeled precursor and the formation process of the product until the conversion of the labeled precursor was completed. The mixture was filtered with diatomaceous earth, and the filtrate was concentrated under reduced pressure; the remaining crude product was purified by aluminum oxide column chromatography (70-230 meshes), and elution with n-hexane/dichloromethane (20:80, v/v) and rinsing with 100% dichloromethane were then carried out, thus obtaining the light yellow oily target product (66.1 mg, 46%).

MS(ESI)m/z:718.13, $C_{24}H_{31}FN_6O_2Sn$=718.08

Example 23. Preparation of Labeled Precursor (R)-2-F-4-SnMe$_3$-Larotrectinib

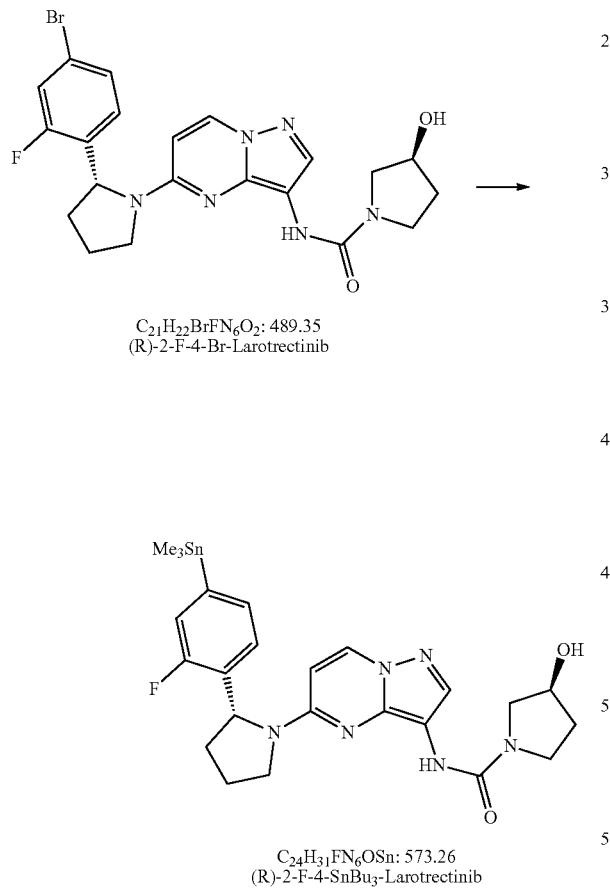

$C_{21}H_{22}BrFN_6O_2$: 489.35
(R)-2-F-4-Br-Larotrectinib $C_{24}H_{31}FN_6OSn$: 573.26
(R)-2-F-4-SnBu$_3$-Larotrectinib (R)-3-F-4-Br-Larotrectinib (98 mg, 0.2 mmol), solvent toluene (3 mL), (915.72 g/mol+404.64=1320.36) tris(dibenzylideneacetone)dipalladium/di-tri-tert-butylphosphorus (9.3 mg) (Pd2(dba)3/P(t-Bu)) 3, and hexamethyl ditin (237 mg, 0.15 mL, 0.72 mmol, 3.6 eq) were sequentially dosed in a 5 mL reaction flask. The reaction mixture was heated to 116° C. and stirred to react for 3 hours, and TLC (acetone/chloroform=1:19, v/v) tracked the conversion of the labeled precursor and the formation process of the product until the conversion of the labeled precursor was completed. The mixture was filtered with diatomaceous earth, and the filtrate was concentrated under reduced pressure; the remaining crude product was purified by aluminum oxide column chromatography (70-230 meshes), and elution with n-hexane/dichloromethane (20:80, v/v) and rinsing with 100% dichloromethane were then carried out, thus obtaining the light yellow oily target product (59.62 mg, 52%).

MS(ESI)m/z:574.15, $C_{24}H_{31}FN_6O_2Sn$=573.26

Example 24. Preparation of Labeled Precursor (R)-4-F-3-SnMe$_3$-Larotrectinib

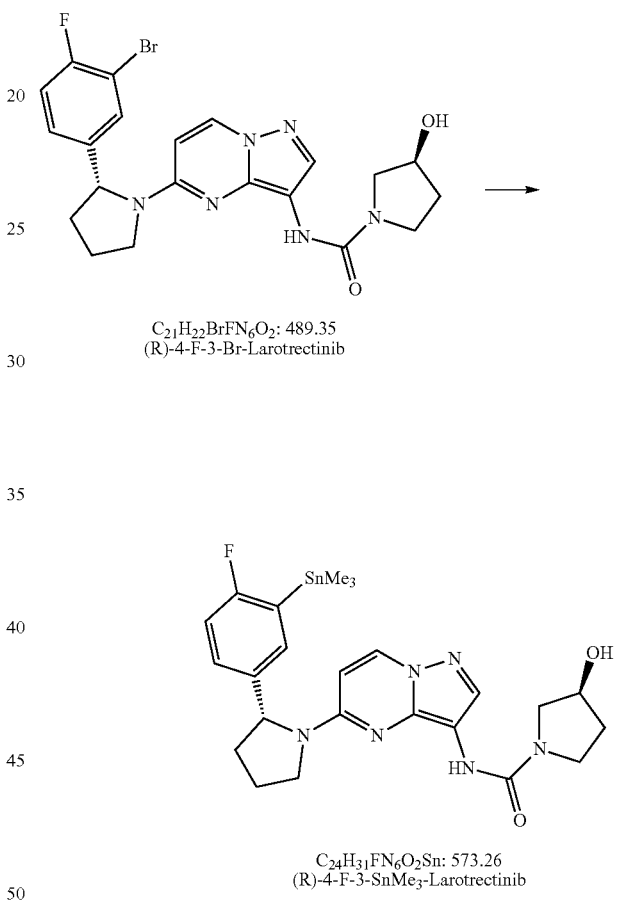

$C_{21}H_{22}BrFN_6O_2$: 489.35
(R)-4-F-3-Br-Larotrectinib $C_{24}H_{31}FN_6O_2Sn$: 573.26
(R)-4-F-3-SnMe$_3$-Larotrectinib (R)-4-F-3-Br-Larotrectinib (100 mg, 0.2 mmol), solvent 1,4-dioxane (1 mL), bis(triphenylphosphorus) palladium dichloride (5 mg, 0.007 mmol, 0.03 eq), and hexamethyl ditin (237 mg, 0.15 mL, 0.72 mmol, 3.6 eq) were sequentially dosed in a 10 mL reaction flask. The reaction mixture was heated to 85° C. and stirred to react for 15 minutes, and TLC (acetone/chloroform=1:19) tracked the conversion of the labeled precursor and the formation process of the product until the conversion of the labeled precursor was completed. The mixture was filtered with diatomaceous earth, the filtrate was concentrated under reduced pressure, and the residue was eluted with a Sep-pak C-18 solid-phase extraction short column (ethyl acetate/n-hexane=2:8), thus obtaining a white viscous labeled precursor (64.2 mg, 56%).

MS(ESI)m/z:574.15, $C_{24}H_{31}FN_6O_2Sn$=573.26

81

Step 5: Preparation of Radioactive I-Labeled Product (R)-[$^{123, 124, 125, 130, 131}$I]-Larotrectinib Example 25. Preparation of (R)-2,5-Bis-[$^{123, 124, 125, 130, 131}$I]-Larotrectinib by Radioisotope Iodine Labeling

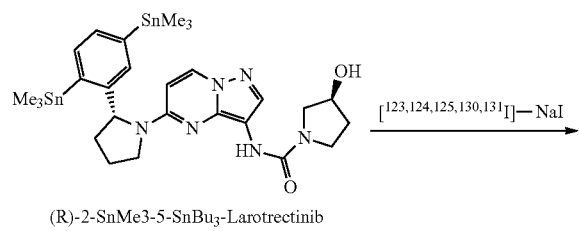

(R)-2-SnMe3-5-SnBu3-Larotrectinib (R)-2-5-Di-[$^{123,124,125,130,131}$I]-Larotrectinib The labeled precursor (R)-2-SnMe$_3$-5-SnMe$_3$-Larotrectinib (6 mg) was dosed in a sharp-bottomed V-shaped reaction flask, 0.2 mL of ethanol was dosed, and then [$^{123, 124, 125, 130, 131}$I] sodium iodide (0.5 mL, 0.1M), hydrochloric acid (0.5 mL, 0.1M), and chloramine T (1 mg/mL, 0.5 mL) were dosed, the sharp-bottomed V-shaped reaction flask was capped and sealed, and the mixed solution was vortexed for 15 minutes to react at room temperature of 25° C.; then, sodium pyrosulfate (200 mg/mL, 1 mL), saturated sodium bicarbonate (1 mL), and brine (1 mL) were dosed. The V-shaped reaction flask was shaken evenly on a vortex shaker, and the liquid in the reaction flask was poured into the Sep-pak C-18 solid-phase extraction column, and rinsed with 2.5 mL of water. Driving by blowing nitrogen was carried out for 10 min; the product was eluted into the sample tube with absolute ethanol (4 mL); the eluate was collected and concentrated under reduced pressure. The residue was purified by radioactive reversed-phase C18 preparative HPLC and eluted with acetonitrile-water (70:30, v/v) as mobile phase, and radioactive (R)-2,5-bis-[$^{123, 124, 125, 130, 131}$I]-Larotrectinib product peaks were collected; the eluents containing the product were combined and concentrated under reduced pressure; the residue was filtered by a 0.45 um filter membrane and collected in a V-shaped sample tube, thus obtaining the product (R)-2,5-bis-[$^{123, 124, 125, 130, 131}$I]-Larotrectinib with the radiochemical yield of 38% and the chemical purity and radiochemical purity of greater than 99%. For small animal SPECT tumor imaging, tumor-bearing mice and control mice can be injected with 0.76 mCi/mL and 1.39 mCi/mL respectively for tumor imaging experiments.

82

Example 26. Preparation of (R)-5-F-2-[$^{123, 124, 125, 130, 131}$I]-Larotrectinib by Radioisotope Iodine Labeling

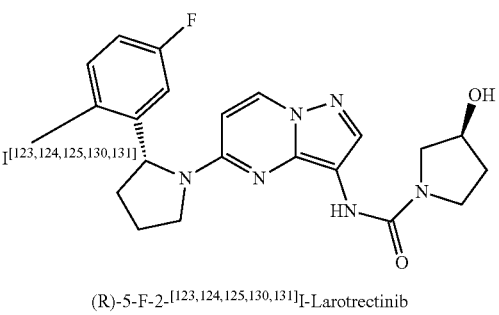

(R)-5-F-2-SnMe3-Larotrectinib (R)-5-F-2-[$^{123,124,125,130,131}$I]-Larotrectinib A solution of [$^{123, 124, 125, 130, 131}$I] sodium iodide (70 mCi) dissolved in 0.35 mL of water, glacial acetic acid (0.3 mL), H$_2$SO$_4$ (0.01 mL) were sequentially dosed in a 5 mL reaction tube and then ultrasonically shaken for 1 minute. 1.5 mL of a mixed solution (2:3, v/v) of glacial acetic acid and hydrogen peroxide (300% wt) was dosed and the mixture was ultrasonically shaken for 1 minute. A mixed solution (0.3 mL) of dichloromethane and organotin labeled precursor (5 mg) was dosed, and the mixture was ultrasonically shaken for 20 minutes at room temperature. Na$_2$S$_2$O$_3$ (2M, 0.8 mL) was dosed to quench the reaction. Dichloromethane (1 mL) was dosed to dilute the reaction mixture, the reaction mixture was layered, the organic layer was collected, and the aqueous layer was extracted twice again, 1 mL each time. The organic layers were combined, dried over anhydrous sodium sulfate and filtered, and the filtrate was poured into an aluminium oxide short column treated with dichloromethane, and then eluted with a mixed solution (3 mL) of dichloromethane and methanol (2:1, v/v); the eluate was collected and concentrated under reduced pressure; the residue was purified by radioactive reversed-phase C$_{18}$ preparative HPLC and eluted with acetonitrile-water (80:20, v/v) as the mobile phase, and radioactive (R)-5-F-2-[$^{123, 124, 125, 130, 131}$I]-Larotrectinib product peaks were collected. The eluents containing the product were combined and concentrated under reduced pressure; the residue was filtered by a 0.45 um filter membrane and collected in a V-shaped sample tube, thus obtaining the product (R)-5-F-2-[$^{123, 124, 125, 130, 131}$I]-Larotrectinib with the radiochemical yield of 56% and the chemical purity and radiochemical purity of greater than 99%.

Example 27. Preparation of (R)-2-F-5-[$^{123, 124, 125, 130, 131}$I]-Larotrectinib by Radioisotope Iodine Labeling

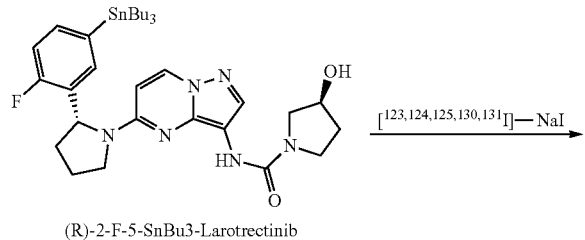

(R)-2-F-5-SnBu3-Larotrectinib

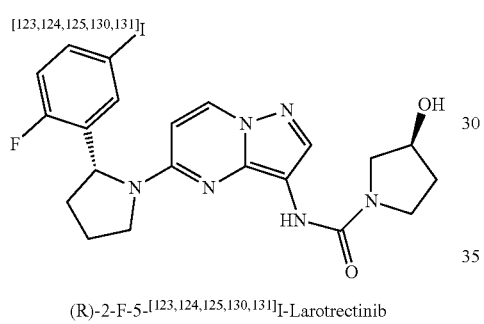

(R)-2-F-5-[$^{123,124,125,130,131}$I]-Larotrectinib

[124I]NaI (0.1M, 1 mL, 7.8 mg, 0.052 mmol, 7.5 eq) and double distilled water (0.5 mL) were sequentially dosed in a 50 mL reaction flask and ultrasonically shaken for 2 minutes. Then, 5 mL of a mixed solution of glacial acetic acid and 30% hydrogen peroxide (1:1.5, v/v) was dosed, and then the mixture was ultrasonically shaken for 1 minute. 2 mL of a mixed solution of dichloromethane and organotin labeled precursor (4 mg, 0.007 mmol, 1 eq) was added, and the mixture was ultrasonically shaken to react for 20 minutes. The reaction was quenched with sodium pyrosulfate (0.1, 10 mL); water (5 mL) and dichloromethane (10 mL) were dosed, and the mixture was mixed to be uniform and then layered; the organic layer was collected, loaded on a neutral aluminium oxide column, and then eluted with a mixed solution (10 mL) of dichloromethane and methanol (2:1, v/v); the eluate was collected and concentrated under reduced pressure; the residue was purified by radioactive reversed-phase C$_{18}$ preparative HPLC and eluted with acetonitrile-water (80:20, v/v) as the mobile phase, and radioactive (R)-5-F-2-[$^{123, 124, 125, 130, 131}$I]-Larotrectinib product peaks were collected. The eluents containing the product were combined and concentrated under reduced pressure; the residue was filtered by a 0.45 um filter membrane and collected in a V-shaped sample tube, thus obtaining the (R)-2-F-5-[$^{123, 124, 125, 130, 131}$I]-Larotrectinib with the radiochemical yield of 56% and the chemical purity and radiochemical purity of greater than 99%.

Example 28. Preparation of (R)-4-F-3-[$^{123, 124, 125, 130, 131}$I]-Larotrectinib by Radioisotope Iodine Labeling

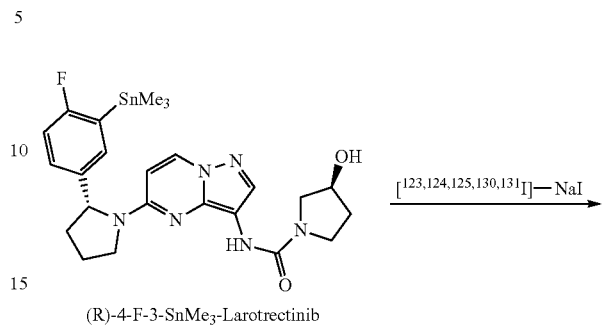

(R)-4-F-3-SnMe3-Larotrectinib

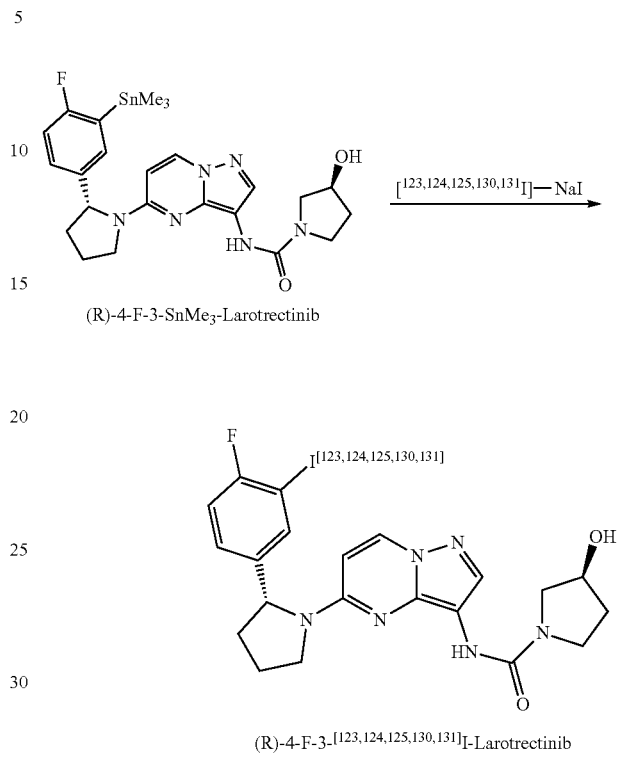

(R)-4-F-3-[$^{123,124,125,130,131}$I]-Larotrectinib

The labeled precursor (R)-4-F-3-SnMe$_3$-Larotrectinib (4 mg) was dosed in a sharp-bottomed V-shaped reaction flask, 1.2 mL of ethanol was then dosed, acetic acid (1 mL, 0.1N) and 100 microliters of 5% peroxyacetic acid were then dosed sequentially, an appropriate amount of [$^{123\cdot124\cdot125\cdot130\cdot131}$I] sodium iodide (1 mL, 0.1M) was dosed, the sharp-bottomed V-shaped reaction flask was capped and sealed, the mixture was vortexed at 25° C. to react for 30 minutes, and the post treatment was carried out in the same way as that in Example 8, thus obtaining the compound mentioned in the title. The labeling time was 35 minutes, the radiochemical yield was 42%, and the radiochemical purity was greater than 99%.

Example 29. Preparation of (R)-2-F-4-[$^{123, 124, 125, 130, 131}$I]-Larotrectinib by Radioisotope Iodine Labeling

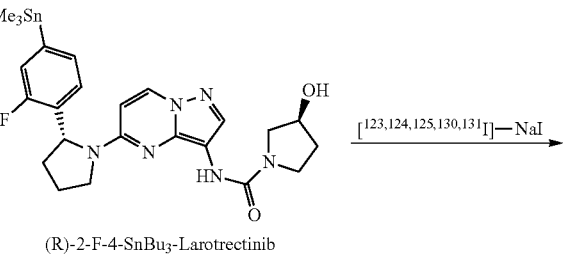

(R)-2-F-4-SnBu3-Larotrectinib

-continued

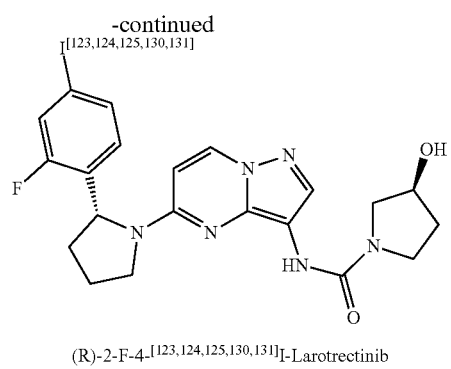

(R)-2-F-4-[123,124,125,130,131]I-Larotrectinib

The labeled precursor (R)-2-F-4-SnBu$_3$-Larotrectinib (4 mg) was dosed in a sharp-bottomed V-shaped reaction flask, 1.2 mL of ethanol was then dosed, acetic acid (1 mL, 0.1N) and 500 microliters of 30% hydrogen peroxide were then dosed sequentially, an appropriate amount of [$^{123\cdot 124\cdot 125\cdot 130\cdot 131}$I] sodium iodide (1 mL, 0.1M) was dosed, the sharp-bottomed V-shaped reaction flask was capped and sealed, the mixture was vortexed at 25° C. to react for 30 minutes, and the post treatment was carried out in the same way as that in Example 8, thus obtaining the compound mentioned in the title. The labeling time was 35 minutes, the radiochemical yield was 42%, and the radiochemical purity was greater than 99%.

Example 30. Preparation of (R)-4-F-2-[$^{123,\ 124,\ 125,\ 130,\ 131}$I]-Larotrectinib by Radioisotope Iodine Labeling

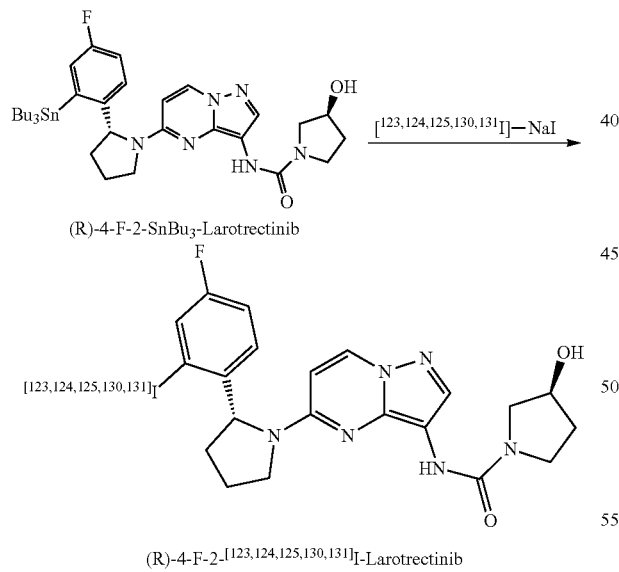

The labeled precursor (R)-4-F-2-SnBu$_3$-Larotrectinib (4 mg) was dosed in a sharp-bottomed V-shaped reaction flask, 1.2 mL of ethanol was then dosed, acetic acid (1 mL, 0.1N) and 500 microliters of tert-butyl peroxy acid were then dosed sequentially, an appropriate amount of [$^{123\cdot 124\cdot 125\cdot 130\cdot 131}$I] sodium iodide (1 mL, 0.1M) was dosed, the sharp-bottomed V-shaped reaction flask was capped and sealed, the mixture was vortexed at 25° C. to react for 30 minutes, and the post treatment was carried out in the same way as that in Example 8, thus obtaining the compound mentioned in the title. The labeling time was 35 minutes, the radiochemical yield was 41%, and the radiochemical purity was greater than 99%.

What is claimed is:

1. A preparation method of a radioactive I-labeled Larotrectinib compound, wherein the method comprises the following steps:

step 1: key intermediate 4 and its synthesis

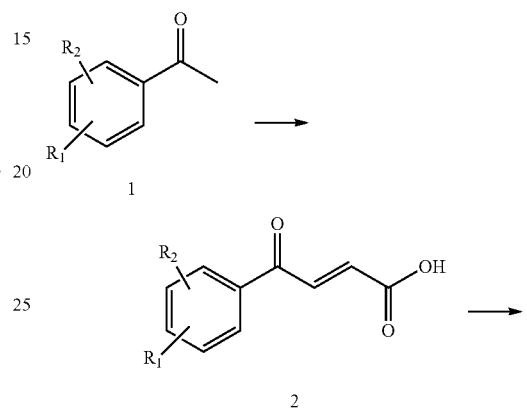

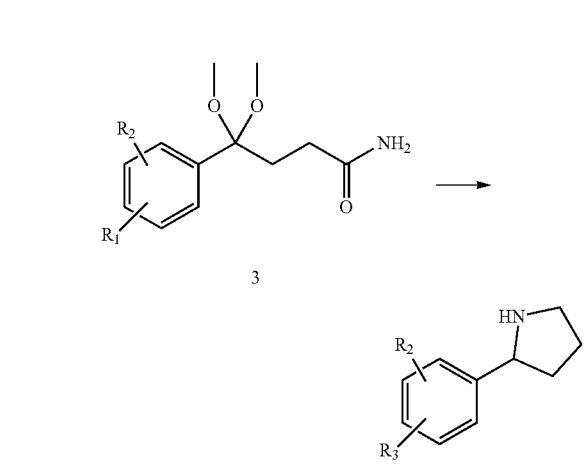

step 2: key intermediate 8 and its synthesis

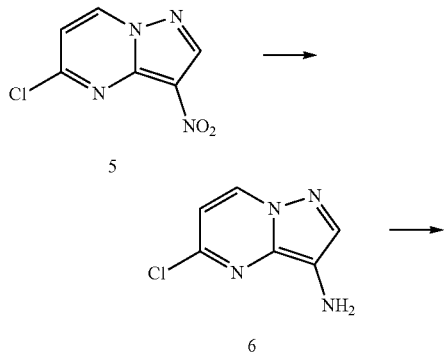

87

-continued

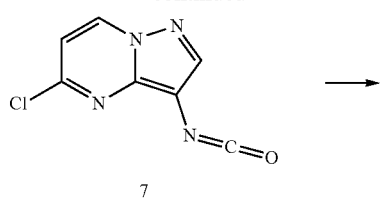
7

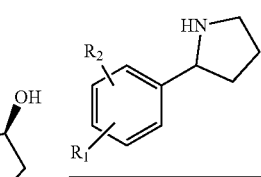
8 step 3: preparation of halogenated larotrectinib analog 9

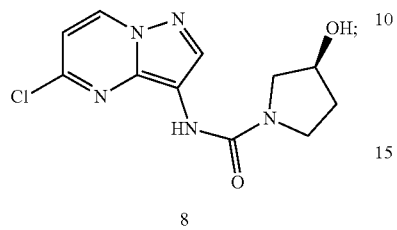
8

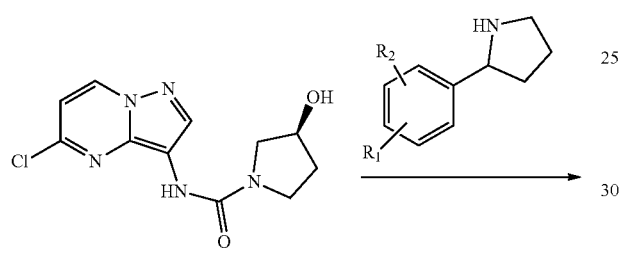
9 step 4: synthesis of labeled precursor 10

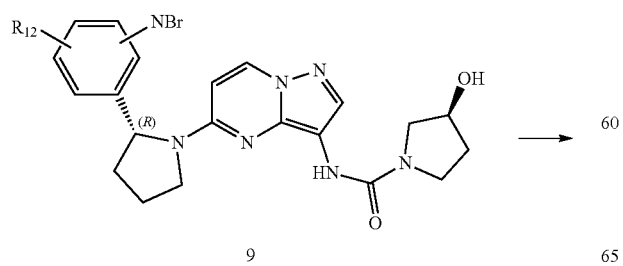
9

88

-continued

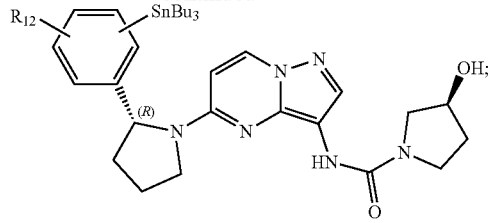
10 and
step 5: synthesis of target product

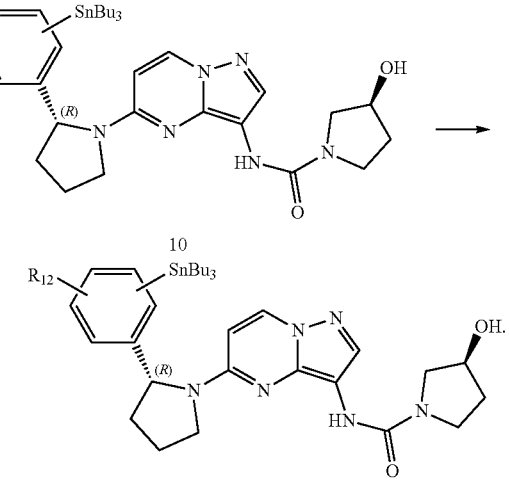
10

11

2. The preparation method of the radioactive I-labeled Larotrectinib compound according to claim 1, wherein in the structural formula 1 of the material used in the step 1,

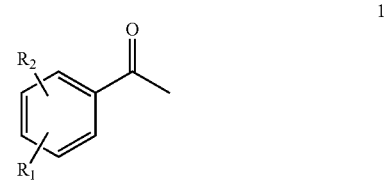
1

$R_1$ and $R_2$ are H, F, Cl, Br or I, respectively.

3. The preparation method of the radioactive I-labeled Larotrectinib compound according to claim 1, wherein the key intermediate 4 in the step 1 comprises the following compounds: 2-(5-fluoro-2-iodophenyl)pyrrolidine, 2-(2-fluoro-5-iodophenyl)pyrrolidine, 2-(2,5-diiodophenyl)pyrrolidine, 2-(2,5-dibromophenyl)pyrrolidine, 2-(2-bromo-4-fluorophenyl)pyrrolidine, 2-(3-bromo-4-fluorophenyl)pyrrolidine, 2-(4-Bromo-3-fluorophenyl)pyrrolidine, or 2-(3-fluoro-5-iodophenyl)pyrrolidine.

4. The preparation method of the radioactive I-labeled Larotrectinib compound according to claim 3, wherein the synthesis of 2-(5-fluoro-2-iodophenyl)pyrrolidine comprises the following methods:

(11) synthesis of (E)-4-(5-fluoro-2-iodophenyl)-4-oxobut-2-enoic acid, following the reaction formula as follows:

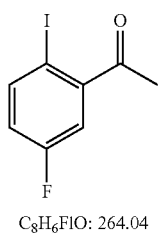

C₈H₆FIO: 264.04

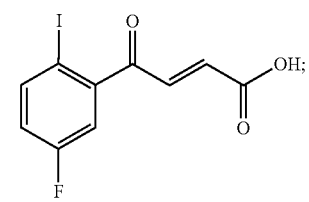

C₁₀H₆FIO₃: 320.06

(12) synthesis of 4-(5-fluoro-2-iodophenyl)-4-oxobutanoic acid, following the reaction formula as follows:

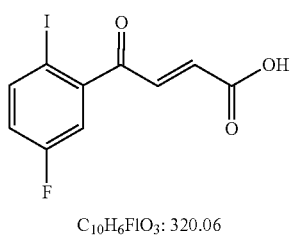

C₁₀H₆FIO₃: 320.06

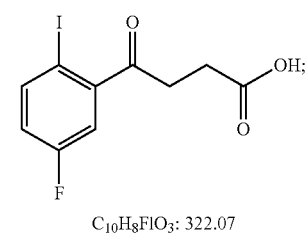

C₁₀H₈FIO₃: 322.07

(13) synthesis of methyl 4-(5-fluoro-2-iodophenyl)-4,4-dimethoxybutanoate following the reaction formula as follows:

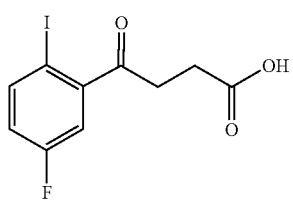

C₁₀H₈FIO₃: 322.07

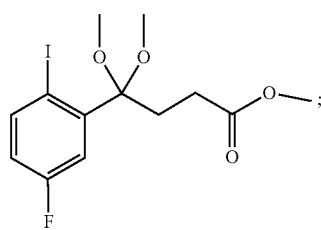

C₁₃H₁₆FIO₄: 382.17

(14) synthesis of 4-(5-fluoro-2-iodophenyl)-4-oxobutanamide, following the reaction formula as follows:

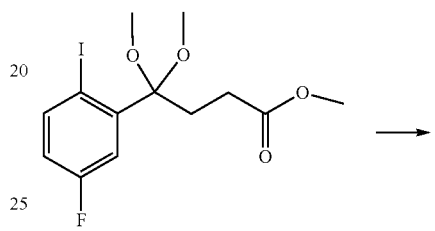

C₁₃H₁₆FIO₄: 382.17

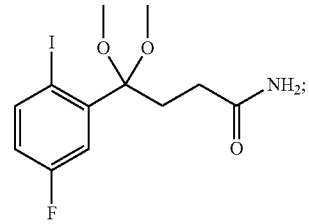

C₁₂H₁₅FINO₃: 367.16

(15) synthesis of 5-(5-fluoro-2-iodophenyl)-3,4-dihydro-2H-pyrrole, following the reaction formula as follows:

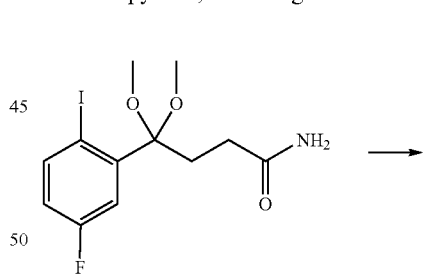

C₁₂H₁₅FINO₃: 367.16

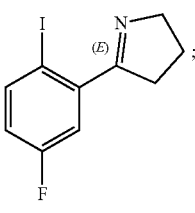

C₁₀H₉FIN: 289.09 and

(16) synthesis of 2-(5-fluoro-2-iodophenyl)pyrrolidine, following the reaction formula as follows:

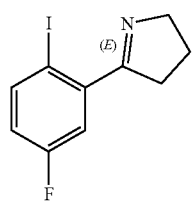

C₁₀H₉FIN: 289.09

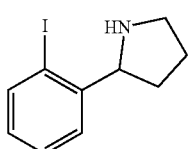

C₁₀H₁₁FIN: 291.11

5. The preparation method of the radioactive I-labeled Larotrectinib compound according to claim 3, wherein the synthesis of 2-(2-fluoro-5-iodophenyl)pyrrolidine comprises the following methods:

(21) synthesis of (E)-4-(2-fluoro-5-iodophenyl)-4-oxobut-2-enoic acid, following the reaction formula as follows:

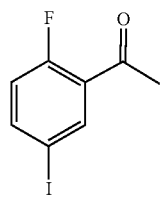

C₈H₆FIO: 264.04

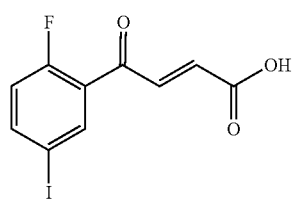

C₁₀H₆FIO₃: 320.06

(22) synthesis of 4-(2-fluoro-5-iodophenyl)-4-oxobutanoic acid, following the reaction formula as follows:

C₁₀H₆FIO₃: 320.06

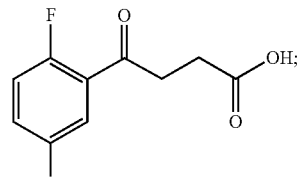

C₁₀H₈FIO₃: 322.07

(23) synthesis of methyl 4-(2-fluoro-5-iodophenyl)-4-oxobutanoate, following the reaction formula as follows:

C₁₀H₈FIO₃: 322.07

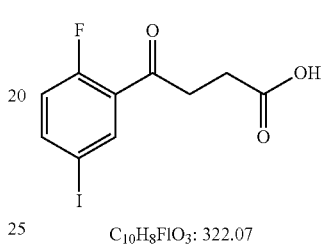

C₁₃H₁₆FIO₄: 382.17

(24) synthesis of 4-(2-fluoro-5-iodophenyl)-4-oxobutanamide, following the reaction formula as follows:

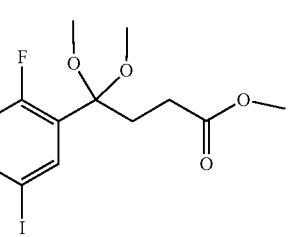

C₁₃H₁₆FIO₄: 382.17

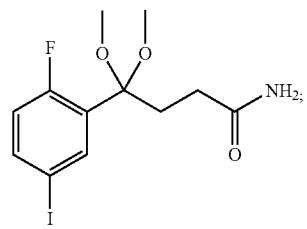

C₁₂H₁₅FINO₃: 367.16

(25) synthesis of 5-(2-fluoro-5-iodophenyl)-3,4-dihydro-2H-pyrrole, following the reaction formula as follows:

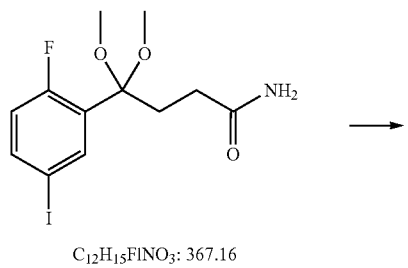

C₁₂H₁₅FINO₃: 367.16

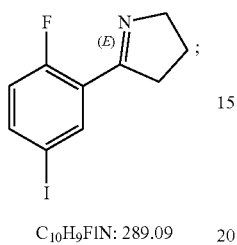

C₁₀H₉FIN: 289.09 and

(26) synthesis of 2-(5-fluoro-2-iodophenyl)pyrrolidine, following the reaction formula as follows:

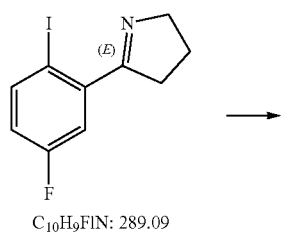

C₁₀H₉FIN: 289.09

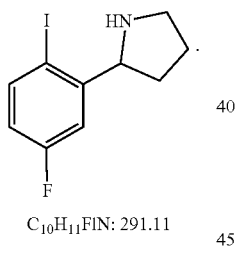

C₁₀H₁₁FIN: 291.11

6. The preparation method of the radioactive I-labeled Larotrectinib compound according to claim 3, wherein the synthesis of 2-(2,5-diiodophenyl)pyrrolidine comprises the following methods:

(31) synthesis of (E)-4-(2-iodo-5-iodophenyl)-4-oxobut-2-enoic acid, following the reaction formula as follows:

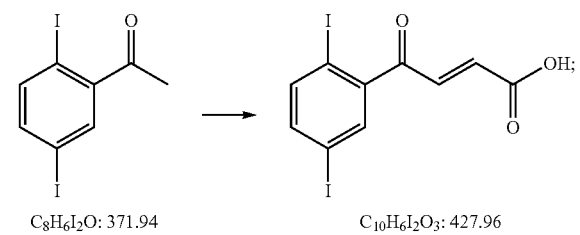

C₈H₆I₂O: 371.94       C₁₀H₆I₂O₃: 427.96

(32) synthesis of 4-(2,5-diiodophenyl)-4-oxobutanoic acid, following the reaction formula as follows:

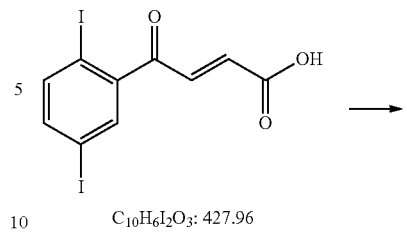

C₁₀H₆I₂O₃: 427.96

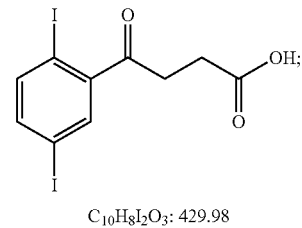

C₁₀H₈I₂O₃: 429.98

(33) synthesis of methyl 4-(2,5-diiodophenyl)-4-oxobutanoate, following the reaction formula as follows:

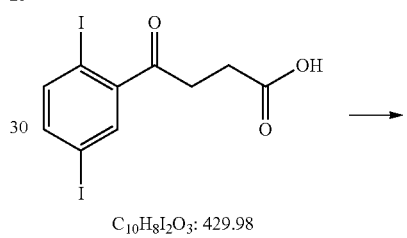

C₁₀H₈I₂O₃: 429.98

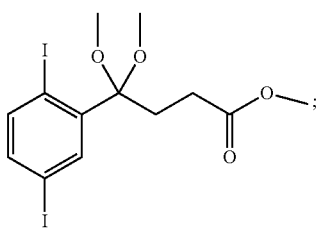

C₁₀H₁₆I₂O₄: 490.08

(34) synthesis of 4-(2,5-diiodophenyl)-4-oxobutanamide, following the reaction formula as follows:

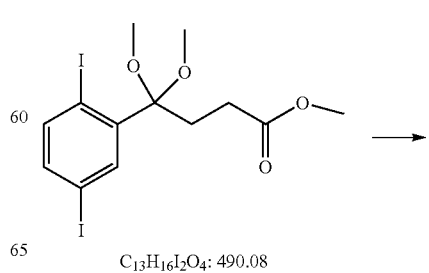

C₁₃H₁₆I₂O₄: 490.08

-continued

C₁₂H₁₅I₂NO₃: 475.06

(35) synthesis of 5-(2,5-iodophenyl)-3,4-dihydro-2H-pyrrole, following the reaction formula as follows:

C₁₂H₁₅I₂NO₃: 475.06 → (E) C₁₀H₉I₂N: 397.00 and

(36) synthesis of 2-(2,5-diiodophenyl)pyrrolidine, following the reaction formula as follows:

C₁₀H₉I₂N: 397.00 → C₁₀H₁₁I₂N: 399.01

7. The preparation method of the radioactive I-labeled Larotrectinib compound according to claim 3, wherein the synthesis of 2-(2,5-dibromophenyl)pyrrolidine comprises the following methods:

(41) synthesis of (E)-4-(2,5-dibromophenyl)-4-oxobut-2-enoic acid, following the reaction formula as follows:

C₈H₆Br₂O: 277.94 → C₁₀H₆Br₂O₃: 333.96

(42) synthesis of 4-(2,5-dibromophenyl)-4-oxobutanoic acid, following the reaction formula as follows:

C₁₀H₆Br₂O₃: 333.96 → C₁₀H₈Br₂O₃: 335.98

(43) synthesis of methyl 4-(2,5-dibromophenyl)-4-oxobutanoate, following the reaction formula as follows:

C₁₀H₈Br₂O₃: 335.98 → C₁₃H₁₆Br₂O₄: 396.08

(44) synthesis of 4-(2,5-dibromophenyl)-4-oxobutanamide, following the reaction formula as follows:

C₁₃H₁₆Br₂O₄: 396.08 →

97

-continued

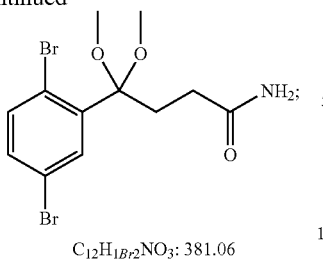

(45) synthesis of 5-(2,5-bromophenyl)-3,4-dihydro-2H-pyrrole, following the reaction formula as follows:

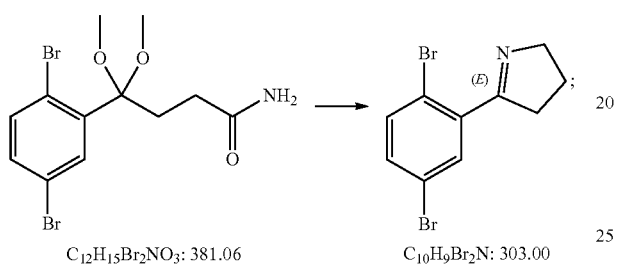

and

(46) synthesis of 2-(2,5-diiodophenyl)pyrrolidine, following the reaction formula as follows:

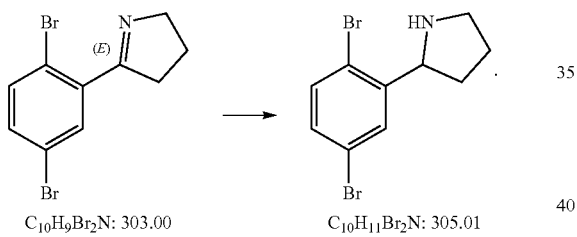

8. The preparation method of the radioactive I-labeled Larotrectinib compound according to claim 3, wherein the synthesis of 2-(2-bromo-4-fluorophenyl)pyrrolidine comprises the following methods:

(51) synthesis of (E)-4-(2-bromo-4-fluorohenyl)-4-oxobut-2-enoic acid, following the reaction formula as follows:

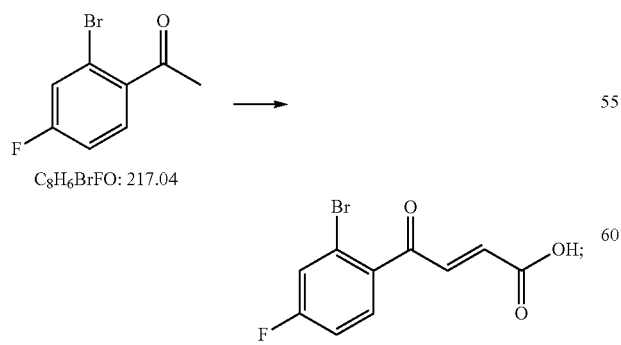

98

(52) synthesis of 4-(2-bromo-4-fluorophenyl)-4-oxobutanoic acid, following the reaction formula as follows:

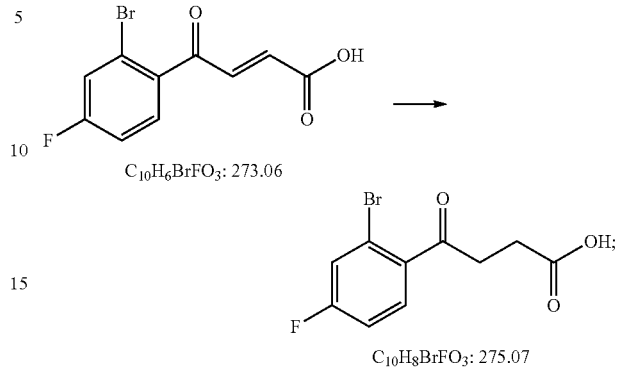

(53) synthesis of methyl 4-(2-bromo-4-fluorophenyl)-4-oxobutanoate, following the reaction formula as follows:

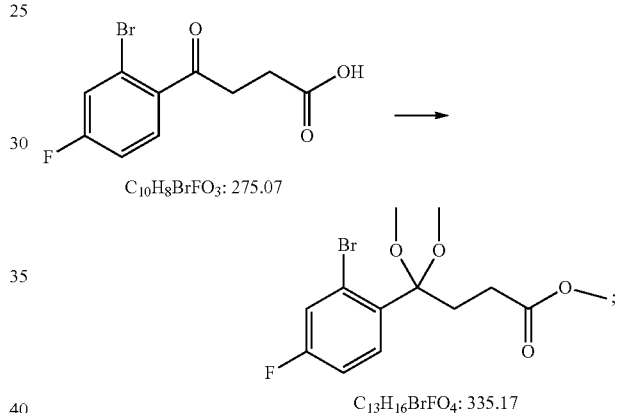

(54) synthesis of 4-(2-bromo-4-fluorophenyl)-4-oxobutanamide, following the reaction formula as follows:

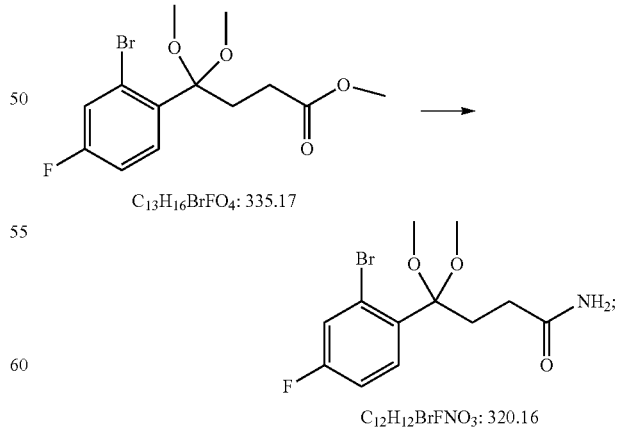

(55) synthesis of 5-(2-bromo-4-fluorophenyl)-3,4-dihydro-2H-pyrrole, following the reaction formula as follows:

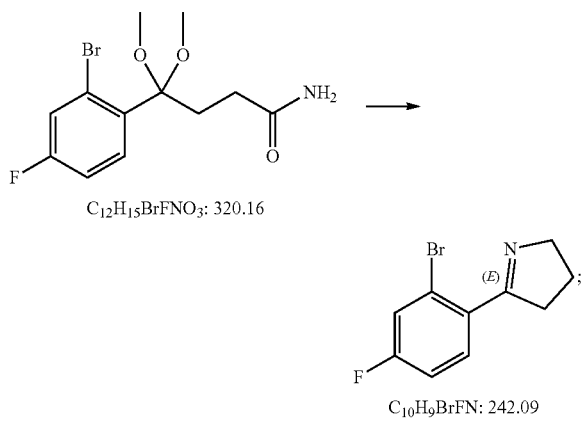

and

(56) synthesis of 2-(2-bromo-4-fluorophenyl)pyrrolidine, following the reaction formula as follows:

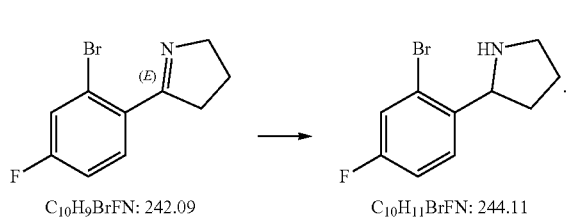 [SMILES: Fc1ccc(C2=NCCC2)c(Br)c1 ; Fc1ccc(C2CCCN2)c(Br)c1]

9. The preparation method of the radioactive I-labeled Larotrectinib compound according to claim 3, wherein the synthesis of 2-(3-bromo-4-fluorophenyl)pyrrolidine comprises the following methods:

(61) synthesis of (E)-4-(3-bromo-4-fluorohenyl)-4-oxobut-2-enoic acid, following the reaction formula as follows:

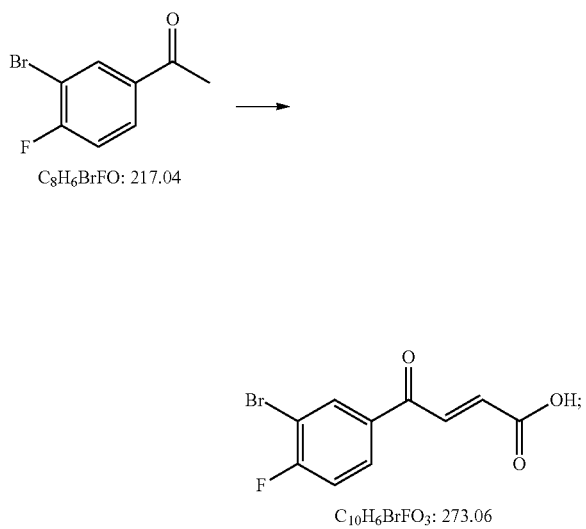

(62) synthesis of 4-(3-bromo-4-fluorophenyl)-4-oxobutanoic acid, following the reaction formula as follows:

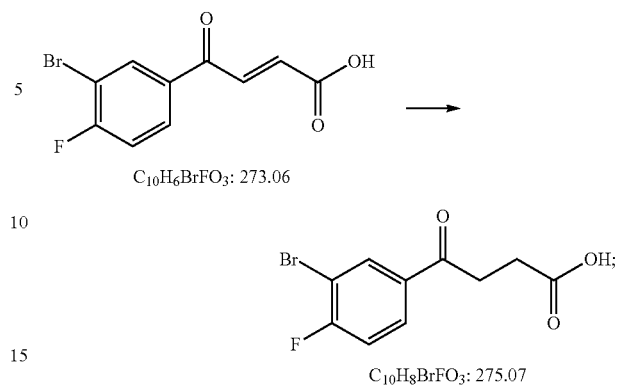

(63) synthesis of methyl 4-(3-bromo-4-fluorophenyl)-4-oxobutanoate, following the reaction formula as follows:

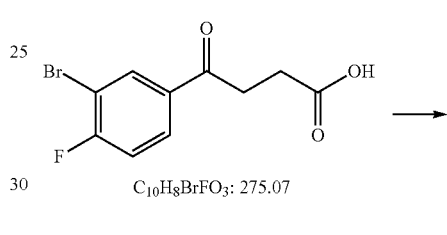

(64) synthesis of 4-(3-bromo-4-fluorophenyl)-4-oxobutanamide, following the reaction formula as follows:

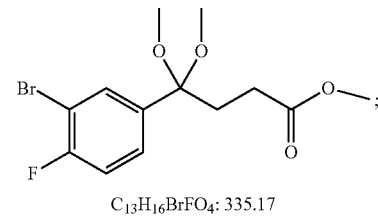

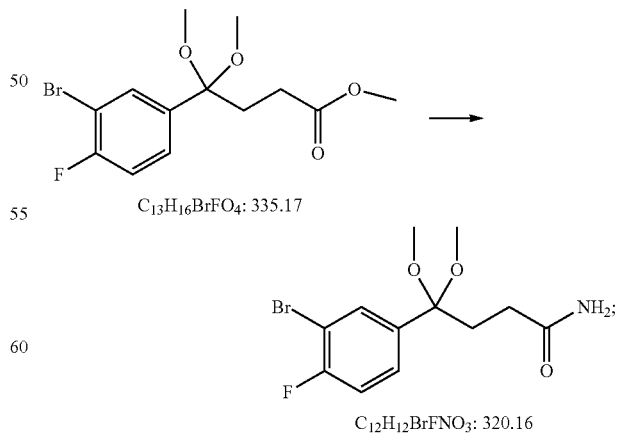

(65) synthesis of 5-(3-fluoro-4-iodophenyl)-3,4-dihydro-2H-pyrrole, following the reaction formula as follows:

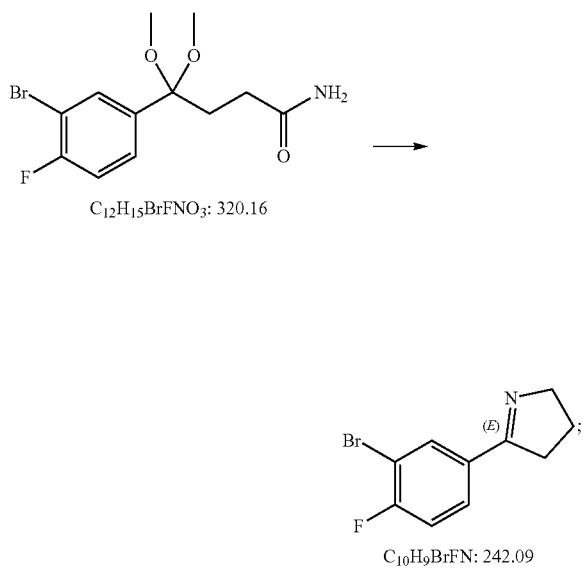

and

(66) synthesis of 2-(3-bromo-4-fluorophenyl)pyrrolidine, following the reaction formula as follows:

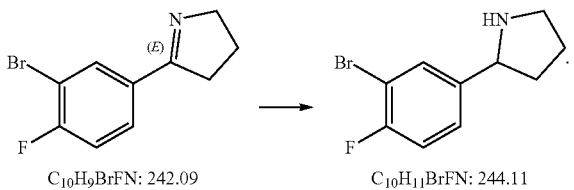 [SMILES: Fc1ccc(C2=NCCC2)cc1Br ; Fc1ccc(C2CCCN2)cc1Br]

10. The preparation method of the radioactive I-labeled Larotrectinib compound according to claim 3, wherein the synthesis of 2-(4-bromo-3-fluorophenyl)pyrrolidine comprises the following steps:

(71) synthesis of (E)-4-(4-bromo-3-fluorohenyl)-4-oxobut-2-enoic acid, following the reaction formula as follows:

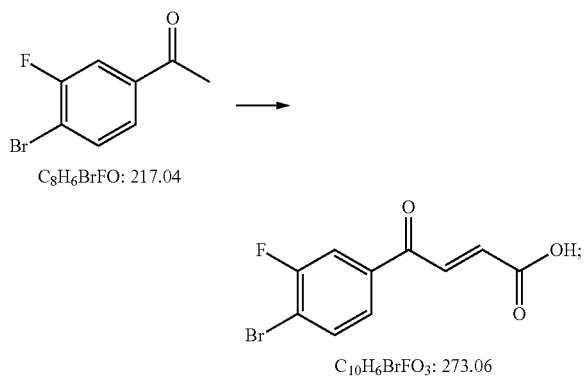

(72) synthesis of 4-(4-bromo-3-fluorophenyl)-4-oxobutanoic acid, following the reaction formula as follows:

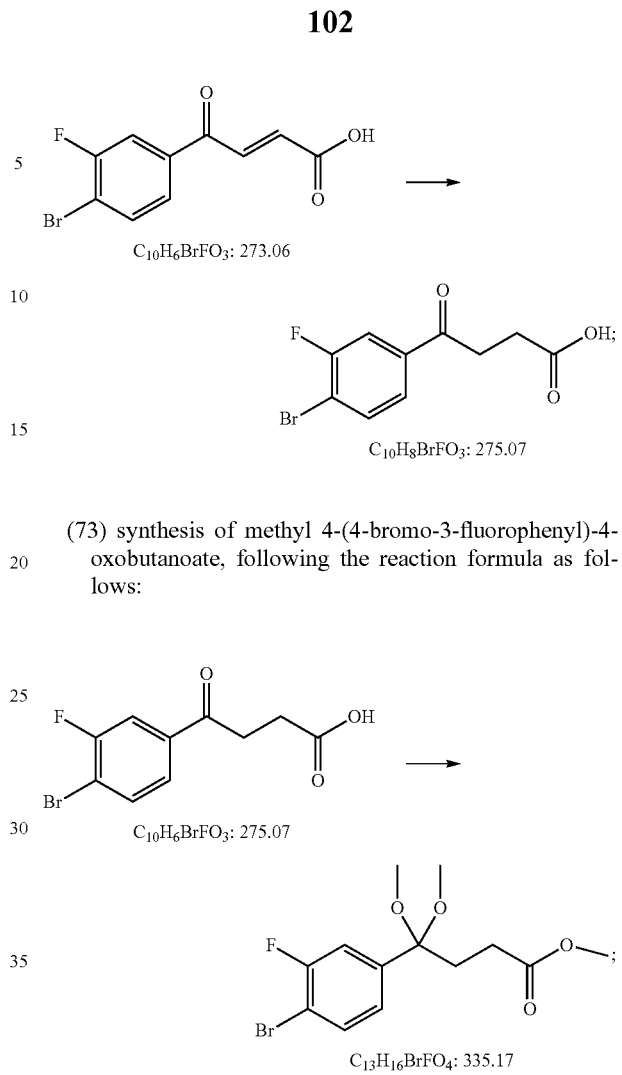

(73) synthesis of methyl 4-(4-bromo-3-fluorophenyl)-4-oxobutanoate, following the reaction formula as follows:

(74) synthesis of 4-(4-bromo-3-fluorophenyl)-4-oxobutanamide, following the reaction formula as follows:

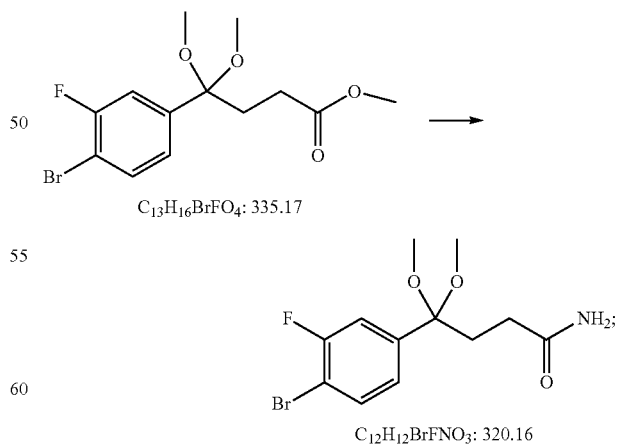

(75) synthesis of 5-(4-bromo-3-fluorophenyl)-3,4-dihydro-2H-pyrrole, following the reaction formula as follows:

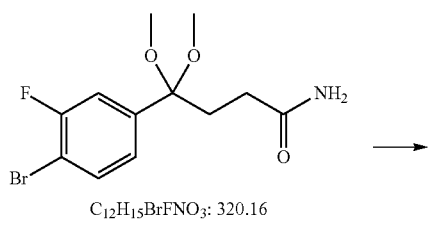

C₁₂H₁₅BrFNO₃: 320.16

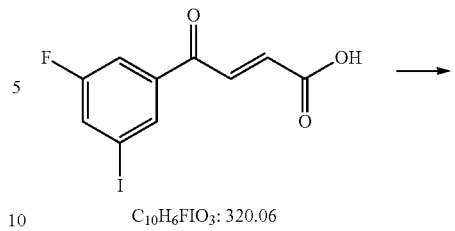

C₁₀H₆FIO₃: 320.06

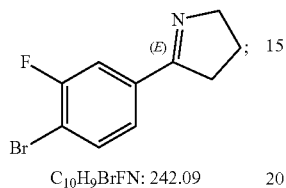

C₁₀H₉BrFN: 242.09

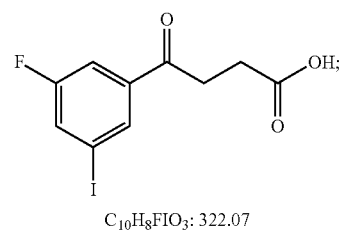

C₁₀H₈FIO₃: 322.07 and

(76) synthesis of 2-(4-bromo-3-fluorophenyl)pyrrolidine, following the reaction formula as follows:

(83) synthesis of methyl 4-(3-fluoro-5-iodophenyl)-4-oxobutanoate, following the reaction formula as follows:

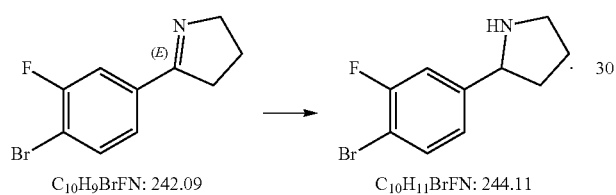

C₁₀H₉BrFN: 242.09        C₁₀H₁₁BrFN: 244.11

11. The preparation method of the radioactive I-labeled Larotrectinib compound according to claim 3, wherein the synthesis of 2-(3-fluoro-5-iodophenyl)pyrrolidine comprises the following methods:

(81) synthesis of (E)-4-(3-fluoro-5-iodophenyl)-4-oxobut-2-enoic acid, following the reaction formula as follows:

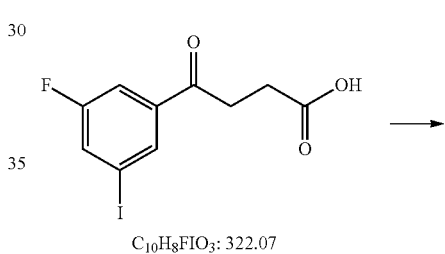

C₁₀H₈FIO₃: 322.07

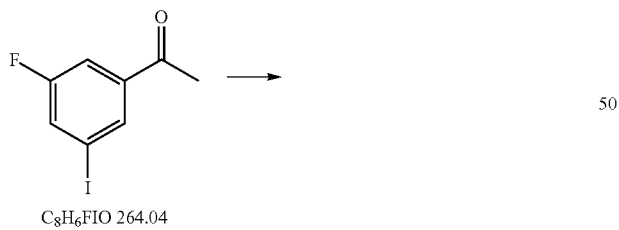

C₈H₆FIO 264.04

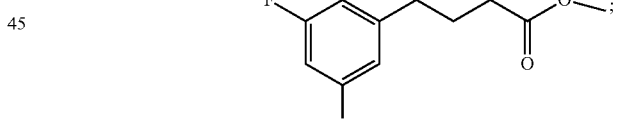

C₁₃H₁₆FIO₄: 382.17

(84) synthesis of 4-(3-fluoro-5-iodophenyl)-4-oxobutanamide, following the reaction formula as follows:

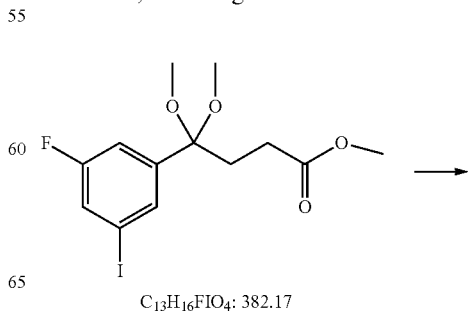

C₁₀H₆FIO₃: 320.06

(82) synthesis of 4-(3-fluoro-5-iodophenyl)-4-oxobutanoic acid, following the reaction formula as follows:

C₁₃H₁₆FIO₄: 382.17

105

-continued

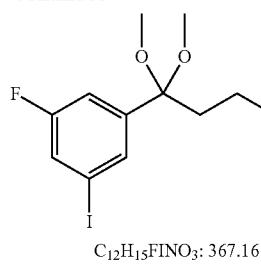

C₁₂H₁₅FINO₃: 367.16

(85) synthesis of 5-(3-fluoro-5-iodophenyl)-3,4-dihydro-2H-pyrrole, following the reaction formula as follows:

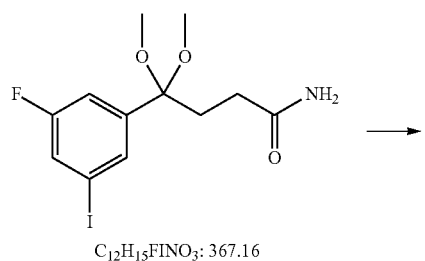

C₁₂H₁₅FINO₃: 367.16

C₁₀H₉FIN: 289.09 and

(86) synthesis of 2-(3-fluoro-5-iodophenyl)pyrrolidine, following the reaction formula as follows:

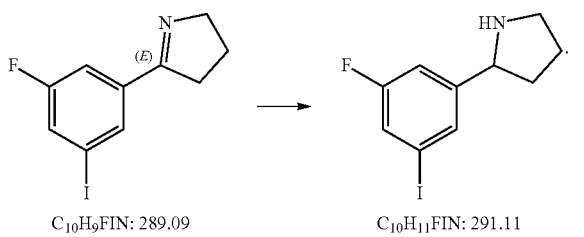 [SMILES: Fc1cc(I)cc(C2=NCCC2)c1 ; Fc1cc(I)cc(C2CCCN2)c1]

C₁₀H₉FIN: 289.09   C₁₀H₁₁FIN: 291.11

12. The preparation method of the radioactive I-labeled Larotrectinib compound according to claim 1, wherein the key intermediate 8 in the step 2 comprises the following compound: (S)—N-(5-chloropyrazolo[1,5-a]pyrimidin-3-yl)-3-hydroxypyrrolidine-1-carboxamide; and the synthesis of (S)—N-(5-chloropyrazolo[1,5-a]pyrimidin-3-yl)-3-hydroxypyrrolidine-1-carboxamide comprises the following steps:

(1) synthesis of 5-chloropyrazolo[1,5-a]pyrimidin-3-amine, following the reaction formula as follows:

106

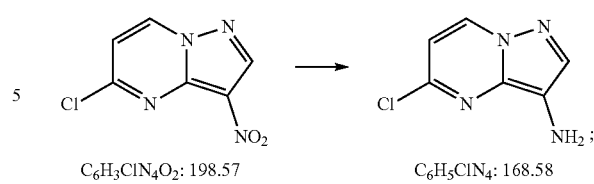

C₆H₃ClN₄O₂: 198.57   C₆H₅ClN₄: 168.58

(2) synthesis of 5-chloro-3-isocyanatopyrazolo[1,5-a]pyrimidine, following the reaction formula as follows:

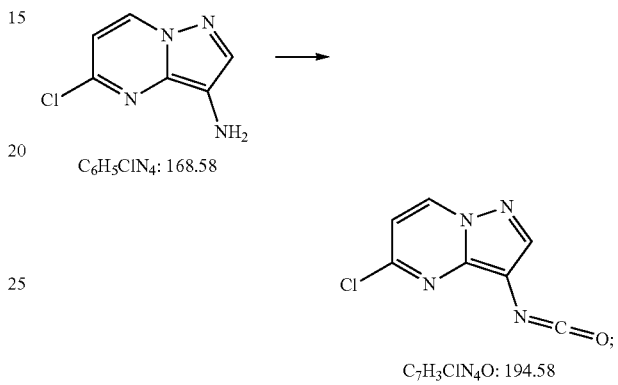

C₆H₅ClN₄: 168.58

C₇H₃ClN₄O: 194.58

(3) synthesis of (S)—N-(5-chloropyrazolo[1,5-a]pyrimidin-3-yl)-3-hydroxypyrrolidine-1-carboxamide, following the reaction formula as follows:

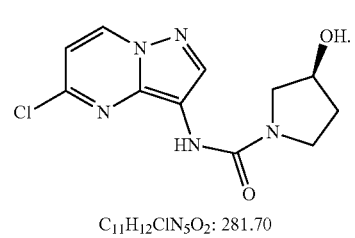

C₇H₃ClN₄O: 194.58

C₁₁H₁₂ClN₅O₂: 281.70

13. A The preparation method of the radioactive I-labeled Larotrectinib compound according to claim 1, wherein the preparation of the halogenated Larotrectinib analog 9 in the step 3 comprises: obtaining a racemic halogenated Larotrectinib analog by the reaction of the intermediate 4 and the intermediate 8, and then separating and purifying the racemic halogenated Larotrectinib analog by chiral LC, thus obtaining the chiral halogenated Larotrectinib analog 9; the preparation specifically comprises the following methods:

(1) synthesis of halogenated larotrectinib compound (R)-2-F-5-I-LarotrectinibR)-5-F-2-I-Larotrectinib, following the reaction formula as follows:

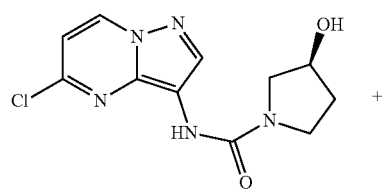

C₁₁H₁₂ClN₅O₂: 281.70
(S)-N-(5-chloropyrazolo[1,5-a]pyrimidin-3-yl)-3-hydroxypyrrolidine-1-carboxamide

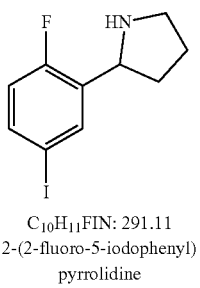

C₁₀H₁₁FIN: 291.11
2-(2-fluoro-5-iodophenyl)pyrrolidine

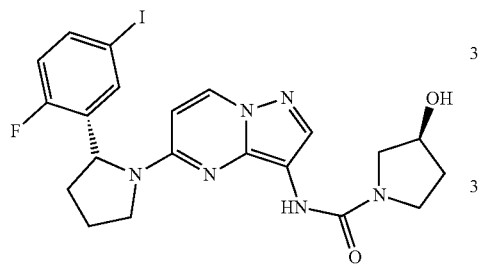

C₂₁H₂₂FIN₆O₂: 536.35
(R)-2-F-5-I-Larotrectinib (2) synthesis of halogenated larotrectinib compound (R)-2-Br-5-Br-LarotrectinibR)-2-Br-5-Br-Larotrectinib, following the reaction formula as follows:

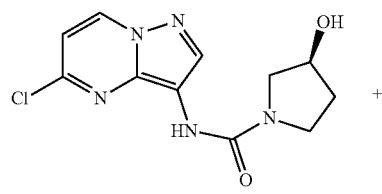

C₁₁H₁₂ClN₅O₂: 281.70

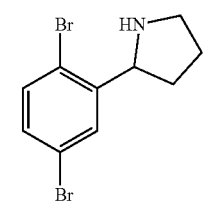

C₁₀H₁₁Br₂N: 305.01
2-(2,5-dibromophenyl)pyrrolidine

-continued

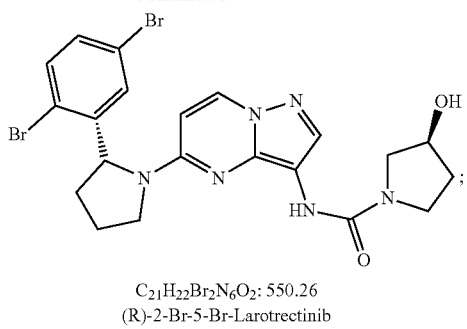

C₂₁H₂₂Br₂N₆O₂: 550.26
(R)-2-Br-5-Br-Larotrectinib (3) synthesis of halogenated larotrectinib compound (R)-5-F-2-I-Larotrectinib, following the reaction formula as follows:

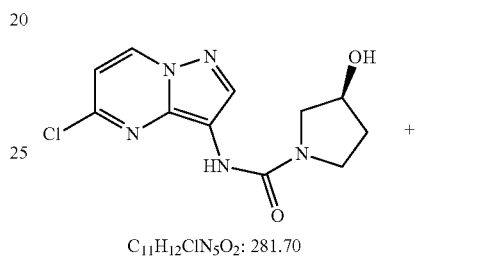

C₁₁H₁₂ClN₅O₂: 281.70

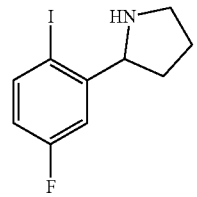

C₁₀H₁₁FIN: 291.11
2-(5-fluoro-2-iodophenyl)pyrrolidine

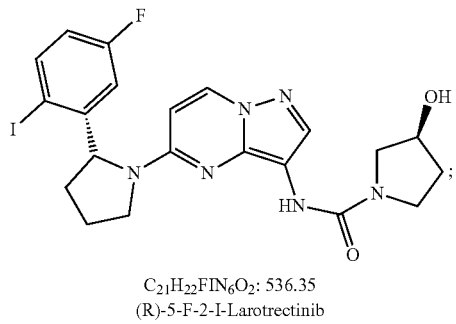

C₂₁H₂₂FIN₆O₂: 536.35
(R)-5-F-2-I-Larotrectinib (4) synthesis of halogenated larotrectinib compound (R)-5-I-2-I-Larotrectinib, following the reaction formula as follows:

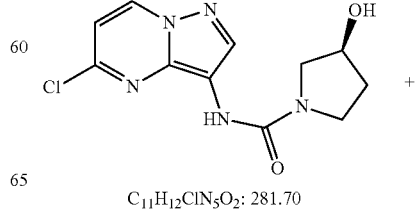

C₁₁H₁₂ClN₅O₂: 281.70

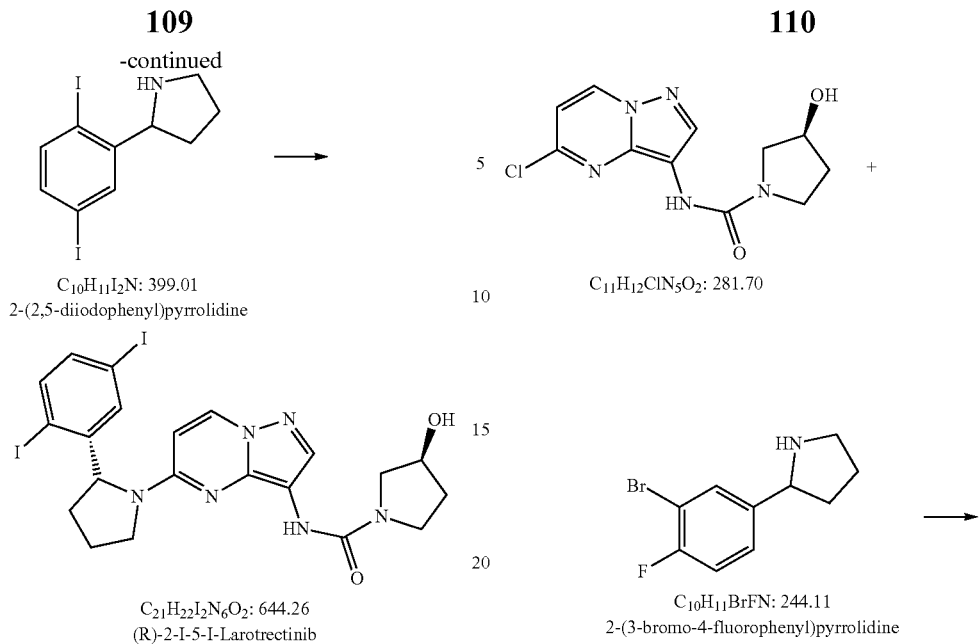
(5) synthesis of halogenated larotrectinib compound R)-4-F-2-Br-Larotrectinib, following the reaction formula as follows:
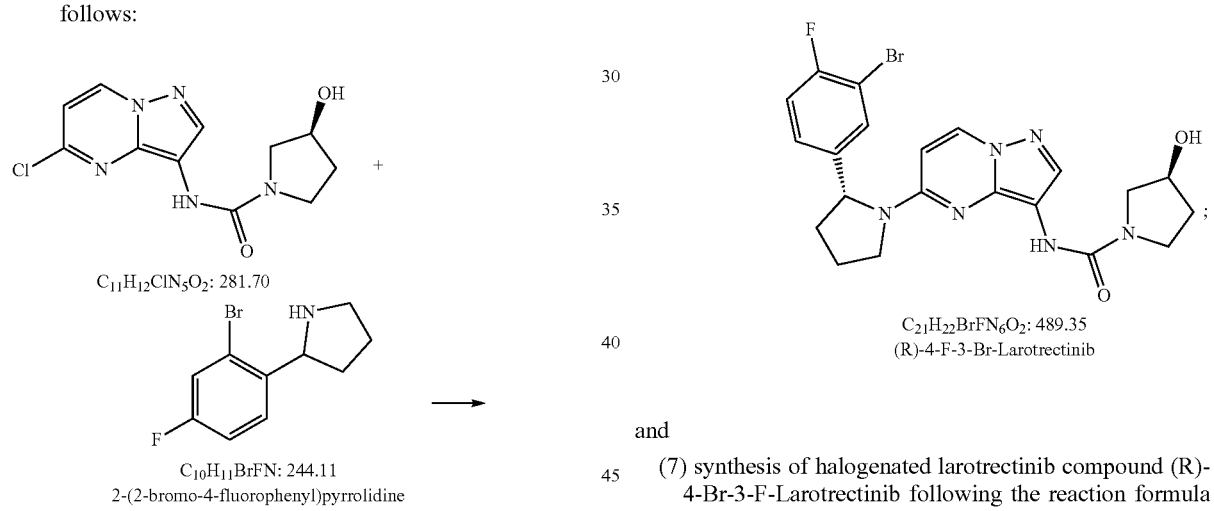
(6) synthesis of halogenated larotrectinib compound (R)-4-F-3-Br-Larotrectinib, following the reaction formula as follows:
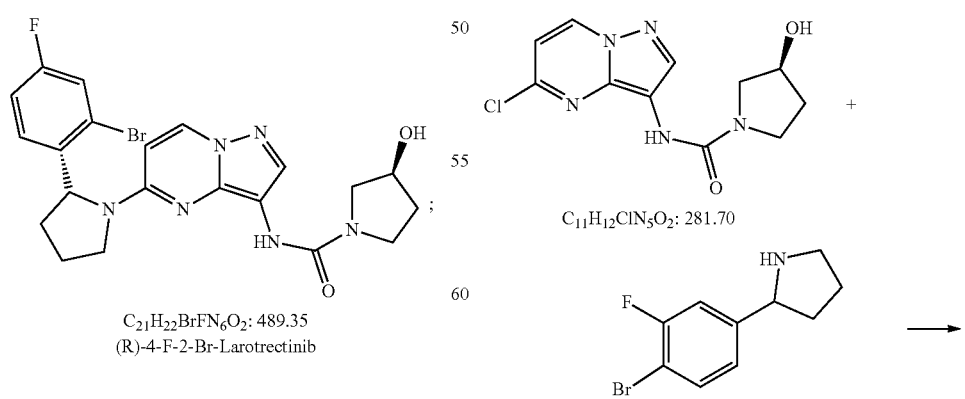
and
(7) synthesis of halogenated larotrectinib compound (R)-4-Br-3-F-Larotrectinib following the reaction formula as follows:

111

-continued

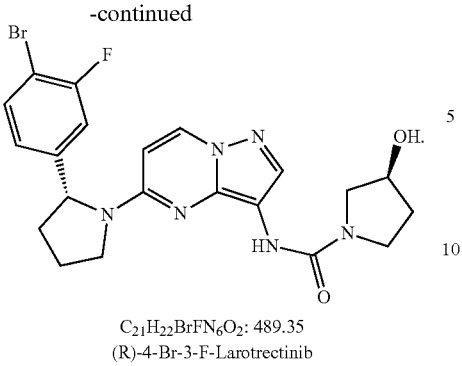

C$_{21}$H$_{22}$BrFN$_6$O$_2$: 489.35
(R)-4-Br-3-F-Larotrectinib

14. The preparation method of the radioactive I-labeled Larotrectinib compound according to claim 1, wherein the preparation of the labeled precursor in the step 3 comprises the following methods:

(1) preparation of labeled precursor (R)-2-fluoro-5-tributyltin-Larotrectinib, following the reaction formula as follows:

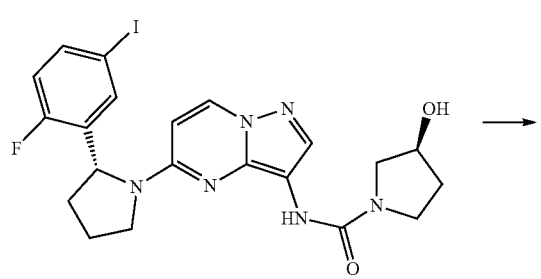

C$_{21}$H$_{22}$FIN$_6$O$_2$: 536.35
(R)-2-F-5-I-Larotrectinib

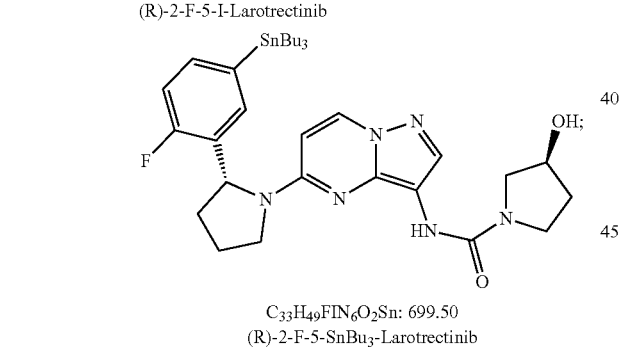

C$_{33}$H$_{49}$FN$_6$O$_2$Sn: 699.50
(R)-2-F-5-SnBu$_3$-Larotrectinib or,

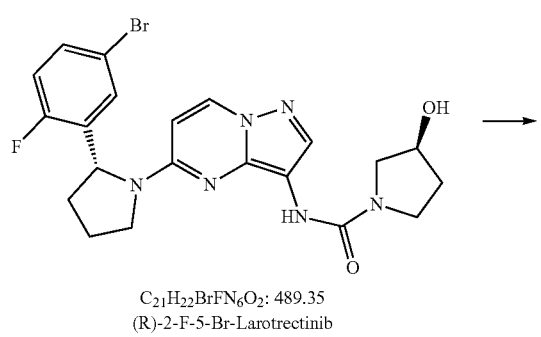

C$_{21}$H$_{22}$BrFN$_6$O$_2$: 489.35
(R)-2-F-5-Br-Larotrectinib

112

-continued

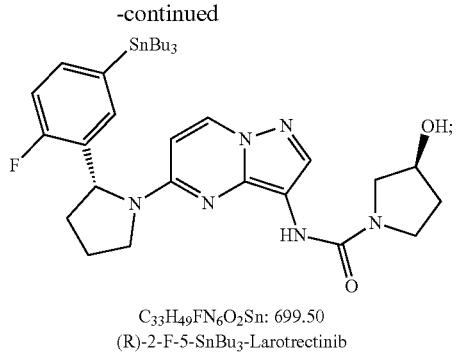

C$_{33}$H$_{49}$FN$_6$O$_2$Sn: 699.50
(R)-2-F-5-SnBu$_3$-Larotrectinib (2) preparation of labeled precursor (R)-5-F-2-SnMe$_3$-Larotrectinib, following the reaction formula as follows:

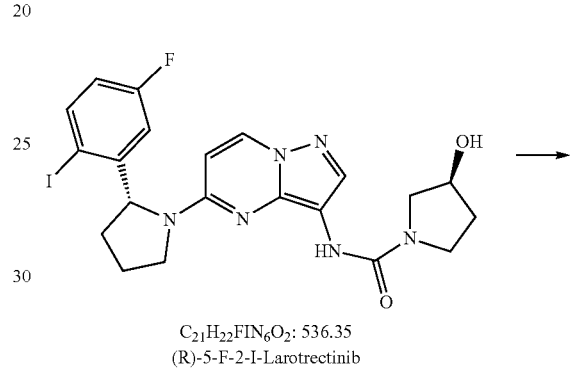

C$_{21}$H$_{22}$FIN$_6$O$_2$: 536.35
(R)-5-F-2-I-Larotrectinib

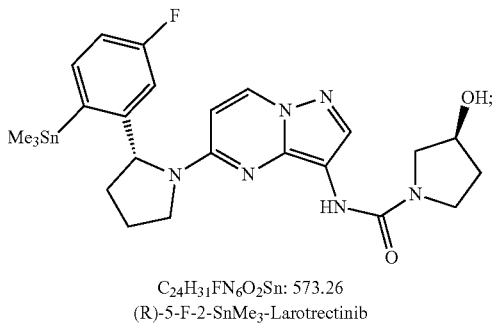

C$_{24}$H$_{31}$FN$_6$O$_2$Sn: 573.26
(R)-5-F-2-SnMe$_3$-Larotrectinib (3) preparation of labeled precursor (R)-3-F-5-SnMe$_3$-Larotrectinib, following the reaction formula as follows:

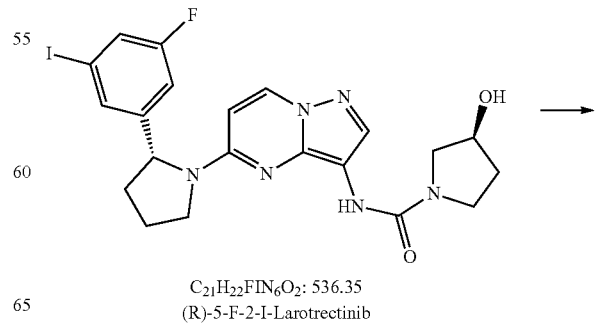

C$_{21}$H$_{22}$FIN$_6$O$_2$: 536.35
(R)-5-F-2-I-Larotrectinib

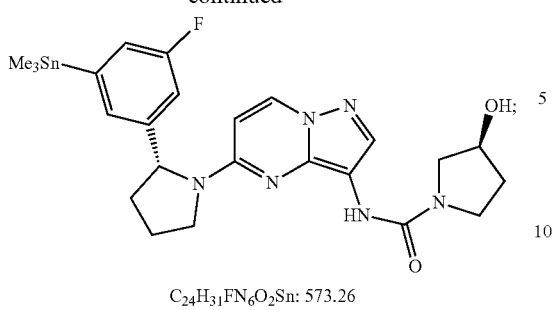

$C_{24}H_{31}FN_6O_2Sn$: 573.26
(R)-5-F-2-SnMe$_3$-Larotrectinib

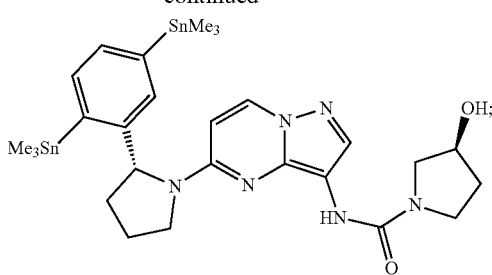

$C_{27}H_{40}N_6O_2Sn_2$: 718.08
(R)-2-SnMe$_3$-5-SnMe$_3$-Larotrectinib (4) preparation of labeled precursor (R)-4-F-2-SnMe$_3$-Larotrectinib, following the reaction formula as follows:

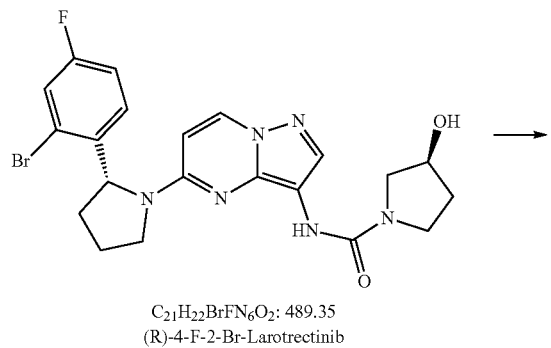

$C_{21}H_{22}BrFN_6O_2$: 489.35
(R)-4-F-2-Br-Larotrectinib

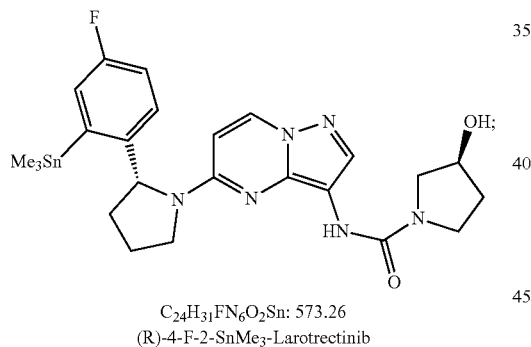

$C_{24}H_{31}FN_6O_2Sn$: 573.26
(R)-4-F-2-SnMe$_3$-Larotrectinib (5) preparation of labeled precursor (R)-2,5-bis(SnMe$_3$)-Larotrectinib, following the reaction formula as follows:

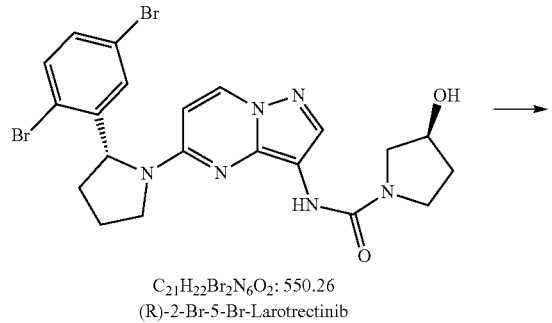

$C_{21}H_{22}Br_2N_6O_2$: 550.26
(R)-2-Br-5-Br-Larotrectinib (6) preparation of labeled precursor (R)-2-F-4-SnMe$_3$-Larotrectinib, following the reaction formula as follows:

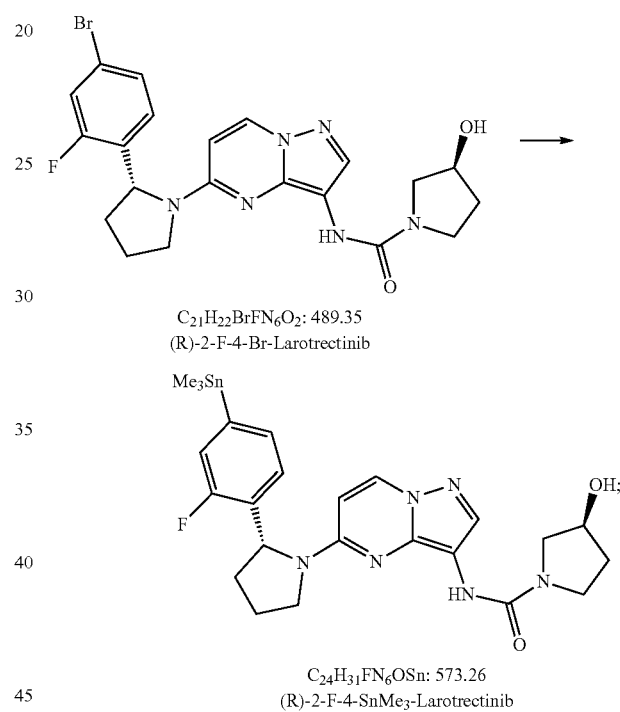

$C_{21}H_{22}BrFN_6O_2$: 489.35
(R)-2-F-4-Br-Larotrectinib $C_{24}H_{31}FN_6OSn$: 573.26
(R)-2-F-4-SnMe$_3$-Larotrectinib and (7) preparation of labeled precursor (R)-4-F-3-SnMe$_3$-Larotrectinib, following the reaction formula as follows:

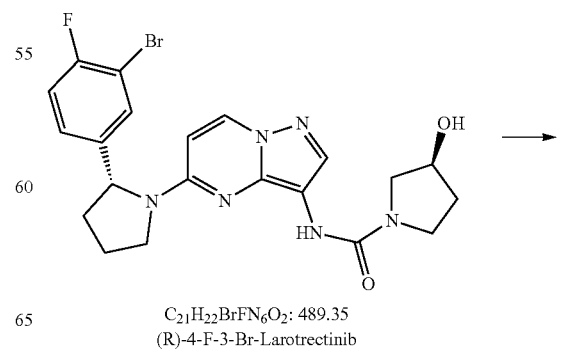

$C_{21}H_{22}BrFN_6O_2$: 489.35
(R)-4-F-3-Br-Larotrectinib

-continued

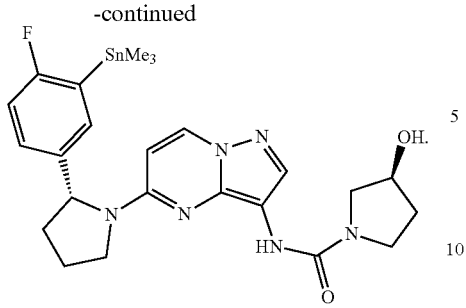

C$_{24}$H$_{31}$FN$_6$O$_2$Sn: 573.26
(R)-4-F-3-SnMe$_3$-Larotrectinib

15. The preparation method of the radioactive I-labeled Larotrectinib compound according to claim 1, wherein the target product in the step 5 comprises (R)-2,5-bis-[$^{123,\ 124,\ 125,\ 130,\ 131}$I]-Larotrectinib, (R)-5-F-2-[$^{123,\ 124,\ 125,\ 130,\ 131}$I]-Larotrectinib, (R)-2-F-5-[$^{123,\ 124,\ 125,\ 130,\ 131}$I]-Larotrectinib, (R)-4-F-3-[$^{123,\ 124,\ 125,\ 130,\ 131}$I]-Larotrectinib, (R)-2-F-4-[$^{123,\ 124,\ 125,\ 130,\ 131}$I]-Larotrectinib, or (R)-4-F-2-[$^{123,\ 124,\ 125,\ 130,\ 131}$I]-Larotrectinib.

16. The preparation method of the radioactive I-labeled Larotrectinib compound according to claim 15, wherein the preparation method of the target product is as follows:

(1) preparation of radioisotope I-labeled product (R)-2,5-bis-[$^{123,\ 124,\ 125,\ 130,\ 131}$I]-Larotrectinib by radioisotope iodine labeling, following the reaction formula as follows:

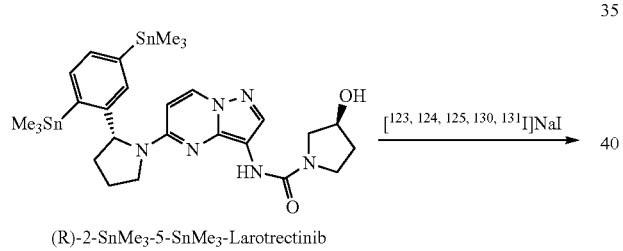

(R)-2-5-Di-[$^{123,\ 124,\ 125,\ 130,\ 131}$I]-Larotrectinib (2) preparation of (R)-5-F-2-[$^{123,\ 124,\ 125,\ 130,\ 131}$I]-Larotrectinib by radioisotope iodine labeling, following the reaction formula as follows:

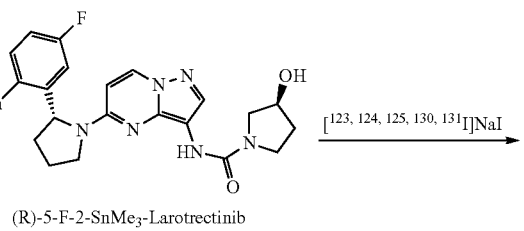

(R)-5-F-2-SnMe$_3$-Larotrectinib (R)-5-F-2-[$^{123,\ 124,\ 125,\ 130,\ 131}$I]-Larotrectinib (3) preparation of (R)-2-F-5-[$^{123,\ 124,\ 125,\ 130,\ 131}$I]-Larotrectinib by radioisotope iodine labeling, following the reaction formula as follows:

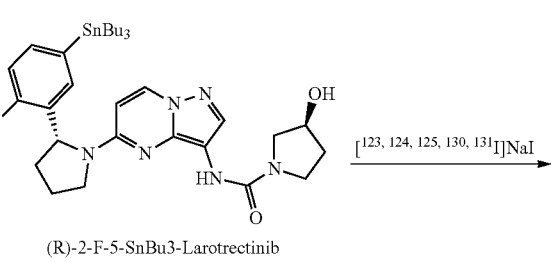

(R)-2-F-5-SnBu$_3$-Larotrectinib

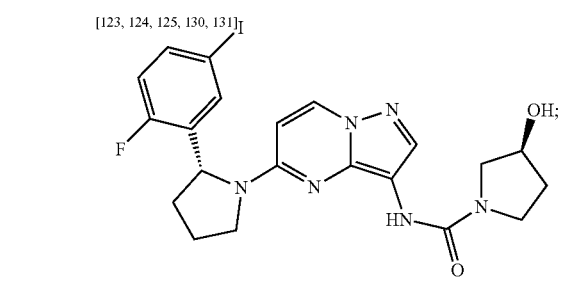

(R)-2-F-5-[$^{123,\ 124,\ 125,\ 130,\ 131}$I]-Larotrectinib (4) preparation of (R)-4-F-3-[$^{123,\ 124,\ 125,\ 130,\ 131}$I]-Larotrectinib by radioisotope iodine labeling, following the reaction formula as follows:

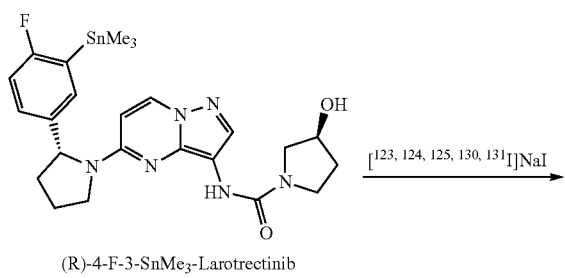
(R)-4-F-3-SnMe₃-Larotrectinib
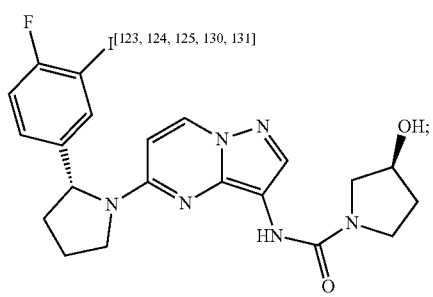
(R)-4-F-3-[123, 124, 125, 130, 131I]-Larotrectinib
(5) preparation of (R)-2-F-4-[123, 124, 125, 130, 131]I-Larotrectinib by radioisotope iodine labeling, following the reaction formula as follows:
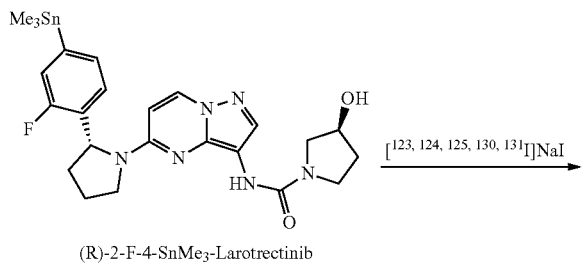
(R)-2-F-4-SnMe₃-Larotrectinib
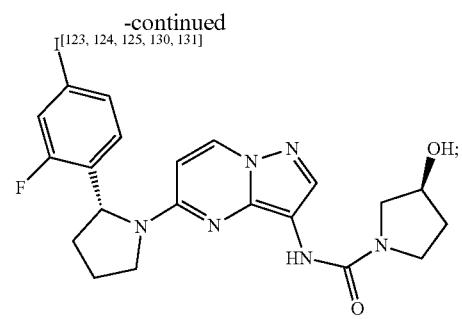
(R)-2-F-4-[123, 124, 125, 130, 131]I-Larotrectinib
(6) preparation of (R)-4-F-2-[123, 124, 125, 130, 131]I-Larotrectinib by radioisotope iodine labeling, following the reaction formula as follows:
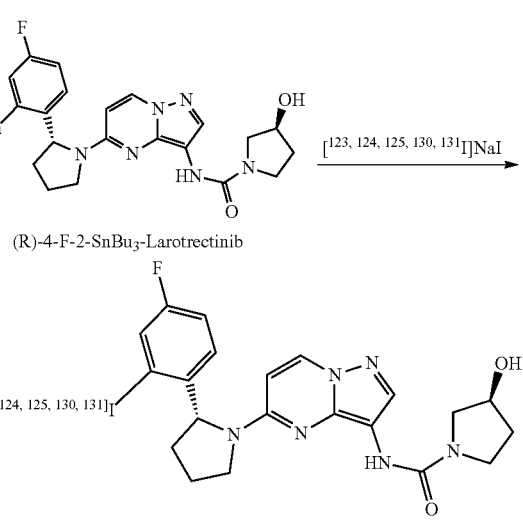
(R)-4-F-2-SnBu₃-Larotrectinib
(R)-4-F-2-[123, 124, 125, 130, 131]I-Larotrectinib
\* \* \* \* \*